(12) United States Patent
Nasoff et al.

(10) Patent No.: US 8,173,128 B2
(45) Date of Patent: *May 8, 2012

(54) METHODS AND COMPOSITIONS FOR INDUCING APOPTOSIS IN CANCER CELLS WITH AN ANTI-DR5 ANTIBODY

(75) Inventors: Marc Nasoff, San Diego, CA (US); Quinn L. Deveraux, San Diego, CA (US); Deborah A. Knee, Del Mar, CA (US); Pedro Aza-Blanc, San Diego, CA (US); Garrett M. Hampton, San Diego, CA (US); Klaus Wagner, San Diego, CA (US)

(73) Assignee: IRM LLC, Hamilton (BM)

( * ) Notice: Subject to any disclaimer, the term of this patent is extended or adjusted under 35 U.S.C. 154(b) by 484 days.

This patent is subject to a terminal disclaimer.

(21) Appl. No.: 11/607,208

(22) Filed: Dec. 1, 2006

(65) Prior Publication Data
US 2007/0128204 A1 Jun. 7, 2007

Related U.S. Application Data

(62) Division of application No. 10/723,383, filed on Nov. 25, 2003, now Pat. No. 7,229,617.

(60) Provisional application No. 60/504,901, filed on Sep. 22, 2003, provisional application No. 60/494,714, filed on Aug. 12, 2003, provisional application No. 60/448,960, filed on Feb. 21, 2003, provisional application No. 60/429,842, filed on Nov. 27, 2002.

(51) Int. Cl.
*A61K 39/395* (2006.01)
*A61K 38/16* (2006.01)
(52) U.S. Cl. ............... 424/138.1; 424/133.1; 424/135.1; 514/18.9; 514/19.3
(58) Field of Classification Search .................. None
See application file for complete search history.

(56) References Cited

U.S. PATENT DOCUMENTS

| 6,342,369 | B1 * | 1/2002 | Ashkenazi |
| 7,229,617 | B2 | 6/2007 | Nasoff et al. |
| 7,279,160 | B2 * | 10/2007 | Zhou et al. |
| 7,595,046 | B2 | 9/2009 | Adams et al. |
| 2003/0148455 | A1 | 8/2003 | Adams |
| 2006/0088523 | A1 | 4/2006 | Andya et al. |
| 2009/0258011 | A1 | 10/2009 | Diamond et al. |

FOREIGN PATENT DOCUMENTS

| EP | 1 506 011 A | 2/2005 |
| EP | 1 506 285 A | 2/2005 |
| WO | WO 01/83560 A | 11/2001 |
| WO | WO 01/83560 A1 | 11/2001 |
| WO | WO 2005/114187 A2 | 12/2005 |

OTHER PUBLICATIONS

Rudikoff et al., Single amino acid substitution altering antigen-binding specificity, Proc. Natl. Acad. Sci. USA, 79:1979-1983, Mar. 1982.*
Gussow et al., Humanization of monoclonal antibodies, Meth. Enzymol. 203:99-121, 1991.*
Ashkenazi, A., et al., "Safety and antitumor activity of recombinant soluble Apo2 ligand," *The Journal of Clinical Investigation*, vol. 104(2):155-162 (Jul. 1999).
Ashkenazi, A., "Targeting Death and Decoy Receptors of the Tumor-Necrosis Factor Superfamily," *Nature Review Cancer*, vol. 2: 420-430 (Jun. 2002).
Fulda, S., et al., "Smac agonists sensitize for Apo2L/TRAIL- or anticancer drug-induced apoptosis and induce regression of malignant glioma in vivo," *Nature Medicine*, vol. 8(8):808-815 (Aug. 2002).
Griffith, T., et al., "Functional Analysis of TRAIL Receptors Using Monoclonal Antibodies," *The Journal of Immunology*, vol. 162: 2597-2605 (1999).
Huisman, C., et al., "Paclitaxel triggers cell death primarily via caspase-independent routes in the non-small cell lung cancer cell line NCI-H460," *Clinical Cancer Research*, vol. 8: 596-606 (Feb. 2002).
Kim, K., et al., "Molecular determinants of response to TRAIL in killing of normal and cancer cells," *Clinical Cancer Research*, vol. 6: 335-346 (Feb. 2000).
Kreuz, S., et al., "NF-$_K$B Inducers Upregulate cFLIP, a cycloheximide-sensitive inhibitor of death receptor signaling," *Molecular and Cellular Biology*, vol. 21(12): 3964-3973 (Jun. 2001).
Liu, W., et al., "Tumor necrosis factor-related apoptosis-inducing ligand and chemotherapy cooperate to induce apoptosis in mesothelioma cell lines," *Am. J. Respir. Cell Mol. Biol.*, vol. 25: 111-118 (2001).
Liu, X-S, et al., "Preparation and characterization of a set of monoclonal antibodies to TRAIL and TRAIL receptors DR4, DR5, DcR1, and DcR2," *Hybridoma and Hybridomics*, vol. 22(2), pp. 121-125 (Nov. 2003).
Mitsiades, C., et al., "TRAIL/Apo2L ligand selectively induces apoptosis and overcomes drug resistance in multiple myeloma: therapeutic applications," *Blood*, vol. 98(3), pp. 795-804 (Aug. 2001).
Mongkolsapaya, J., et al., "Structure of the TRAIL-DR5 complex reveals mechanisms conferring specificity in apoptotic initiation," *Nature Structural Biology*, vol. 6(11): 1048-1053 (Nov. 1999).
Poulaki, V., et al., "Regulation of Apo2L/tumor necrosis factor-related apoptosis-inducing ligand-induced apoptosis in thyroid carcinoma cells," *American Journal of Pathology*, vol. 161(2): 643-654 (Aug. 2002).
Weber, T., et al., "Vitamin E succinate is a potent novel antineoplastic agent with high selectivity and cooperativity with tumor necrosis factor-related apoptosis-inducing ligand (Apo2 ligand) in vivo," *Clinical Cancer Research*, vol. 8: 863-869 (Mar. 2002).
Adams et al., "Structural and functional analysis of the interaction between the agonistic monoclonal antibody apomab and the proapoptotic receptor DR5", Cell Death and Differentiation, 2008 vol. 15 pp. 751-761.

(Continued)

*Primary Examiner* — Claire Kaufman
(74) *Attorney, Agent, or Firm* — Kristin Konzak

(57) ABSTRACT

Anti-DR5 antibody agonists, combined with apoptosis-inducing agents, synergistically induce apoptosis in cancer cells.

17 Claims, 35 Drawing Sheets

OTHER PUBLICATIONS

Li et al., "LBY135, A Novel Anti-DR5 Agonistic Antibody Induces Tumor Cell-Specific Cytotoxic Activity in Human Colon Tumor Cell Lines and Xenografts," Drug Development Research, 2008 vol. 69 pp. 69-82.

Buchsbaum et al; "TRAIL-receptor antibodies as a potential cancer treatment"; Future Oncolo 3(4):405-409 (2007).

Camidge; "The Potential of Death Receptor 4- and 5-Directed Therapies in the Treatment of Lung Cancer"; Clinical Lung Cancer 8(7):413-419 (2007).

Clarke et al; "Reovirus-Induced Apoptosis is Mediated by TRAIL"; Journal of Virology 74(17):8135-8139, Sep. 2000.

Hymowitz et al; "Triggering Cell Death: The Crystal Structure of Apo2L/TRAIL in a Complex with Death Receptor 5"; Molecular Cell 4:565-571 (1999).

Imgenex Datasheet; "Polyclonal Antibody to DR5/Apo2/TRAIL-R2/TRAILR2/TRICK2/Killer" Downloaded Sep. 17, 2009 from http://www.imgenex.com/antibody_details.php?catalog=IMG-120A&id=.

Kabat et al; Identical V region amino acid sequences and segments of sequences in antibodies of different specificities. Relative contributions of VH and VL genes, minigenes, and complementarity-determining regions to binding of antibody-combining sites; Journal of Immunology 147:1709-1719 (1991).

Laguinge et al; "DR5 Receptor Mediates Anoikis in Human Colorectal Carcinoma Cell Lines"; Cancer Research 68 (3):909-917 (2008).

Li et al; "Antitumor efficacy of LBY135, an anti-DR5 monoclonal antibody, alone or in combination with chemotherapy in human colon tumor cell lines and xenografts"; Proc Ann Assoc Cancer Res 2007a, Abstract 4874; 98th AACR Annual Meeting, Apr. 14-18, Los Angeles CA (2007).

Natoni et al; "TRAIL signals to apoptosis in CLL cells primarily through TRAIL-R1 whereas cross-linked agaonistic TRAIL-R2 antibodies facilitate signalling via TRAIL-R2"; British Journal of Haematology 139(4):568-577 (2007).

Pan et al; "An Antagonist Decoy Receptor and a Death Domain-Containing Receptor for TRAIL"; Science 277:815-818 (1997).

Ren et al; "Differential Regulation of the TRAIL Death Receptors DR4 and DR5 by the Signal Recognition Particle"; Molecular Biology of the Cell 15:5064-5074 (2004).

Rottman et al; "A TRAIL receptor-dependent synthetic lethal relationship between MYC activation and GSK3beta/ FBW7 loss of function"; PNAS 102(42):15195-15200 (2005).

Sheridan et al; "Control of TRAIL-Induced Apoptosis by a Family of Signaling and Decoy Receptors"; Science 277:818-821 (1997).

Shigeno et al; "Interferon-alpha sensitizes human hepatoma cells to TRAIL-induced apoptosis through DR5 upregulation and NK-kappaB inactivation"; Oncogene 22:1653-1662 (2003).

Wagner et al; "Activation and Suppression of the TRAIL Death-Receptor Pathway in Chemotherapy Sensitive and Resistant Follicular Lymphoma Cells"; Cancer Biology & Therapy 2(5):534-540 (2003).

Wang et al; "Synthetic lethal targeting of MYC by activation of the DR5 death receptor pathway"; Cancer Cell 5:501-512 (2004).

Bowie, James U. et al.; "Deciphering the Message in Protein Sequences: Tolerance to Amino Acid Substitutions"; 1990, *Science*, vol. 247, pp. 1306-1310.

Chuntharapai, Anan et al.; "Isotype-Dependent Inhibition of Tumor Growth In Vivo by Monoclonal Antibodies to Death Receptor 4"; *The Journal of Immunology*, vol. 166, pp. 4891-4898, 2001.

Dong, Qiang G. et al; "The function of multiple IkB: NF-kB complexes in the resistance of cancer cells to Taxol-induced apoptosis"; 2002, *Oncogene*, vol. 21, pp. 6510-6519.

Gussow, Detlef et al.; "Humanization of Monoclonal Antibodies"; 1991, *Methods in Enzymology*, vol. 203, pp. 99-121.

Ichikawa, Kimihisa et al; "Tumoricidal activity of a novel nati-human DR5 monoclonal antibody without hepatocyte cytotoxicity"; 2001, *Nature Medicine*, vol. 7, No. 8, pp. 954-960.

Kipriyanov, Sergey M. et al.; "Generation of Recombinant Antibodies"; 1999, *Nature Biotechnology*, vol. 12, pp. 173-201.

Odoux, Christine et al.; "Trail, Fasl and a Blocking Anti-DR5 Antibody Augment Paclitaxel-Induced Apoptosis in Human Non-Small-Cell"; 2002, *Int. J. Cancer*, vol. 97, pp. 458-465.

Rudikoff, Stuart et al.; "Single amino acid substitution altering antigen-binding specificity"; 1982, *PNAS*, vol. 79, pp. 1979-1983.

* cited by examiner

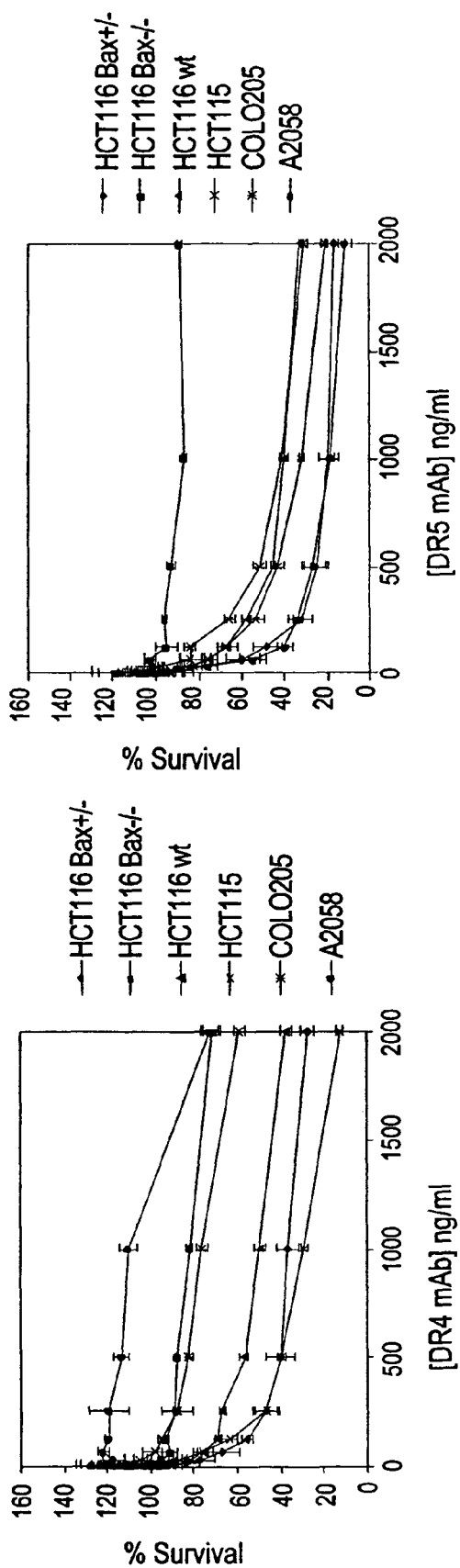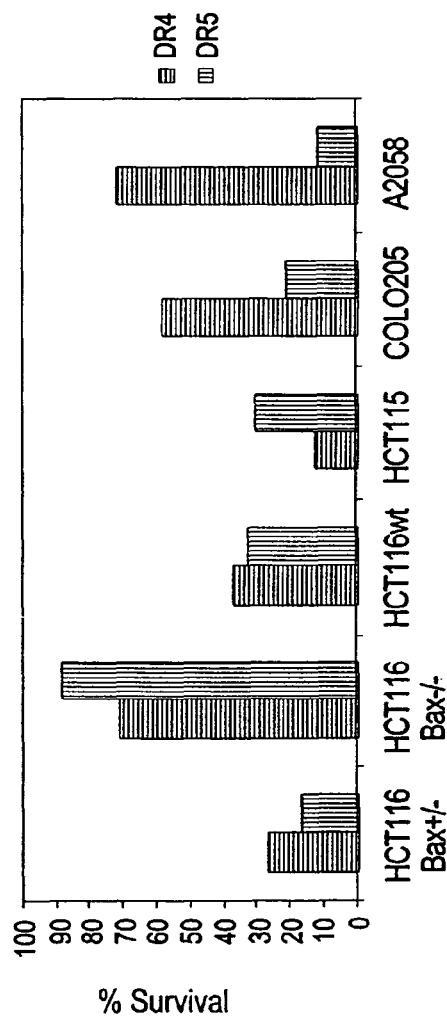
FIG. 5

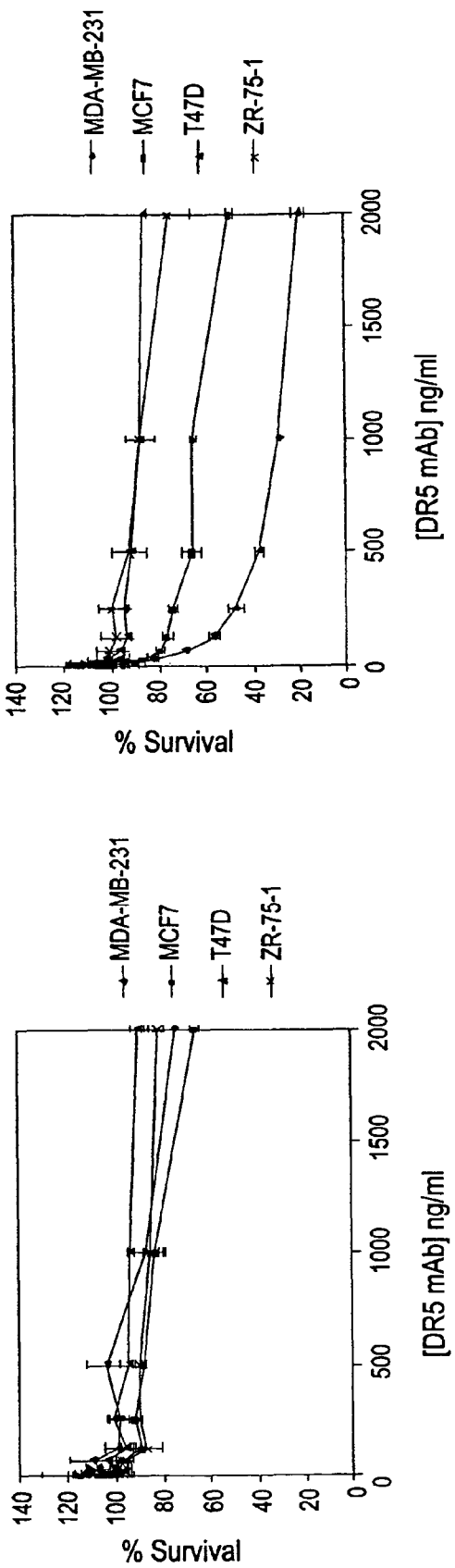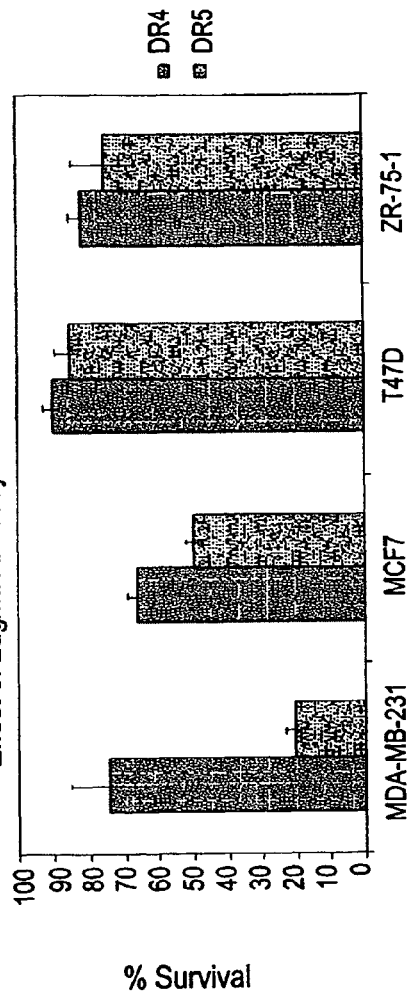
FIG. 6

Effect of LB672 On Normal And Tumor Cells

FIGURE 16. NFκB Activation By the Proteosome

Viruses, growth factors, radiation or chemotherapeutic drugs activate pathways that lead to the degradation of IκB by the proteosome. NFκB activates transcription of genes that protect the cell from apoptosis.

20S Proteosome Inhibitors – [Chymotryptic Activity]

| Compound | Description | Selectivity | IC50 | MTD | Sol. |
|---|---|---|---|---|---|
| NVP-AFB340-NX | Boronate | Good | <1nM | 3mg/kg-1x | Good |
| NVP-AFD314-NX | Boronate | Good | <1nM | 3mg/kg-1x | Good |
| NVP-AEV273-NX | Beta-Lactame | Excellent | 3nM | 20 mg/kg-2x | Poor |

NVP-AFB340-NX

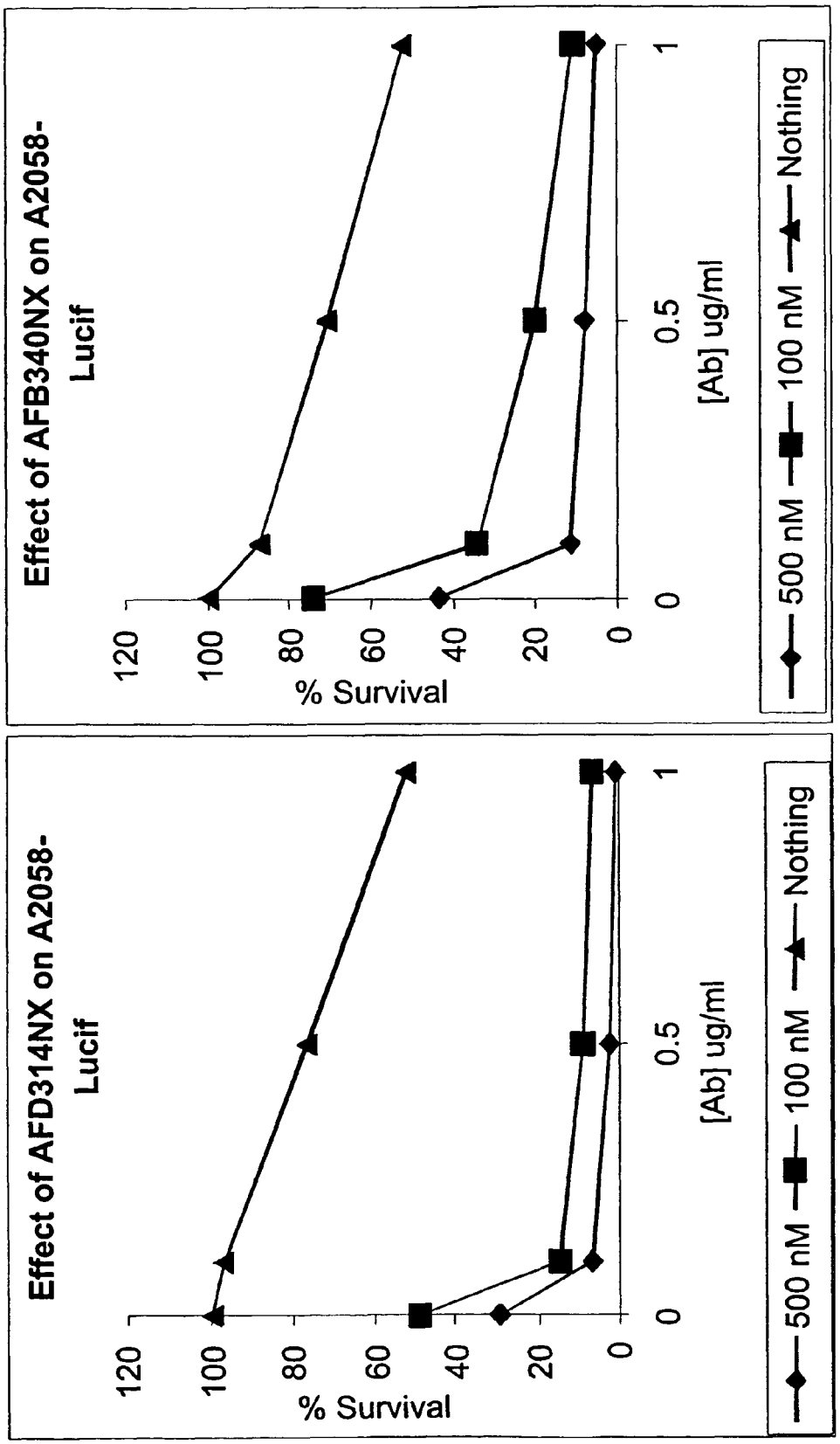
FIG. 19 Effect of Proteosome Inhibitors On A2058-Luc

Effect of Proteosome Inhibitors On The Hepatocarcinoma Cell Line HUH7-Luc   FIG. 20
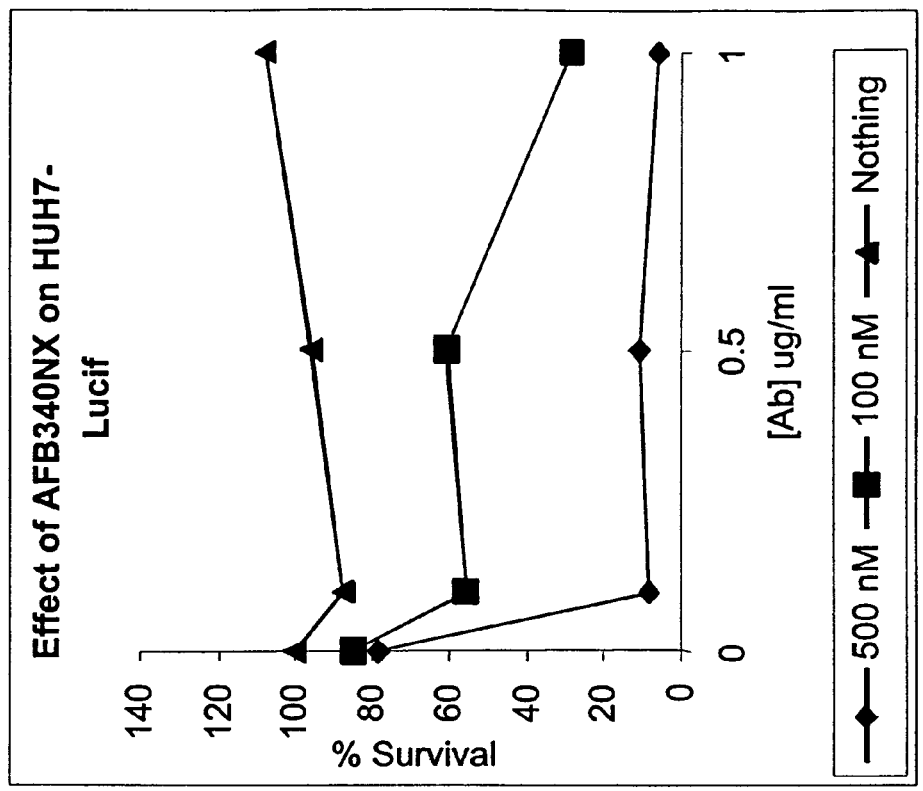
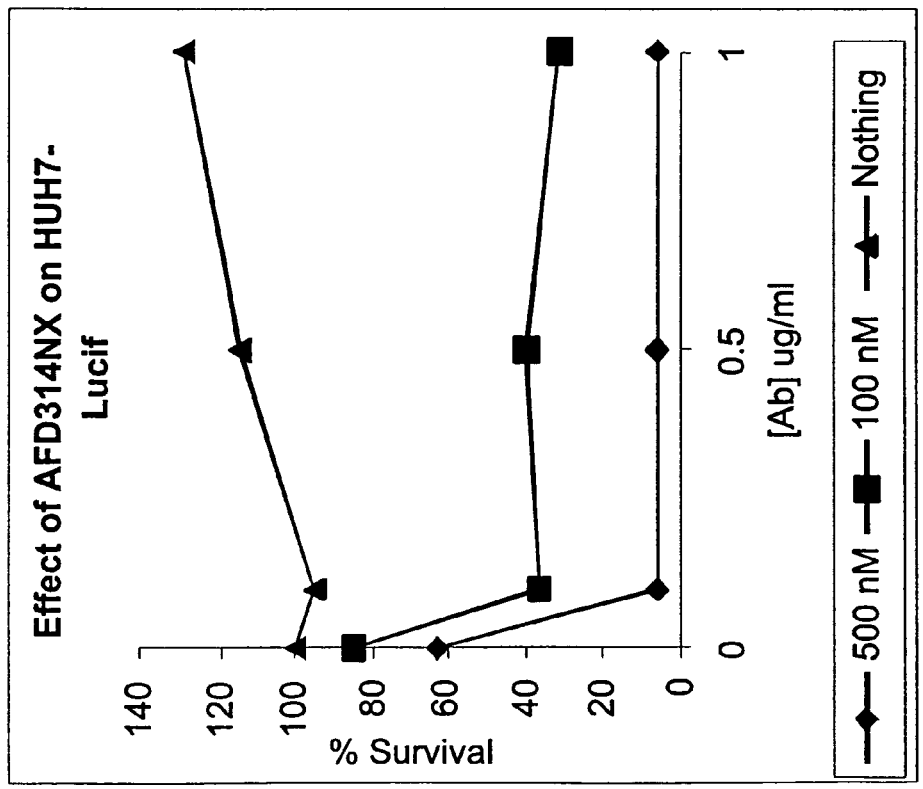

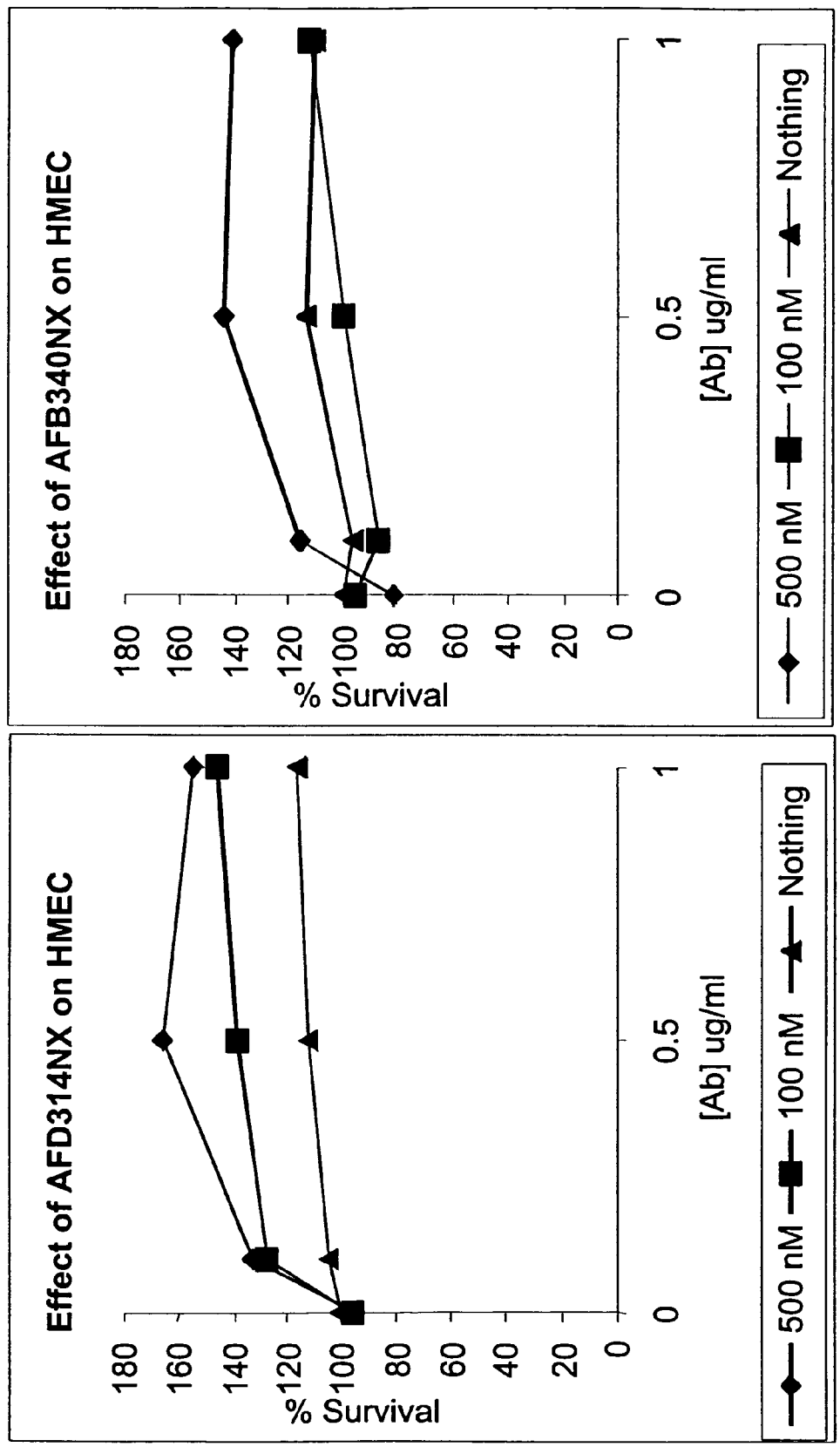
FIG. 21 Effect of Proteosome Inhibitors On Normal Human Mammary Epithelial Cells (HMEC)

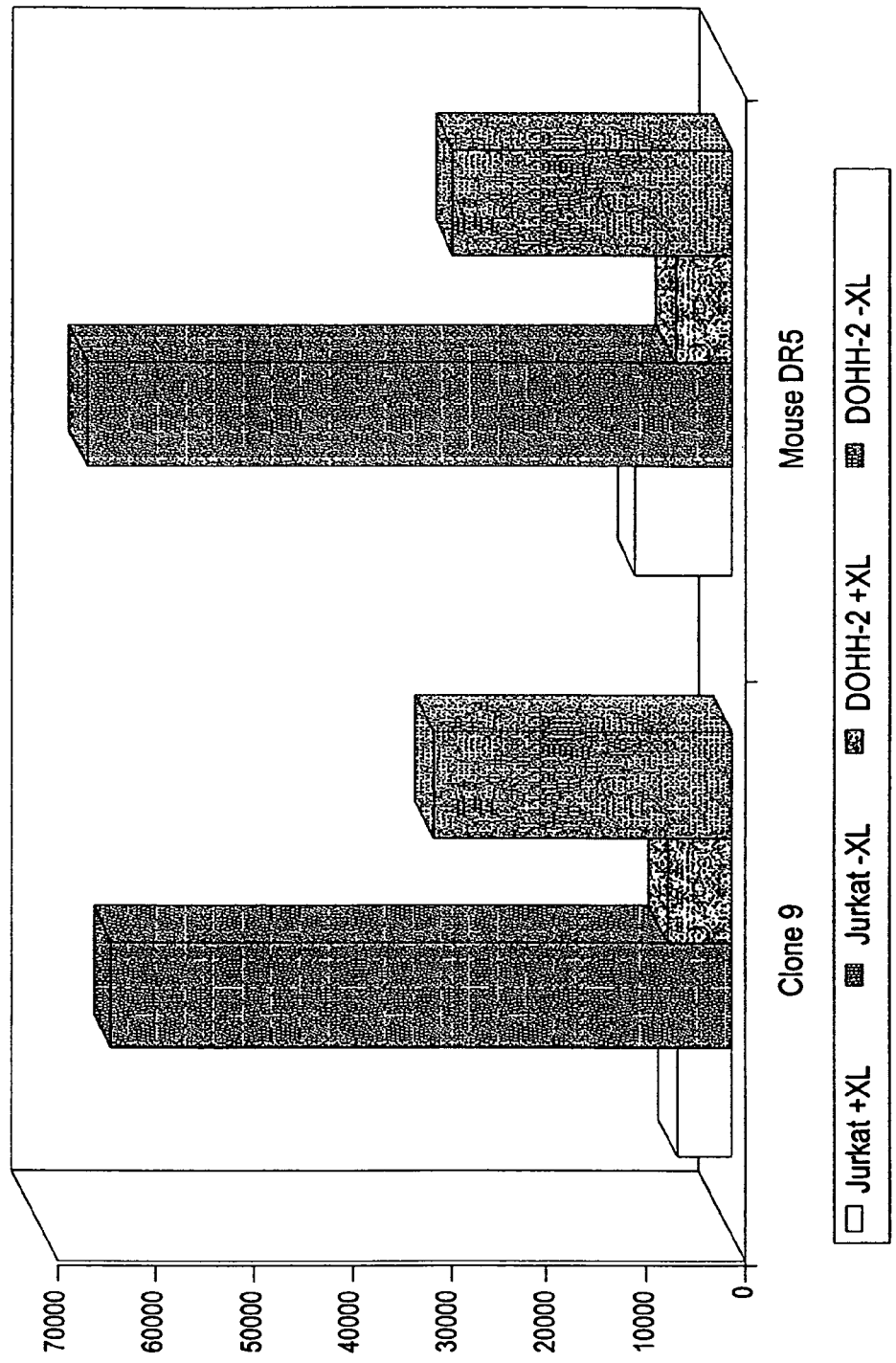

Anti-DR5 DNA Sequence

Light Chain Variable Region

GACATTGGGATGACCCAGTCTCCATCCATGTCTGCATCTGTCCACATTAGTGGGAGACAGGGTCA
GCATCACCTGCAAGGCCAGTCAGGATGTGAATACTGTATAGCCTGGTATCAACAAAA
ACCAGGGCAATCTCCTAAACTACTGATTTACTGGGCATCCACCGGCACACTGGAGTC
CCTGATCGCTTCACAGGCAGTGGATCTGGGACAGATTATACTCTCACCATCAGCAGTA
TGGAGGCTGAAGATCTGCCACTTATTACTGCCAGCAGTGGAGTAGTAACCCGCTCAC
GTTCGGTGCTGGGACCAAGCTGGAGCTGAAACGGGCTGATGCTGCACCAACTGTATCC
ATCTTCCCACC

Heavy Chain Variable Region

CAGGCAAAGGTCCAGTGCAGTCTGGAGCTGAGCTGGTGAAACCCGGGCATCA
GTGAAGCTGTCCTGCAAGGCTTCTGGCTACACCTTCACTGACTATACACTGGGT
AAAGCAGAGGTCTGGACAGGGTCTTGAGTGGATTGGGTTTACCCTGGAGGTGGT
TATATAAAATACAATGAGAAATTCAAGGACCAAGGCCACATTGACTGCGACAAATCCT
CCAACACACAGTCTATATGGAGCTTAGTCGATTGACATCTGAAGGCTCTGCGGTCTATTC
TGTGCAAGACACAGGAAGAGGGCATCTATTTGACTACTACTGGGGCCAAGGCACCACTCTCA
CAGTCTCCTCA

FIG. 23

DR5 $V_H$ Sequence – Heavy Chain Subgroup 2B

*FR1*
Lys Val Gln Leu Gln Gln Ser Gly Ala Glu Leu Val Lys Pro Gly Ala Ser Val
Lys Leu Ser Cys Lys Ala Ser Gly Tyr Thr Phe Thr Asp Tyr Thr Ile His Trp Val
*CDR1*
Lys Gln Arg Ser Gly Gln Gly Leu Glu Trp Ile Gly Trp Phe Tyr Pro Gly Gly
*FR2*
Gly Tyr Ile Lys Tyr Asn Glu Lys Phe Lys Asp Arg Ala Thr Leu Thr Ala Asp
*CDR2*
Lys Ser Ser Asn Thr Val Tyr Met Glu Leu Ser Arg Leu Thr Ser Glu Gly Ser
*FR3*
Ala Val Tyr Phe Cys Ala Arg His Glu Gly Ile Tyr Phe Asp Tyr Trp Gly
*CDR3*
Gln Gly Thr Thr Leu Thr Val Ser Ser
*FR4*

FIG. 24

DR5 $V_L$ Sequence– Kappa Light Chain Subgroup 5

*FR1*

Asp Ile Ala Met Thr Gln Ser His Lys Phe Met Ser Thr Leu Val Gly Asp

*CDR1*

Arg Val Ser Ile Thr Cys Lys Ala Ser Gln Asp Val Asn Thr Ala Ile Ala

*FR2*

Trp Tyr Gln Gln Lys Pro Gly Gln Ser Pro Lys Leu Leu Ile Tyr Trp Ala

*CDR2*

Ser Thr Arg His Thr Gly Val Pro Asp Arg Phe Thr Gly Ser Gly Ser Gly

*FR3*

Thr Asp Tyr Thr Leu Thr Ile Ser Ser Met Glu Ala Glu Asp Ala Ala Thr

*CDR3*

Tyr Tyr Cys Gln Gln Trp Ser Ser Asn Pro Leu Thr Phe Gly Ala Gly Thr

*FR4*

Lys Leu Glu Leu Lys Arg Ala

FIG. 25

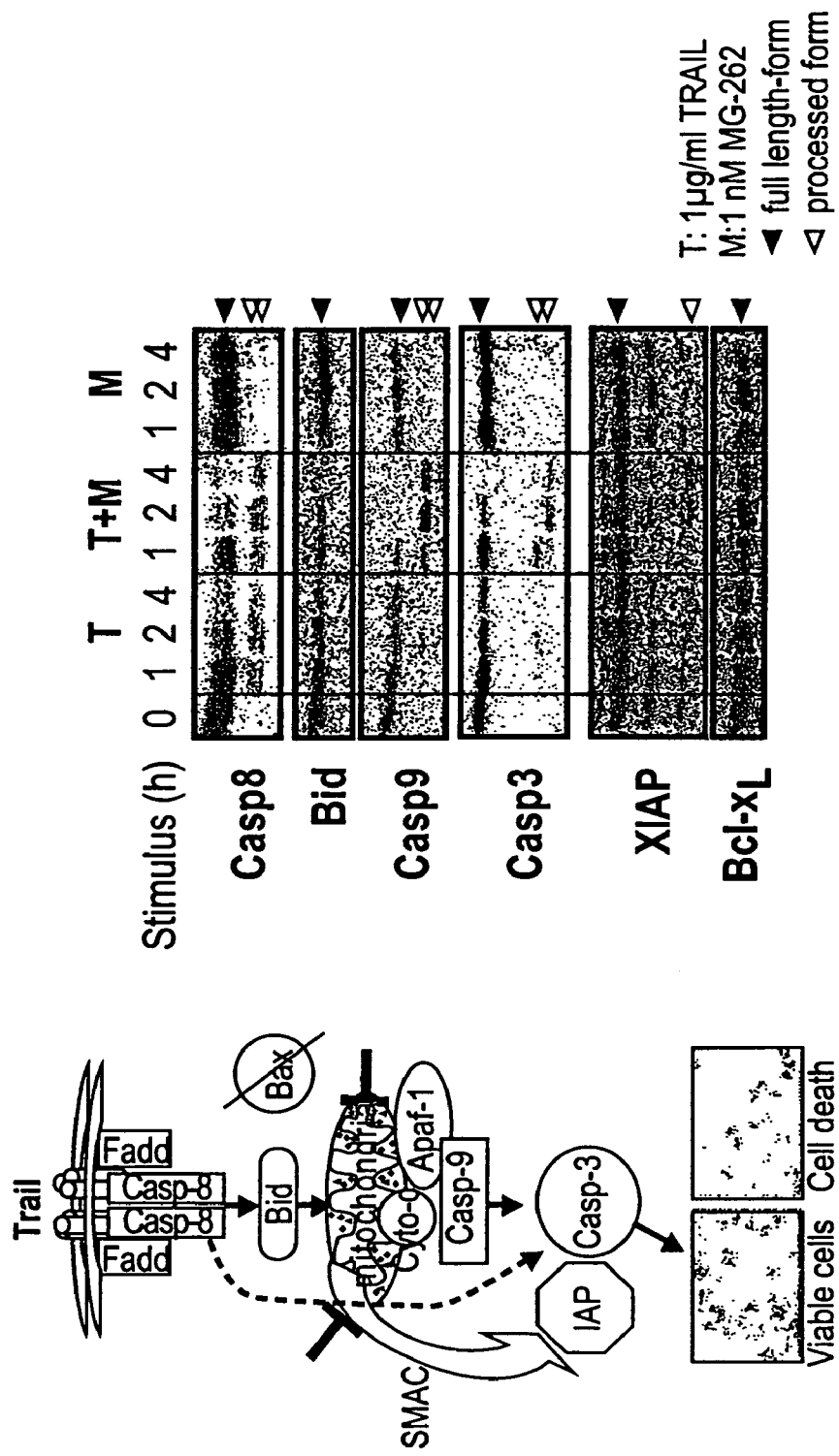

Sequence of DR5'A' heavy chain variable region
AAGGTCCAGCTGCAGCAGTCTGGAGCTGAGCTGGTGAAACCCGGGGCATCAGTGAA
GCTGTCCTGCAAGGCTTCTGGCTACACCTTCACTGACTATACATACACTGGGTAAA
GCAGAGGTCTGGACAGGGTCTTGAGTGGATTGGGTTTTACCCTGGAGGTGGTTA
TATAAATAACATGAGAAATTCAAGGACAAGGCCACATTGACTGCGGACAAATCCTC
CAACACAGTCTATATGGAGCTTAGTCGATTGACATCTGAAGACTCTGCGGTCTATTC
TGTGCAAGACACGAAGAGGGCATCTATTTGACTACTGGGGCCAAGGCACCACTCTC
ACAGTCTCCTCA Amino acid sequence of VH
KVQLQQSGAELVKPGASVKLSCKASGYTFTDYTIHWVKQRSGQGLEWIGWFYPGGGYIK
YNEKFKDRATLTADKSSNTVYMELSRLTSEDSAVYFCARHEEGIYFDYWGQGTTLTVSS DNA Sequence of DR5'A' light chain variable region
GACATTGTGATGACCCAGTCTCACAAGTTCATGTCCACATCAGTGGAGACAGGGTCA
GCATCACCTGCAAGGCCAGTCAGGATGTGAATACTGTATAGCCTGGTATCAACAAAA
ACCAGGGCAATCTCCTAAACTACTGATTTACTGGGCATCCACCCGGCACACTGGAGTC
CCTGATCGCTTCACAGGCAGTGGATCTGGGACAGATTATACTCTCACCATCAGCAGTGT
GCAGGCTGAAGACCTGGCACTTTATTACTGTCAGCAACATTATACCACTCCATTCACGT
TCGGCTCGGGGACAAAGTTG Amino acid sequence of VL
DIVMTQSHKFMSTSVGDRVSITCKASQDVNTAIAWYQQKPGQSPKLLIYWASTRHTGVPDR
FTGSGSGTDYTLTISSVQAEDLALYYCQQHYTTPFTFGSGTKL

FIG. 35

SEQUENCE LISTING

```
<160> NUMBER OF SEQ ID NOS: 15

<210> SEQ ID NO 1
<211> LENGTH: 64
<212> TYPE: PRT
<213> ORGANISM: Artificial Sequence
<220> FEATURE:
<223> OTHER INFORMATION: Description of Artificial Sequence:Baculovirus
      Inhibitory Repeat (BIR) region motif conserved
      residue consensus sequence
<220> FEATURE:
<221> NAME/KEY: MOD_RES
<222> LOCATION: (2)..(24)
<223> OTHER INFORMATION: Xaa = any amino acid, Xaa at positions 22-24
      may be present or absent
```

```
<220> FEATURE:
<221> NAME/KEY: MOD_RES
<222> LOCATION: (26)..(36)
<223> OTHER INFORMATION: Xaa = any amino acid
<220> FEATURE:
<221> NAME/KEY: MOD_RES
<222> LOCATION: (38)..(39)
<223> OTHER INFORMATION: Xaa = any amino acid
<220> FEATURE:
<221> NAME/KEY: MOD_RES
<222> LOCATION: (41)..(56)
<223> OTHER INFORMATION: Xaa = any amino acid
<220> FEATURE:
<221> NAME/KEY: MOD_RES
<222> LOCATION: (58)..(63)
<223> OTHER INFORMATION: Xaa = any amino acid

<400> SEQUENCE: 1

Arg Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Gly Xaa Xaa Xaa Xaa Xaa Xaa
             20                  25                  30

Xaa Xaa Xaa Xaa Cys Xaa Xaa Cys Xaa Xaa Xaa Xaa Xaa Xaa Xaa
         35                  40                  45

Xaa Xaa Xaa Xaa Xaa Xaa Xaa His Xaa Xaa Xaa Xaa Xaa Xaa Cys
     50                  55                  60

<210> SEQ ID NO 2
<211> LENGTH: 359
<212> TYPE: DNA
<213> ORGANISM: Artificial Sequence
<220> FEATURE:
<223> OTHER INFORMATION: Description of Artificial Sequence:anti-DR5
      Antibody A light chain variable region

<400> SEQUENCE: 2
gacattgcga tgacccagtc tcacaagttc atgtccacat tagtgggaga cagggtcagc      60
atcacctgca aggccagtca ggatgtgaat actgctatag cctggtatca acaaaaacca    120
gggcaatctc ctaaactact gatttactgg gcatccaccc ggcacactgg agtccctgat    180
cgcttcacag gcagtggatc tgggacagat tatactctca ccatcagcag tatggaggct    240
gaagatgctg ccacttatta ctgccagcag tggagtagta acccgctcac gttcggtgct    300
gggaccaagc tggagctgaa acgggctgat gctgcaccaa ctgtatccat cttcccacc     359

<210> SEQ ID NO 3
<211> LENGTH: 360
<212> TYPE: DNA
<213> ORGANISM: Artificial Sequence
<220> FEATURE:
<223> OTHER INFORMATION: Description of Artificial Sequence:anti-DR5
      Antibody A heavy chain variable region

<400> SEQUENCE: 3
caggcaaagg tccagctgca gcagtctgga gctgagctgg tgaaacccgg ggcatcagtg      60
aagctgtcct gcaaggcttc tggctacacc ttcactgact atactataca ctgggtaaag    120
cagaggtctg acagggtct tgagtggatt ggtggttttt accctggagg tggttatata     180
aaatacaatg agaaattcaa ggacagggcc acattgactg cggacaaatc ctccaacaca    240
gtctatatgg agcttagtcg attgacatct gaaggctctg cggtcatttt ctgtgcaaga    300
cacgaagagg gcatctattt tgactactgg ggccaaggca ccactctcac agtctcctca    360

<210> SEQ ID NO 4
<211> LENGTH: 118
```

```
<212> TYPE: PRT
<213> ORGANISM: Artificial Sequence
<220> FEATURE:
<223> OTHER INFORMATION: Description of Artificial Sequence:anti-DR5
      Antibody A heavy chain subgroup B variable region

<400> SEQUENCE: 4
```

Lys Val Gln Leu Gln Gln Ser Gly Ala Glu Leu Val Lys Pro Gly Ala
 1               5                  10                  15

Ser Val Lys Leu Ser Cys Lys Ala Ser Gly Tyr Thr Phe Thr Asp Tyr
            20                  25                  30

Thr Ile His Trp Val Lys Gln Arg Ser Gly Gln Gly Leu Glu Trp Ile
        35                  40                  45

Gly Trp Phe Tyr Pro Gly Gly Gly Tyr Ile Lys Tyr Asn Glu Lys Phe
    50                  55                  60

Lys Asp Arg Ala Thr Leu Thr Ala Asp Lys Ser Ser Asn Thr Val Tyr
65                  70                  75                  80

Met Glu Leu Ser Arg Leu Thr Ser Glu Gly Ser Ala Val Tyr Phe Cys
                85                  90                  95

Ala Arg His Glu Glu Gly Ile Tyr Phe Asp Tyr Trp Gly Gln Gly Thr
            100                 105                 110

Thr Leu Thr Val Ser Ser
        115

```
<210> SEQ ID NO 5
<211> LENGTH: 109
<212> TYPE: PRT
<213> ORGANISM: Artificial Sequence
<220> FEATURE:
<223> OTHER INFORMATION: Description of Artificial Sequence:anti-DR5
      Antibody A kappa light chain subgroup 5 variable
      region

<400> SEQUENCE: 5
```

Asp Ile Ala Met Thr Gln Ser His Lys Phe Met Ser Thr Leu Val Gly
 1               5                  10                  15

Asp Arg Val Ser Ile Thr Cys Lys Ala Ser Gln Asp Val Asn Thr Ala
            20                  25                  30

Ile Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Met Glu Ala
65                  70                  75                  80

Glu Asp Ala Ala Thr Tyr Tyr Cys Gln Gln Trp Ser Ser Asn Pro Leu
                85                  90                  95

Thr Phe Gly Ala Gly Thr Lys Leu Glu Leu Lys Arg Ala
            100                 105

```
<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:synthetic
      siRNA ttds(N)19TT
<220> FEATURE:
<221> NAME/KEY: modified_base
<222> LOCATION: (3)..(21)
<223> OTHER INFORMATION: n = any nucleotide

<400> SEQUENCE: 6
```

-continued

| ttnnnnnnnn nnnnnnnnnn ntt | 23 |

<210> SEQ ID NO 7
<211> LENGTH: 354
<212> TYPE: DNA
<213> ORGANISM: Artificial Sequence
<220> FEATURE:
<223> OTHER INFORMATION: Description of Artificial Sequence:alternate
      sequence for anti-DR5 Antibody A heavy chain
      variable region

<400> SEQUENCE: 7

| aaggtccagc tgcagcagtc tggagctgag ctggtgaaac ccggggcatc agtgaagctg | 60 |
| tcctgcaagg cttctggcta caccttcact gactatacta tacactgggt aaagcagagg | 120 |
| tctggacagg gtcttgagtg gattgggtgg ttttaccctg gaggtggtta tataaaatac | 180 |
| aatgagaaat tcaaggacag ggccacattg actgcggaca atcctccaa cacagtctat | 240 |
| atggagctta gtcgattgac atctgaagac tctgcggtct atttctgtgc aagacacgaa | 300 |
| gagggcatct attttgacta ctggggccaa ggcaccactc tcacagtctc ctca | 354 |

<210> SEQ ID NO 8
<211> LENGTH: 118
<212> TYPE: PRT
<213> ORGANISM: Artificial Sequence
<220> FEATURE:
<223> OTHER INFORMATION: Description of Artificial Sequence:alternate
      sequence for anti-DR5 Antibody A heavy chain
      variable region

<400> SEQUENCE: 8

Lys Val Gln Leu Gln Gln Ser Gly Ala Glu Leu Val Lys Pro Gly Ala
 1               5                   10                  15

Ser Val Lys Leu Ser Cys Lys Ala Ser Gly Tyr Thr Phe Thr Asp Tyr
             20                  25                  30

Thr Ile His Trp Val Lys Gln Arg Ser Gly Gln Gly Leu Glu Trp Ile
         35                  40                  45

Gly Trp Phe Tyr Pro Gly Gly Gly Tyr Ile Lys Tyr Asn Glu Lys Phe
     50                  55                  60

Lys Asp Arg Ala Thr Leu Thr Ala Asp Lys Ser Ser Asn Thr Val Tyr
 65                  70                  75                  80

Met Glu Leu Ser Arg Leu Thr Ser Glu Asp Ser Ala Val Tyr Phe Cys
                 85                  90                  95

Ala Arg His Glu Glu Gly Ile Tyr Phe Asp Tyr Trp Gly Gln Gly Thr
             100                 105                 110

Thr Leu Thr Val Ser Ser
         115

<210> SEQ ID NO 9
<211> LENGTH: 312
<212> TYPE: DNA
<213> ORGANISM: Artificial Sequence
<220> FEATURE:
<223> OTHER INFORMATION: Description of Artificial Sequence:alternate
      sequence for anti-DR5 Antibody A light chain
      variable region

<400> SEQUENCE: 9

| gacattgtga tgacccagtc tcacaagttc atgtccacat cagtgggaga cagggtcagc | 60 |
| atcacctgca aggccagtca ggatgtgaat actgctatag cctggtatca acaaaaacca | 120 |
| gggcaatctc ctaaactact gatttactgg gcatccaccc ggcacactgg agtccctgat | 180 |

```
cgcttcacag gcagtggatc tgggacagat tatactctca ccatcagcag tgtgcaggct    240
gaagacctgg cactttatta ctgtcagcaa cattatacca ctccattcac gttcggctcg    300
gggacaaagt tg                                                        312
```

<210> SEQ ID NO 10
<211> LENGTH: 104
<212> TYPE: PRT
<213> ORGANISM: Artificial Sequence
<220> FEATURE:
<223> OTHER INFORMATION: Description of Artificial Sequence:alternate
      sequence for anti-DR5 Antibody A light chain
      variable region

<400> SEQUENCE: 10

```
Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Asn Thr Ala
            20                  25                  30

Ile Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Thr Thr Pro Phe
                85                  90                  95

Thr Phe Gly Ser Gly Thr Lys Leu
            100
```

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:siPAK1-0
      siRNA directed against PAK1

<400> SEQUENCE: 11

```
agagctgcta cagcatcaa                                                  19
```

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence:siPAK1-1
      siRNA directed against PAK1

<400> SEQUENCE: 12

```
gacauccaac agccagaaa                                                  19
```

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence:siPAK1-2
      siRNA directed against PAK1

<400> SEQUENCE: 13

```
gagaaagagc ggccagaga                                                  19
```

<210> SEQ ID NO 14

```
<211> LENGTH: 19
<212> TYPE: RNA
<213> ORGANISM: Artificial Sequence
<220> FEATURE:
<223> OTHER INFORMATION: Description of Artificial Sequence:hPAK1-6
      siRNA directed against PAK1

<400> SEQUENCE: 14
uaccagcacu augauugga                                                      19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence:siPAK1-7
      siRNA directed against PAK1

<400> SEQUENCE: 15
ucuguauaca cacggucug                                                      19
```

METHODS AND COMPOSITIONS FOR INDUCING APOPTOSIS IN CANCER CELLS WITH AN ANTI-DR5 ANTIBODY

CROSS-REFERENCE TO RELATED PATENT APPLICATIONS

The present application is a divisional application of Ser. No. 10/723,383, filed Nov. 25, 2003 now U.S. Pat. No. 7,229,383, which claims benefit to the following four U.S. Provisional Patent Applications: 60/504,901, filed Sep. 22, 2003; 60/494,714, filed Aug. 12, 2003; 60/448,960, filed Feb. 21, 2003; and 60/429,842, filed Nov. 27, 2002, each of which are incorporated by reference in its entirety for all purposes.

BACKGROUND OF THE INVENTION

Apoptosis is a highly conserved cell suicide program essential for development and tissue homeostasis of all metazoan organisms. Changes to the apoptotic pathway that prevent or delay normal cell turnover can be just as important in the pathogenesis of diseases as are abnormalities in the regulation of the cell cycle. Like cell division, which is controlled through complex interactions between cell cycle regulatory proteins, apoptosis is similarly regulated under normal circumstances by the interaction of gene products that either prevent or induce cell death.

TNF-related apoptosis-inducing ligand (TRAIL, also referred to as Apo2L) is a member of the TNF cytokine family. Upon binding to DR4 or DR5, two members of the TNF receptor super family, TRAIL induces cell death by apoptosis. See, e.g., Pan et al., Science 277:815-8 (1997); Sheridan, et al., Science 277:818-21 3 (1997); Walczak et al, EMBO J. 16:5386-97 4 (1997). In vitro, TRAIL has been shown to kill tumor cells, but is relatively non-toxic to normal cells.

Additional therapies are needed to treat cancer. The present invention addresses this and other problems.

BRIEF SUMMARY OF THE INVENTION

The present invention provides methods of inducing apoptosis in a cancer cell. In some embodiments, the method comprises contacting the cell with (i.) an anti-DR4 or anti-DR5 affinity agent agonist; and (ii.) an apoptosis-inducing agent. In some embodiments, the agonist is an anti-DR-5 antibody. In some embodiments, the anti-DR5 antibody has the binding specificity of an antibody comprising a heavy chain variable region comprising the sequence displayed in FIG. 24 or FIG. 35 and a light chain variable region as displayed in FIG. 25 or FIG. 35. In some embodiments, the anti-DR5 antibody comprises a heavy chain variable region comprising the sequence displayed in FIG. 24 or FIG. 35 and a light chain variable region as displayed in FIG. 25 or FIG. 35. In some embodiments, the anti-DR5 antibody is Antibody A. In some embodiments, the agonist is an anti-DR4 antibody.

In some embodiments, the cell is contacted with an anti-DR4 antibody agonist and an anti-DR5 antibody agonist.

In some embodiments, the agonist is a humanized antibody. In some embodiments, the agonist is a single chain antibody.

In some embodiments, the agent prevents or reduces the expression of BCL-2 or UbcH10. In some embodiments, the agent prevents activation of NFκB. In some embodiments, the agent prevents degradation of IκB. In some embodiments, the agent is a proteasome inhibitor. In some embodiments, the proteasome inhibitor is selected from the group consisting of PS-341, MG-262 and MG-132.

In some embodiments, the agent is an inhibitor of an Inhibitor of Apoptosis (IAP) protein. In some embodiments, the inhibitor is SMAC or a SMAC mimetic.

In some embodiments, the agent is an inhibitor of a polypeptide selected from the group consisting of plexin B1 (PLXNB1), SET domain-containing protein 7 (SET7), mitogen-activated protein kinase kinase kinase 5 (MAP3K5), STE20-like kinase (JIK), MAP kinase-interacting serine/threonine kinase 1 (MKNK1), putative endoplasmic reticulum multispan transmembrane protein (RFT1), 5-kinase, type I, gamma (PIP5K1C), mitogen-activated protein kinase-activated protein kinase 2 (MAPKAPK2), mitogen-activated protein kinase kinase 5 (MAP2K5), cyclin-dependent kinase 6 (CDK6), activin A receptor type II-like 1 (ACVRL1), Gardner-Rasheed feline sarcoma viral (v-fgr) oncogene homolog (FGR), hypothetical protein FLJ21802 (FLJ21802), muscle, skeletal, receptor tyrosine kinase (MUSK), chromosome 20 open reading frame 88 (C20orf88), budding uninhibited by benzimidazoles 1 (yeast homolog) (BUB1), ribosomal protein S6 kinase, 90 kD, polypeptide 5 (RPS6KA5), v-yes-1 Yamaguchi sarcoma viral related oncogene homolog (LYN), mitogen-activated protein kinase 7 (MAPK7), and v-akt murine thymoma viral oncogene homolog 1 (AKT1).

In some embodiments, the agent is an activator of a polypeptide selected from the group consisting of signal recognition particle 72 kD (SRP72), Caspase-8, Bid, B lymphoid tyrosine kinase (BLK), gene product similar to Pyruvate kinase, M2 isozyme (LOC148283), glycogen synthase kinase 3 alpha (GSK3A), hypothetical protein FLJ32312 (FLJ32312), mitogen-activated protein kinase 10 (MAPK10), TCF4: transcription factor 4, v-abl Abelson murine leukemia viral oncogene homolog 2 (arg, Abelson-related gene) (ABL2), v-ros avian UR2 sarcoma virus oncogene homolog 1 (ROS1) and v-myc avian myelocytomatosis viral oncogene homolog.

In some embodiments, the cancer cell is a colon cancer cell or a pancreatic cancer cell.

In some embodiments, the agent is an antagonist of PAK1. In some embodiments, the agent is an antagonist of a polypeptide selected from the group consisting of UbcH10, nsurf, stk12, Ask1 and JIK. In some embodiments, the agent is an siRNA molecule.

The present invention also provides methods of inducing apoptosis in a cancer cell in an individual in need thereof. In some embodiments, the method comprises administering to the individual a therapeutically effective amount of (i.) an anti-DR4 or anti-DR5 affinity agent agonist; and (ii.) an apoptosis-inducing agent.

In some embodiments, the agonist and the agent are administered separately. In some embodiments, the agonist and the agent are administered as a mixture. In some embodiments, the agonist is an anti-DR-5 antibody. In some embodiments, the anti-DR5 antibody has the binding specificity of an antibody comprising a heavy chain variable region comprising the sequence displayed in FIG. 24 or FIG. 35 and a light chain variable region as displayed in FIG. 25 or FIG. 35. In some embodiments, the anti-DR5 antibody comprises a heavy chain variable region comprising the sequence displayed in FIG. 24 or FIG. 35 and a light chain variable region as displayed in FIG. 25 or FIG. 35. In some embodiments, the anti-DR5 antibody is Antibody A. In some embodiments, the agonist is an anti-DR4 antibody. In some embodiments, the cell is contacted with an anti-DR4 antibody agonist and an anti-DR5 antibody agonist.

In some embodiments, the agonist is a humanized antibody. In some embodiments, the agonist is a single chain antibody.

In some embodiments, the agent prevents or reduces the expression of BCL-2 or UbcH10. In some embodiments, the agent prevents activation of NFκB. In some embodiments, the agent prevents degradation of IκB. In some embodiments, the agent is a proteasome inhibitor. In some embodiments, the proteasome inhibitor is selected from the group consisting of PS-341, MG-262 and MG-132.

In some embodiments, the agent is an inhibitor of an Inhibitor of Apoptosis (IAP) protein. In some embodiments, the inhibitor is SMAC or a SMAC mimetic.

In some embodiments, the cancer cell is a colon cancer cell or a pancreatic cancer cell. In some embodiments, the agent is an antagonist of PAK1. In some embodiments, the agent is an antagonist of a polypeptide selected from the group consisting of UbcH10, nsurf, stk12, Ask1 and JIK. In some embodiments, the agent is an siRNA molecule.

The present invention also provides a physiological composition comprising a therapeutically effective amount of (i.) an anti-DR4 or anti-DR5 antibody agonist; and (ii.) an apoptosis-inducing agent. In some embodiments, the agonist is an anti-DR-5 antibody. In some embodiments, the anti-DR5 antibody has the binding specificity of an antibody comprising a heavy chain variable region comprising the sequence displayed in FIG. 24 or FIG. 35 and a light chain variable region as displayed in FIG. 25 or FIG. 35. In some embodiments, the anti-DR5 antibody comprises a heavy chain variable region comprising the sequence displayed in FIG. 24 or FIG. 35 and a light chain variable region as displayed in FIG. 25 or FIG. 35. In some embodiments, the anti-DR5 antibody is Antibody A. In some embodiments, the agonist is an anti-DR4 antibody. In some embodiments, the cell is contacted with an anti-DR4 antibody agonist and an anti-DR5 antibody agonist.

In some embodiments, the agonist is a humanized antibody. In some embodiments, the agonist is a single chain antibody. In some embodiments, the agent prevents or reduces the expression of BCL-2 or UbcH10. In some embodiments, the agent prevents activation of NFκB. In some embodiments, the agent prevents degradation of IκB. In some embodiments, the agent is a proteasome inhibitor. In some embodiments, the proteasome inhibitor is selected from the group consisting of PS-341, MG-262 and MG-132.

In some embodiments, the agent is an inhibitor of an Inhibitor of Apoptosis (IAP) protein. In some embodiments, the inhibitor is SMAC or a SMAC mimetic.

In some embodiments, the agent is an antagonist of PAK1. In some embodiments, the agent is an antagonist of a polypeptide selected from the group consisting of UbcH10, nsurf, stk12, Ask1 and JIK. In some embodiments, the agent is an siRNA molecule.

The present invention also provides affinity agents with the binding specificity of an antibody comprising a heavy chain variable region comprising the sequence displayed in FIG. 24 or FIG. 35 and a light chain variable region as displayed in FIG. 25 or FIG. 35. In some embodiments, the affinity agents are antibodies comprising a heavy chain variable region comprising the sequence displayed in FIG. 24 or FIG. 35 and a light chain variable region as displayed in FIG. 25 or FIG. 35.

The present invention also provides cells expressing an antibody comprising a heavy chain variable region comprising the sequence displayed in FIG. 24 or FIG. 35 and a light chain variable region as displayed in FIG. 25 or FIG. 35.

The present invention also provides methods of inducing apoptosis in a cancer cell comprising contacting the cell with an affinity agent with the binding specificity of an antibody comprising a heavy chain variable region comprising the sequence displayed in FIG. 24 or FIG. 35 and a light chain variable region as displayed in FIG. 25 or FIG. 35. In some embodiments, the agonist is an anti-DR-5 antibody. In some embodiments, the anti-DR5 antibody has the binding specificity of an antibody comprising a heavy chain variable region comprising the sequence displayed in FIG. 24 or FIG. 35 and a light chain variable region as displayed in FIG. 25 or FIG. 35. In some embodiments, the anti-DR5 antibody comprises a heavy chain variable region comprising the sequence displayed in FIG. 24 or FIG. 35 and a light chain variable region as displayed in FIG. 25 or FIG. 35. In some embodiments, the anti-DR5 antibody is Antibody A.

DEFINITIONS

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain is a C-terminal portion known as the J region. Within the variable region of the heavy chain, there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3, and FR4, respectively. The locations of CDR and FR regions and a numbering system have been defined by, e.g., Kabat et al. (Kabat et al., Sequences of Proteins of Immunological Interest, Fifth Edition, U.S. Department of Health and Human Services, U.S. Government Printing Office (1991)).

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see FUNDAMENTAL IMMUNOLOGY (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4:72 (1983); Cole et al., pp. 77-96 in *Monoclonal Antibodies and Cancer Therapy* (1985)). "Monoclonal" antibodies refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., *Proc. Natl. Acad. Sci. USA*, 81:6851-6855 (1984); Morrison and Oi, *Adv. Immunol.*, 44:65-92 (1988); Verhoeyen et al., *Science*, 239:1534-1536 (1988); Padlan, *Molec. Immun.*, 28:489-498 (1991); Padlan, *Molec. Immun.*, 31(3):169-217 (1994).

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. This selection may be achieved by subtracting out antibodies that cross-react with, e.g., DR5 molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

The terms "peptidomimetic" and "mimetic" refer to a synthetic chemical compound that has substantially the same structural and functional characteristics of a naturally or non-naturally occurring polypeptide (e.g., SMAC). Peptide analogs are commonly used in the pharmaceutical industry as non-peptide drugs with properties analogous to those of the template peptide. These types of non-peptide compound are termed "peptide mimetics" or "peptidomimetics" (Fauchere, J. *Adv. Drug Res.* 15:29 (1986); Veber and Freidinger *TINS* p. 392 (1985); and Evans et al. *J. Med. Chem.* 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as found in a polypeptide of interest, but have one or more peptide linkages optionally replaced by a linkage selected from the group consisting of, e.g., —CH$_2$NH—, —CH$_2$S—, —CH$_2$—CH$_2$—, —CH=CH— (cis and trans), —COCH$_2$—, —CH(OH)CH$_2$—, and —CH$_2$SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of carrying out at least one of the binding or enzymatic activities of a polypeptide of interest.

"siRNA" refers to small interfering RNAs, that are capable of causing interference and can cause post-transcriptional silencing of specific genes in cells, for example, mammalian cells (including human cells) and in the body, for example, mammalian bodies (including humans). The phenomenon of RNA interference is described and discussed in Bass, *Nature* 411: 428-29 (2001); Elbahir et al., *Nature* 411: 494-98 (2001); and Fire et al., *Nature* 391: 806-11 (1998); and WO 01/75164, where methods of making interfering RNA also are discussed. The siRNAs based upon the sequences and nucleic acids encoding the gene products disclosed herein typically have fewer than 100 base pairs and can be, e.g., about 30 bps or shorter, and can be made by approaches known in the art, including the use of complementary DNA strands or synthetic approaches. The siRNAs are capable of causing interference and can cause post-transcriptional silencing of specific genes in cells, for example, mammalian cells (including human cells) and in the body, for example, mammalian bodies (including humans). Exemplary siRNAs according to the invention could have up to 29 bps, 25 bps, 22 bps, 21 bps, 20 bps, 15 bps, 10 bps, 5 bps or any integer thereabout or therebetween. Tools for designing optimal inhibitory siRNAs include that available from DNAengine Inc. (Seattle, Wash.) and Ambion, Inc. (Austin, Tex.).

One RNAi technique employs genetic constructs within which sense and anti-sense sequences are placed in regions flanking an intron sequence in proper splicing orientation with donor and acceptor splicing sites. Alternatively, spacer sequences of various lengths may be employed to separate self-complementary regions of sequence in the construct. During processing of the gene construct transcript, intron sequences are spliced-out, allowing sense and anti-sense sequences, as well as splice junction sequences, to bind forming double-stranded RNA. Select ribonucleases then bind to and cleave the double-stranded RNA, thereby initiating the cascade of events leading to degradation of specific mRNA gene sequences, and silencing specific genes.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term "nucleic acid" encompasses the terms gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refer to compounds that have the same basic chemical structure as a naturally occurring amino acid, i.e., an alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, or designated region as measured using one of the following sequence comparison algorithms or by manual alignment and visual inspection. The invention provides polypeptides or polynucleotides that are substantially identical to the polypeptides or polynucleotides, respectively, exemplified herein (e.g., the CDRs exemplified in FIGS. 23-25). Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "affinity agent agonist" refers to an affinity agent (i.e., a molecule that specifically binds a target molecule) capable of activating a receptor to induce a full or partial receptor-mediated response. For example, an agonist of DR4 or DR5 binds to DR4 or DR5 and induces DR4 or DR5-mediated signaling. In some embodiments, a DR4 or DR5 affinity agent agonist can be identified by its ability to bind to DR4 or DR5 and induce apoptosis when contacted to Jurkat cells. An "antibody agonist" refers to the situation where the affinity agent is an antibody.

The term "apoptosis-inducing agent" refers to a compound that induces or promotes apoptosis in at least one cell type when contacted to the cell type. Exemplary apoptosis-inducing agents include, e.g., agonists or mimetics of the following: SMAC, Bax, Bik, Bok, Bim, Bak, Bid, Noxa, Puma, Hrk, or Bad; BH3, p53, TRAIL ligand, Fadd, Myc, and Mekk1, signal recognition particle 72 kD (SRP72), Caspase-8, Bid, B lymphoid tyrosine kinase (BLK), gene product similar to Pyruvate kinase, M2 isozyme (LOC148283), glycogen synthase kinase 3 alpha (GSK3A), hypothetical protein FLJ32312 (FLJ32312), mitogen-activated protein kinase 10 (MAPK10), TCF4: transcription factor 4, v-abl Abelson murine leukemia viral oncogene homolog 2 (arg, Abelson-related gene) (ABL2), v-ros avian UR2 sarcoma virus oncogene homolog 1 (ROS1) and v-myc avian myelocytomatosis viral oncogene homolog., as well as antagonists or inhibitors of the following: 26S Proteasome inhibitors, c-flip, NFκB pathway, IAP family members (e.g., XIAP, cIAP1, cIAP2, NAIP, MLIAP/Livin, survivin), proteasome pathway members (e.g., E1, E2 and E3); kinases PI3, Akt1, 2, and 3, Rip, Nik; CD40; Bcl2 family members (e.g., Bcl2, Bcl-x1, A1, Mcl1), ubiquitin conjugase UbcH 10, osteoprotegrin, plexin B1 (PLXNB1), SET domain-containing protein 7 (SET7), mitogen-activated protein kinase kinase kinase 5 (MAP3K5), STE20-like kinase (JIK), MAP kinase-interacting serine/threonine kinase 1 (MKNK1), putative endoplasmic reticulum multispan transmembrane protein (RFT1), 5-kinase, type I, gamma (PIP5K1C), mitogen-activated protein kinase-activated protein kinase 2 (MAPKAPK2), mitogen-activated protein kinase kinase 5 (MAP2K5), cyclin-dependent kinase 6 (CDK6), activin A receptor type II-like 1 (ACVRL1), Gardner-Rasheed feline sarcoma viral (v-fgr) oncogene homolog (FGR), hypothetical protein FLJ21802 (FLJ21802), muscle, skeletal, receptor tyrosine kinase (MUSK), chromosome 20 open reading frame 88 (C20orf88), budding uninhibited by benzimidazoles 1 (yeast homolog) (BUB1), ribosomal protein S6 kinase, 90 kD, polypeptide 5 (RPS6KA5), v-yes-1 Yamaguchi sarcoma viral related oncogene homolog (LYN), mitogen-activated protein kinase 7 (MAPK7), and v-akt murine thymoma viral oncogene homolog 1 (AKT1), PAK1 (including, e.g., any of the following P21 (CDKN1A)-activated kinase 1, PAKA, P65-PAK, P68-PAK, alpha-PAK, MUK2, PAK1B (p21 activated kinase 1B), P21/Cdc42/Rac1-activated kinase 1 (yeast Ste20-related), Cdc42/Rac effector kinase PAK-A, protein kinase MUK2), nsurf, stk12 (including, e.g., serine/threonine kinase 12, aurora-related kinase 2, aurora/IPL1-like kinase 2, AIK2, ARK2, AIM-1, and AIM1), apoptosis signal-regulating kinase 1 (Ask1), TLK1 (e.g., accession no. NM_012290), NLK (e.g., accession no. NM_016231), GRAF (e.g., accession no. NM_015071), GCK (e.g., accession no. NM_000162), ERK5 (e.g., accession no. NM_002749), FGR (e.g., accession no. NM_005248), ACVRL1 (e.g., accession no. NM_000020), MEKK5 (e.g., accession no. NM_002757), PIP5K1C (e.g., accession no. XM_047620), MAPKAPK2 (e.g., accession no. NM_004759), RFT1 (e.g., accession no. NM_052859), MKNK1 (e.g., accession no. NM_003684), PLXNB1 (e.g., accession no. NM_002673). Additional exemplary apoptosis-inducing agents include, e.g., agents that enhance DR5 and DR4 expression and/or stability, agents that enhance caspase activity or stability, and agents that induce or enhance a DNA damage response. Agonist or mimetics in the above list include the gene products themselves, e.g., p53 is a p53 agonist. Antagonists include agents that directly inhibit activity and agents that indirectly inhibit activity through decreasing expression or stability of target molecule mRNA (e.g., siRNAs) or protein.

An agent that "prevents or reduces the expression" of a protein refers to compounds that, e.g., bind to, partially or totally block stimulation, decrease, prevent, delay expression. Expression of a protein can be reduced by at least, e.g., 5%, 10%, 25%, 50%, 75%, 90%, 95% or 100%.

"Activation of NFκB" refers to induction of nuclear localization of NFκB, DNA binding by NFκB or transcription resulting from DNA binding by NFκB.

"Prevents degradation of IκB" refers to degradation of IκB by the proteasome, thereby releasing NFκB to enter the cell nucleus.

A "proteasome inhibitor" refers to an agent that inhibits the proteasome-ubiquitin pathway, thereby preventing degradation of IκB and subsequent nuclear localization of IkB's partner, NFκB. The proteasome includes, e.g., the 26S proteasome complex.

An "Inhibitor of Apoptosis (IAP) protein" refers to a polypeptide of the protein family that inhibits caspase activity. All but one of the known IAP proteins share a twofold or threefold repeat of a characteristic sequence motif, the Baculovirus Inhibitory Repeat (BIR; ~70 residues; survivin is a recently discovered human IAP that contains one BIR region). This BIR region contains a number of conserved residues, with the consensus sequence: R-X(20-23)-G-X (11)-C-X(2)-C-X(16)-H-X(6)-C (SEQ ID NO:1). Exemplary IAPs include, e.g., X chromosome linked inhibitor of apoptosis (XIAP; Genbank accession number U32974), the cellular IAP proteins (c-IAP-1/HIAP-2/hMIHB and c-IAP-2/HIAP-1/hMIHC; Liston et al., Nature 379:349-353 (1996); Rothe et al., Cell 83:1243-1252 (1995)); the neuronal apoptosis inhibitory protein (NAIP; Roy et al., Cell 80:167-178 (1995)); and survivin (Ambrosini et al., Nature Med. 3:917-921 (1997)). See, e.g., U.S. Patent Application Nos. 2002/0132786 and 2002/0009757 as well as U.S. Pat. No. 6,187,557.

"SMAC" refers to a mitochondrial polypeptide, which is released together with cytochrome c from the mitochondria in response to apoptotic stimuli. SMAC promotes caspase activation by binding and neutralizing the IAPs. See, e.g., Du et al., Cell 102:33-42 (2000); Verhagen et al., Cell 102:43-53 (2000).

"Modulators" are used herein to refer to molecules that inhibit or enhance the activity of expression a gene product. "Antagonists" or "inhibitors" are compounds that, e.g., inhibit expression of a gene product or bind to, partially or totally block stimulation, decrease, prevent, delay activation, inactivate, desensitize, or down regulate the activity of the gene product or that bind or down regulate a receptor to which the gene product binds. "Agonists" or "activators" are compounds that, e.g., induce or activate the expression of a gene product or bind to, stimulate, increase, open, activate, facilitate, enhance activation, sensitize or up regulate the activity of the gene product or that bind or up regulate a receptor to which the gene product binds. Agonists or antagonists can include, e.g., antibodies, organic small molecules (e.g., less than 1500 Daltons), genetically modified versions of the gene products themselves, etc. Antagonists include, e.g., siRNA molecules for reducing expression of a transcript encoding a gene product.

BRIEF DESCRIPTION OF THE DRAWINGS

FIG. 5 illustrates the effect of DR4/DR5 functional antibodies on colon and melanoma cancer cell lines.
FIG. 6 illustrates the effect of DR4/DR5 functional antibodies on breast cancer cell lines.

FIG. 19 illustrates the effect of proteasome inhibitors on A2058.

FIG. 20 illustrates the effect of proteasome inhibitors on a hepatocarcinoma cell line.

FIG. 21 illustrates the effect of proteasome inhibitors on normal mammary cells.

FIG. 22 illustrates the expression of mouse-human chimeric DR5 antibodies.

FIG. 23 illustrates the nucleotide sequences for the heavy (SEQ ID NO:3) and light (SEQ ID NO:2) variable regions of Antibody A.

FIG. 24 illustrates the heavy chain variable region for Antibody A (SEQ ID NO:4).

FIG. 25 illustrates the light chain variable region for Antibody A (SEQ ID NO:5).

FIG. 34 illustrates the effect the proteasome inhibitor MG-262 on the expression of various mitochondrial apoptosis pathway proteins.

FIG. 35 illustrates an alternate sequences for the heavy chain (SEQ ID NOS:7 and 8) and light chain (SEQ ID NOS:9 and 10) variable region for Antibody A.

DETAILED DESCRIPTION OF THE INVENTION

I. Introduction

Figure 1:
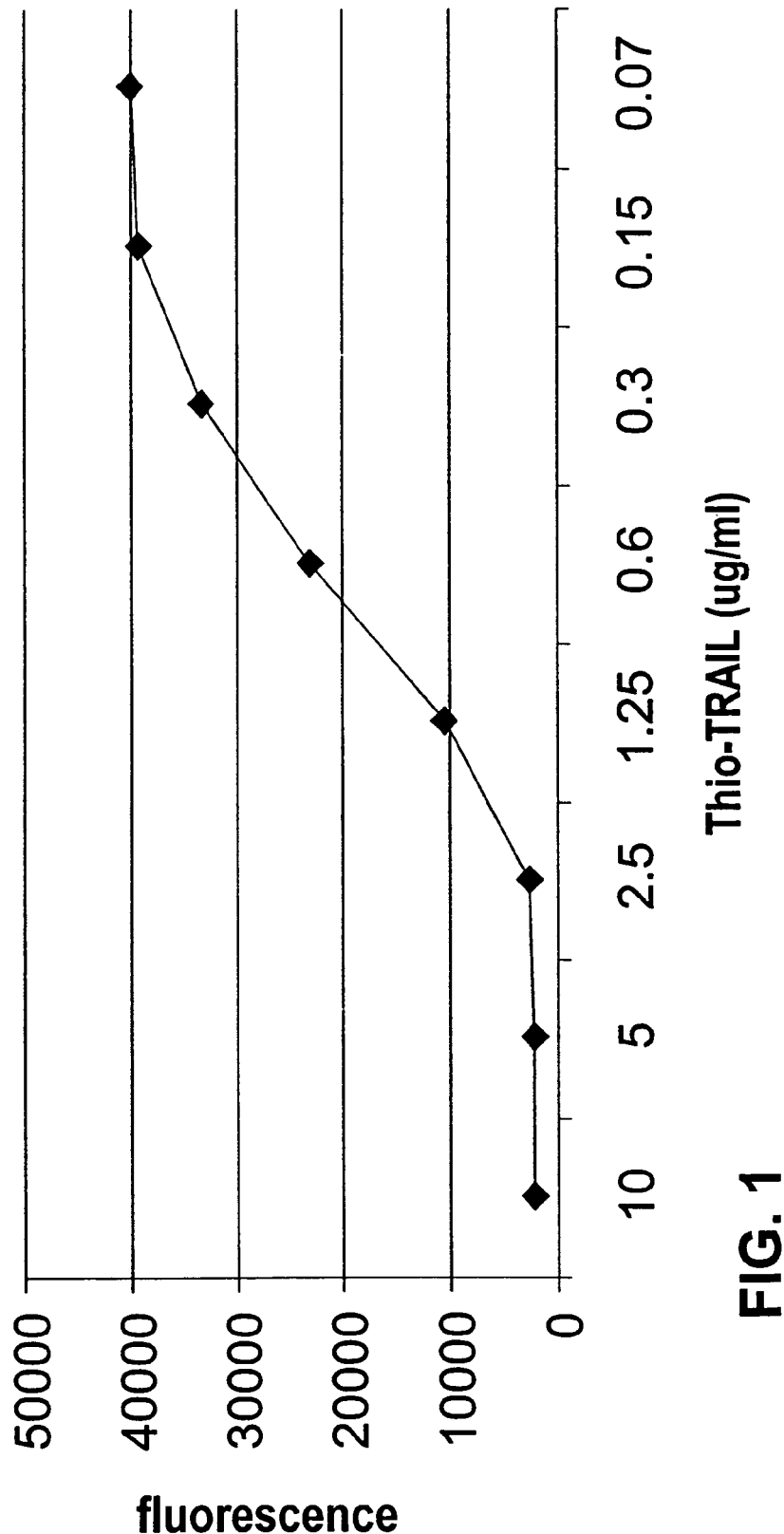
FIG. 1 displays TRAIL induced apoptosis in Jurkat cells.

The present invention demonstrates the surprising result that anti-DR4 or anti-DR5 antibody agonists administered with an apoptosis-inducing agent induces apoptosis in cancer cells in a synergistic fashion. Thus cancer cells that are resistant to treatment by one of these components alone will likely be killed when contacted by an anti-DR4 or anti-DR5 agonist antibody and a second apoptosis-inducing agent. In addition, of those cells that would go through apoptosis upon contact with one of the above-listed components, contact with anti-DR4 or anti-DR5 agonist antibody and an apoptosis-inducing protein will lead to a faster induction of apoptosis.

The present invention also provides high potency DR5 agonist antibodies and their use to induce apoptosis in cancer cells.

II. Anti-DR4 or DR5 Antibodies

1. Introduction

Any anti-DR4 or anti-DR5 antibody agonist can be used according to the methods of the invention. DR4 (also referred to as Death Receptor 4) and DR5 (also referred to as Death Receptor 5) are two receptors of the ligand TRAIL. See, e.g., Pan et al., *Science* 277:815-8 (1997); Sheridan, et al., *Science* 277:818-21 3 (1997); Walczak et al, *EMBO J.* 16:5386-97 4 (1997). Anti-DR5 antibodies have been described previously in, e.g., PCT WO 01/83560 (antibody TRA-8; ATCC PTA-1428) and PCT WO 02/079377. In addition, anti-DR5 antibody agonists are described herein. The variable regions of the heavy and light chains of an exemplary anti-DR5 antibody agonist are provided in FIGS. 23-25. In some embodiments, the anti-DR5 antibodies compete with the exemplified antibody for binding to DR5. In some embodiments, the DR5 antibody agonists have CDRs that are substantially similar to the CDRs exemplified in FIGS. 24, 25 or both.

Any type of antibody agonist may be used according to the methods of the invention. Generally, the antibodies used are monoclonal antibodies. Monoclonal antibodies can be generated by any method known in the art (e.g., using hybridomas, recombinant expression and/or phage display).

The antibodies of the invention need not be cross-linked or otherwise treated prior to administration. However, in some embodiments, the antibodies of the invention are cross-linked. Cross-linking (e.g., using hetero- or homo-bifunctional chemical cross-linkers) is well known in the art. Alternatively, stable multivalent Fabs (e.g., trimers or tetramers, etc.) can be administered. See, e.g., PCT WO 99/27964.

Exemplary anti-DR5 antibodies include those with the specificity of an antibody comprising the light and heavy chain variable region sequences displayed in FIGS. 24 and 25. In some embodiments, the antibody is Antibody A.

In numerous embodiments, the anti-DR5 antibodies of the invention do not bind to other polypeptides. In some embodiments, the ant-DR5 antibodies do not bind any other receptor in the TNF receptor family (e.g., TNFR2, TNFR3, OX40, CD40, FAS, DcR3, CD27, CD30, CD137, DR4, DcR1, DcR2, RANK, OPG, DR3, TR2, NGFR, TNFR1, and TAC1). In some embodiments, the ant-DR5 antibodies do not bind to DR4, DTR1, DTR2 or OPG.

The anti-DR4 or anti-DR5 antibodies of the invention can be extremely potent. For example, in some embodiments, in a standard subcutaneous tumor ablation assay, the antibodies of the invention can reduce tumor size by 50% at a concentration of 1 or less mg/kg body weight (and in some embodiments, 0.50 mg/kg, 0.05 mg/kg, or 0.01 mg/kg or less) when administered to an animal 3 times a week for two weeks and ablates tumors completely when ten times that amount is used.

In some cases, the anti-DR4 or anti-DR5 antibodies of the invention are designed to lack or have a reduced antibody-dependent cellular cytotoxicity (ADCC). For example, in some embodiments, the antibodies of the invention comprise an IgG-1, IgG-2, IgG-2A, IgG 3 or IgG-4 Fc region.

A number of different synthetic molecular scaffolds can be used to display the variable light and heavy chain sequences displayed in FIGS. 24 and 25. A publication describing use of the fibronectin type III domain (FN3) as a specific molecular scaffold on which to display peptides including CDRS is Koide, A. et al. *J. Mol. Biol* 284:1141-1151(1988). Other scaffolding alternatives include, e.g., "minibodies" (Pessi, A. et al., *Nature* 362:367-369 (1993)), tendamistat (McConnell, S. J. and Hoess, R. H. *J. Mol. Biol.* 250:460-470 (1995)), and "camelized" VH domain (Davies J. and Riechmann, L. *BiolTechnology* 13:475-479 (1995)). Other scaffolds that are not based on the immunoglobulin like folded structure are reviewed in Nygren, P. A. and Uhlen, M. Curr. *Opin. Struct. Biol.* 7:463-469 (1997). U.S. Pat. No. 6,153,380 describes additional scaffolds. The term "affinity agents" encompasses molecules comprising synthetic molecular scaffolds such as those described above to display binding domains with a binding specificity for DR4 or DR5, including the specificities described for antibodies described herein.

2. Humanized Antibodies

In some embodiments, the antibody used according to the present invention is a chimeric (e.g., mouse/human) antibody made up of regions from a non-human anti-DR4 or anti-DR5 antibody agonist together with regions of human antibodies. For example, a chimeric H chain can comprise the antigen binding region of the heavy chain variable region (e.g., the sequence displayed in FIG. 24 or FIG. 35) of the non-human antibody linked to at least a portion of a human heavy chain constant region. This humanized or chimeric heavy chain may be combined with a chimeric L chain that comprises the antigen binding region of the light chain variable region (e.g., the sequence displayed in FIG. 25 or FIG. 35) of the non-human antibody linked to at least a portion of the human light chain constant region. In some embodiments, the heavy chain constant region can be an IgM or IgA antibody.

The chimeric antibodies of the invention may be monovalent, divalent, or polyvalent immunoglobulins. For example, a monovalent chimeric antibody is a dimer (HL) formed by a chimeric H chain associated through disulfide bridges with a chimeric L chain, as noted above. A divalent chimeric antibody is a tetramer ($H_2 L_2$) formed by two HL dimers associated through at least one disulfide bridge. A polyvalent chimeric antibody is based on an aggregation of chains.

The nucleotide and amino acid sequences of the variable region of an exemplary anti-DR5 antibody agonist are provided in FIGS. 22-24. The DNA sequences of the antibodies of the invention can be identified, isolated, cloned, and transferred to a prokaryotic or eukaryotic cell for expression by procedures well-known in the art. Such procedures are generally described in Sambrook et al., supra, as well as CURRENT PROTOCOLS IN MOLECULAR BIOLOGY (Ausubel et al., eds., 1989). Expression vectors and host cells suitable for expression of recombinant antibodies and humanized antibodies in particular, are well known in the art. The following references are representative of methods and vectors suitable for expression of recombinant immunoglobulins which may be utilized in carrying out the present invention: Weidle et al., *Gene*, 51: 21-29 (1987); Dorai et al., *J. Immunol.*, 13(12):4232-4241 (1987); De Waele et al., *Eur. J. Biochem.*, 176:287-295 (1988); Colcher et al., *Cancer Res.*, 49:1738-1745 (1989); Wood et al., *J. Immunol.*, 145(a):3011-3016 (1990); Bulens et al., *Eur. J. Biochem.*, 195:235-242 (1991); Beggington et al., *Biol. Technology*, 10: 169 (1992); King et al., *Biochem. J.*, 281:317-323 (1992); Page et al., *Biol. Technology*, 2:64 (1991); King et al., *Biochem. J.*, 290:723-729 (1993); Chaudary et al., *Nature*, 339:394-397 (1989); Jones et al., *Nature*, 321:522-525 (1986); Morrison and Oi, *Adv. Immunol.*, 44:65-92 (1988); Benhar et al., *Proc. Natl. Acad. Sci. USA*, 91:12051-12055 (1994); Singer et al., *J. Immunol.*, 150:2844-2857 (1993); Cooto et al., *Hybridoma*, 13(3):215-219 (1994); Queen et al., *Proc. Natl. Acad. Sci. USA*, 86:10029-10033 (1989); Caron et al., *Cancer Res.*, 32:6761-6767 (1992); Cotoma et al., *J. Immunol. Meth.*, 152:89-109 (1992). Moreover, vectors suitable for expression of recombinant antibodies are commercially available.

Host cells capable of expressing functional immunoglobulins include, e.g., mammalian cells such as Chinese Hamster Ovary (CHO) cells; COS cells; myeloma cells, such as NSO and SP2/O cells; bacteria such as *Escherichia coli*; yeast cells such as *Saccharomyces cerevisiae*; and other host cells.

3. Single Chain Antibodies

In some embodiments, the antibodies of the invention are single chain antibodies. Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *Proc. Natl. Acad. Sci. USA* 90:7995-7999 (1993); and Skerra etal., *Science* 240:1038-1040 (1988).

4. Human Antibodies

In some embodiments, human antibodies are used according to the present invention. Human antibodies can be made by a variety of methods known in the art including by using phage display methods using antibody libraries derived from human immunoglobulin sequences. See, e.g., Lonberg and Huszar, *Int. Rev. Immunol.* 13:65-93 (1995), U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

In some embodiments, the antibodies of the present invention are generated using phage display. For example, functional antibody domains are displayed on the surface of phage particles that carry the polynucleotide sequences encoding them. Such phage can be utilized to display antigen-binding domains expressed from a repertoire or combinatorial antibody library (e.g., human or murine). Phage expressing an antigen binding domain that binds DR4 or DR5 can be selected or identified with DR4 or DR5, e.g., using labeled DR4 or DR5. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

5. Generating Agonist Antibodies

Agonist antibodies can be identified by generating anti-DR4 or anti-DR5 antibodies and then testing each antibody for the ability trigger DR4 or DR5 mediated events, e.g., inducing apoptosis in a cancer cell. A variety of assays known in the art can be used to detect induction of apoptosis.

In one assay, DOHH-2 or Jurkat cells are contacted with a candidate antibody agonist and then monitored for viability as a function of antibody concentration. Reduced cell viability (e.g., caused by increased apoptosis) with increased antibody concentration indicates that the antibody is an agonist.

Cell viability can be assayed by adding Alamar blue, which fluoresces in the presence of living, but not dead, cells. As described in the Examples, agonist antibodies can be identified by screening hybridomas raised against DR4 or DR5 and then screening the hybridoma supernatant for the ability to induce apoptosis in DOHH-2 or Jurkat cells. Appropriate positive and negative controls can be used to confirm the results. For example, a cell line that does not go through DR4 or DR5-mediated TRAIL induced apoptosis should not go through apoptosis in response to a candidate anti-DR4 or anti-DR5 agonist.

III. Apoptosis-inducing Agents

The present invention provides for the synergistic effect of anti-DR4 or anti-DR5 affinity agent agonists with a second apoptosis-inducing agent. Apoptosis-inducing agents include any agent that induces apoptosis in cells. In some embodiments, the apoptosis-inducing agent preferentially induces apoptosis in cancer cells compared to non-cancer cells. Typically the apoptosis-inducing agents are agonists or activators of apoptosis or antagonists of inhibitors of apoptosis.

Exemplary apoptosis-inducing agents include, e.g., agonists or mimetics of the following: SMAC, Bax, Bik, Bok, Bim, Bak, Bid, Noxa, Puma, Hrk, or Bad; BH3, p53, TRAIL ligand, Fadd, Myc, and Mekk1, signal recognition particle 72 kD (SRP72), Caspase-8, Bid, B lymphoid tyrosine kinase (BLK), gene product similar to Pyruvate kinase, M2 isozyme (LOC148283), glycogen synthase kinase 3 alpha (GSK3A), hypothetical protein FLJ32312 (FLJ32312), mitogen-activated protein kinase 10 (MAPK10), TCF4: transcription factor 4, v-abl Abelson murine leukemia viral oncogene homolog 2 (arg, Abelson-related gene) (ABL2), v-ros avian UR2 sarcoma virus oncogene homolog 1 (ROS1) and v-myc avian myelocytomatosis viral oncogene homolog., as well as antagonists or inhibitors of the following: 26S Proteasome inhibitors, c-flip, NFκB pathway, IAP family members (e.g., XIAP, cIAP1, cIAP2, NAIP, MLIAP/Livin, survivin), proteasome pathway members (e.g., E1, E2 and E3); kinases PI3, Akt1, 2, and 3, Rip, Nik; CD40; Bcl2 family members (e.g., Bcl2, Bcl-x1, A1, Mcl1), ubiquitin conjugase UbcH10 (polynucleotide sequences encoding variants of human UbcH10 include, e.g., accession nos. NM_181803, NM_181802, NM_181801, NM_181800, NM_181799, NM_007019, and BC050736), osteoprotegrin, plexin B1 (PLXNB1), SET domain-containing protein 7 (SET7), mitogen-activated protein kinase kinase kinase 5 (MAP3K5), STE20-like kinase (JIK), MAP kinase-interacting serine/threonine kinase 1 (MKNK1), putative endoplasmic reticulum multispan transmembrane protein (RFT1), 5-kinase, type I, gamma (PIP5K1C), mitogen-activated protein kinase-activated protein kinase 2 (MAPKAPK2), mitogen-activated protein kinase kinase 5 (MAP2K5), cyclin-dependent kinase 6 (CDK6), activin A receptor type II-like 1 (ACVRL1), Gardner-Rasheed feline sarcoma viral (v-fgr) oncogene homolog (FGR), hypothetical protein FLJ21802 (FLJ21802), muscle, skeletal, receptor tyrosine kinase (MUSK), chromosome 20 open reading frame 88 (C20orf88), budding uninhibited by benzimidazoles 1(yeast homolog) (BUB1), ribosomal protein S6 kinase, 90 kD, polypeptide 5 (RPS6KA5), v-yes-1 Yamaguchi sarcoma viral related oncogene homolog (LYN), mitogen-activated protein kinase 7 (MAPK7), and v-akt murine thymoma viral oncogene homolog 1 (AKT1), PAK1 (including, e.g., any of the following P21(CDKN1A)-activated kinase 1, PAKA, P65-PAK, P68-PAK, alpha-PAK, MUK2, PAK1B (p21 activated kinase 1B), P21/Cdc42/Rac1-activated kinase 1 (yeast Ste20-related), Cdc42/Rac effector kinase PAK-A, protein kinase MUK2), nsurf, stk12 (including, e.g., serine/threonine kinase 12, aurora-related kinase 2, aurora/IPL1-like kinase 2, AIK2, ARK2, AIM-1, and AIM1), apoptosis signal-regulating kinase 1 (Ask1), TLK1 (e.g., accession no. NM_012290), NLK (e.g., accession no. NM_016231), GRAF (e.g., accession no. NM_015071), GCK (e.g., accession no. NM_000162), ERK5 (e.g., accession no. NM_002749), FGR (e.g., accession no. NM_005248), ACVRL1 (e.g., accession no. NM_000020), MEKK5 (e.g., accession no. NM_002757), PIP5K1C (e.g., accession no. XM_047620), MAPKAPK2 (e.g., accession no. NM_004759), RFT1 (e.g., accession no. NM_052859), MKNK1(e.g., accession no. NM_003684), PLXNB 1 (e.g., accession no. NM_002673). Additional exemplary apoptosis-inducing agents include, e.g., agents that enhance DR5 and DR4 expression and/or stability, agents that enhance caspase activity or stability, and agents that induce or enhance a DNA damage response. Agonist or mimetics in the above list include the gene products themselves (e.g., p53 is a p53 agonist), as well as agonist antibodies. Antagonists include agents that directly inhibit activity (e.g., antagonist antibodies) and agents that indirectly inhibit activity through decreasing expression or stability of target molecule mRNA (e.g., siRNAs) or protein.

Apoptosis-inducing agents that can be identified by targeting these gene products include compounds of various chemical natures. For example, modulators of these gene products can be screened with libraries of polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, structural analogs or combinations thereof.

Figure 27:
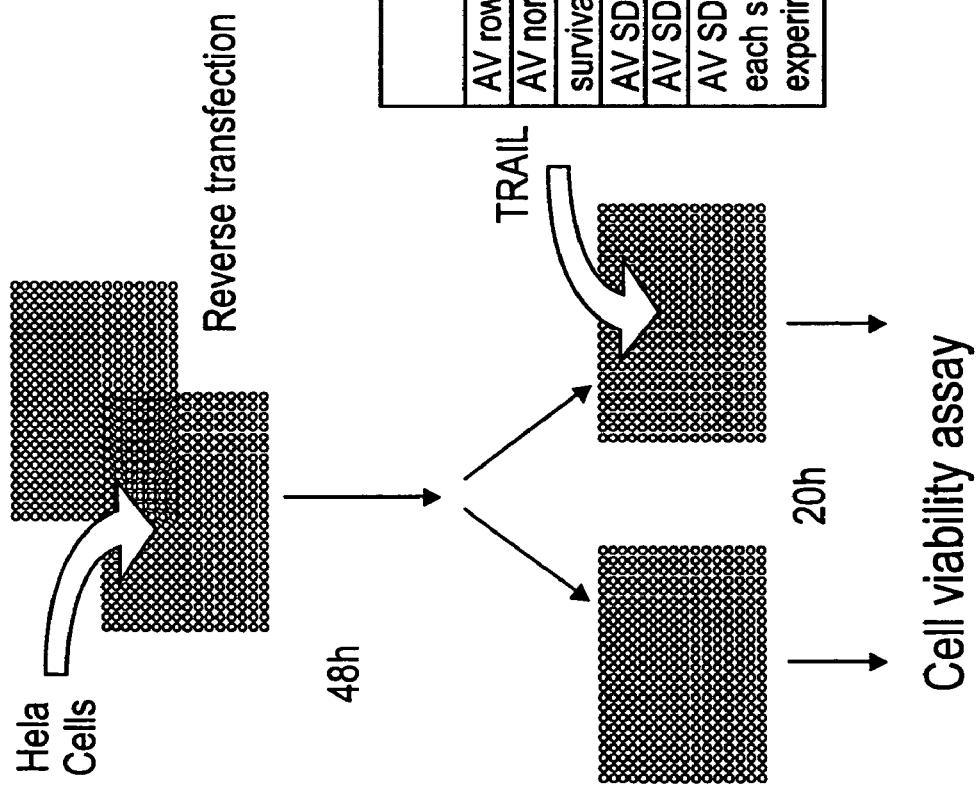
FIG. 27 also illustrates a screening methodology for identifying gene products that mediate TRAIL-induced apoptosis by introducing siRNAs to knockout specific gene expression in a cell-based assay.

In some embodiments, the apoptosis-inducing agent is a polynucleotide. For example, it can be an siRNA targeting a gene that inhibits TRAIL-induced apoptosis (e.g., UbcH10 or molecules listed in the first portion of FIG. 27). In some embodiments, the apoptosis-inducing agent is a small molecule compound (e.g., a molecule with a molecular weight of less than 1500 Daltons and in some cases, less than 1000 Daltons). For example, the apoptosis-inducing agent can be a small molecule compound that inhibits expression or activity of a gene product that inhibit TRAIL-induced apoptosis (e.g., UbcH10 or molecules listed in the first portion of FIG. 27). The apoptosis-inducing agent can also be a small molecule compound that enhanced expression or activity of a gene product that promote TRAIL-induced apoptosis (e.g., UbcH10 or molecules listed in the bottom portion of FIG. 27). Methods for screening modulators (including small molecule modulators) of a gene and its encoded polypeptide, and methods for preparing siRNA or other inhibitory polynucleotides of a known gene are all well known in the art. See, e.g., U.S. Pat. Nos. 6,573,099 and 6,506,559; *Principles and Practice of High Throughput Screening*, K. Murray (Ed.), CRC Press (2003); *High Throughput Screening: Methods and Protocols*, W. Janzen (Ed.), Humana Press (2002); PCT publications WO 95/35503, WO 95/30642, and WO 91/18980; Schultz et al, *Bioorg Med Chem Lett* 8:2409-2414, 1998; and Weller et al., *Mol Divers.* 3:61-70, 1997. Additional methods that can be employed for screening modulators of these genes and their products are disclosed in, e.g., Sambrook et al., *Molecular Cloning: A Laboratory Manual*, Cold Spring Harbor Press, N.Y., 3$^{rd}$ Ed. (2000); and Ausubel et al., *Current Protocols in Molecular Biology*, John Wiley & Sons, Inc., New York (1999).

In some embodiments, the apoptosis-inducing agent is conjugated to the anti-DR4 or anti-DR5 antibody agonist. In other embodiments, the apoptosis-inducing agent is not conjugated to the anti-DR4 or anti-DR5 antibody agonist.

In some embodiments, the apoptosis-inducing agent is not TNF-alpha, TNF-beta, AIM I, AIM II, Fas Ligand, or VEGI.

1. SMAC

In some embodiments, the apoptosis-inducing agent is SMAC/Diablo or a SMAC mimetic or agonist. SMAC/Diablo promotes caspase activity by binding Inhibitor of Apoptosis Proteins (IAPs). See, e.g., Du et al., *Cell* 102:33-42 (2000); Verhagen et al., *Cell* 102:43-53, 2000; U.S. Patent Application No. 2002/0110851. Administration or expression of SMAC in cells is encompassed by the present invention. SMAC fragments, such as the N-terminal peptides of SMAC (e.g., the N-termninal tetra or heptapeptides (Guo et al., *Blood* 99(9):3419-3426 (2002); Srinivasula et al., *J. Biol. Chem.* 275:36152-36157 (2000)), can also be expressed or administered. See, also, U.S. Patent Application 2002/0132786.

In addition, SMAC mimetic compounds can also be used according to the present invention. These compounds can have useful pharmaceutical properties and as such can be more efficient for administration with anti-DR4 or anti-DR5 antibodies. Exemplary SMAC mimetics include, e.g., peptides comprising a tetrapeptide that binds the surface groove within the BIR domain of an IAP, including tetrapeptides of the formula $X_1X_2X_3X4$, wherein $X_1$ is A, $X_2$ is V, T, or I, $X_3$ is P or A and X4 is F, Y, I or V or other SMAC peptides, agonists or peptidiomimetics described in PCT WO 02/26775. Other exemplary SMAC mimetics include LBP672. See, e.g., FIG. 15 and Example 54.

2. 26S Proteasome Inhibitors

In some embodiments, the apoptosis-inducing agent is a 26S Proteasome inhibitor. Proteasome inhibitors are agents that inhibit the proteasome-ubiquitin pathway, thereby preventing degradation of IκB and subsequent nuclear localization of IκB's partner, NFκB. The proteasome has two functional components: the 20S core catalytic subunit and the 19S regulatory subunit. The 20S and 19S subunits form a 26S complex that degrades proteins targeted for degradation with the addition of ubiquitin. Exemplary proteasome inhibitors include, e.g., PS-341 (NSC no. 681239, also known as bortezomib) and analogs thereof (see, e.g., Adams, *Cur. Opin. Chem Biol.* 6:493-500 (2002)). PS-341 and other proteasome inhibitors useful according to the methods of the present invention are described in U.S. Pat. No. 5,780,454, incorporated herein by reference.

Additional exemplary proteasome inhibitors include, e.g., lactacystin, PS-273 (NSC no. 681226); PS-293 (NSC no. 681227); PS-296 (NSC no. 681228); PS-303 (NSC no. 681229); PS-305 (NSC no. 681231); PS-313 (NSC no. 681234); PS-321 (NSC no. 681236); PS-334 (NSC no. 681237); PS-364 (NSC no. 681242); PS-325 (NSC no. 683086); PS-352 (NSC no. 683094); PS-383 (NSC no. 683098), YU101 (ac-hFLFL-epoxide) (see, e.g., Elofsson, et al., *Chem. Biol.* 6:811-822 (1999)), MG262, MG132, MG115, PSI (proteasome inhibitor N-benzyloxycarbonyl-Ile-Glu(O-tert-butyl)-Ala-leucinal). Assays for identifying proteasome inhibitors are commercially available from, e.g., Discoverx (Fremont, Calif.).

While combination of 26S proteasome inhibitors with DR4 or DR5 agonists (e.g., anti-DR4 or anti-DR5 antibodies of the present invention) can be an effective therapy for a wide range of hyperproliferative disorders, the combination can be particularly effective against cancer cells with defects in Bax or other components of the mitochondrial apoptosis pathway (e.g., Bcl-x1 or Bcl-2). For example, colon cancer patients frequently have tumor cells that are Bax defective. Therefore, proteasome inhibitor combined with a DR4 or DR-5 antagonist is particularly effective to treat colon cancers involving Bax or other mitochondrial apoptosis defects.

In some embodiments, the proteasome inhibitor is a compound of formula I

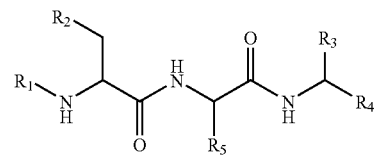

wherein $R_1$ is unsubstituted or substituted aryl; arylalkylcarbonyl, wherein the aryl moiety is unsubstituted or substituted; unsubstituted or substituted heterocyclyl; or heterocyclylalkylcarbonyl, wherein the heterocyclyl moiety is unsubstituted or substituted;

$R_2$ is unsubstituted or substituted aryl or unsubstituted or substituted heteroaryl;

$R_3$ is hydrogen, unsubstituted or substituted aryl or alkyl which is unsubstituted or substituted by unsubstituted or substituted cycloalkyl, unsubstituted or substituted aryl, or unsubstituted or substituted heteroaryl comprising at least one nitrogen atom;

$R_4$ is a moiety of the formula IA,

wherein $A_1$ and $A_2$ are hydroxy or substituted hydroxy, or together with the binding boron atom and the two binding oxygen atoms form a ring of the formula IA*,

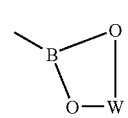

wherein W is alkylene, substituted alkylene, unsubstituted or substituted cycloalkylene, unsubstituted or substituted bicycloalkylene or unsubstituted or substituted tricycloalkylene;

and $R_5$ is unsubstituted or substituted alkyl, unsubstituted or substituted aryl, unsubstituted or substituted heterocyclyl, or unsubstituted or substituted cycloalkyl; or salts thereof.

Within the context of formula I, the general terms used have the following meanings:

Aryl preferably has a ring system of not more than 20 carbon atoms, especially not more than 12 carbon atoms, is preferably mono-, bi- or tric-cyclic, and is unsubstituted or substituted, preferably in each case unsubstituted or substituted phenyl or (especially 1- or 2-)naphthyl, one or more substituents preferably being independently selected from the group consisting of an aliphatic radical; free, etherified or esterified hydroxy; free or esterified carboxy; formyl; alkanoyl; unsubstituted, mono- or di-substituted amino; mercapto; sulfo; alkyl-thio; carbamoyl; N-alkyl-carbamoyl; N,N-di-alkyl-carbamoyl; phenyl; naphthyl; heterocyclyl, especially pyridyl; cyano and nitro, more preferably being selected from alkyl, e.g. methyl, ethyl or propyl; alkoxy, e.g. methoxy or ethoxy; di-substituted amino, e.g. dimethylamino; halogen, e.g. chloro or bromo; halogen-alkyl, e.g. trifluoromethyl; and phenyl, (especially 1- or 2-)-naphthyl, and heterocyclyl, especially as defined below, especially pyridyl, e.g. 3-, 4- or especially 2-pyridyl, each of which is unsubstituted or substituted with one or more, especially up to three, substituents, especially independently selected from the other aryl substituents just mentioned. Aryl $R_1$ is more preferably biphenylyl, especially 2-, 4- or preferably 3-biphenylyl, pyridylphenyl, especially 4-, 3- or most especially 2-pyridyl-(2-, 4- or preferably 3-)phenyl, or lower alkyl-phenyl, especially propyl-phenyl, such as 2-, 4- or especially 3-isopropylphenyl. Arylalkylcarbonyl $R_1$ (with unsubstituted or preferably substituted aryl) is preferably aryl-lower alkylcarbonyl with aryl as defined above, more preferably phenyl-lower alkyloxy-phenyl-lower alkylcarbonyl, especially 2-, 4- or preferably 3-benzyloxy-phenyl-acetyl or -propionyl, pyridyl-lower alkyloxyphenyl-lower alkylcarbonyl, especially 2-, 4- or preferably 3-(pyridin-2-, -4- or preferably -3-)-acetyl or -propionyl, or phenyl-lower alkylcarbonyl, especially phenyl-2- or preferably 3-phenyl-propionyl or phenylacetyl, wherein phenyl is unsubstituted or substituted by up to three substituents independently selected from lower alkoxy, especially methoxy, halogen, especially fluoro or chloro, or halogen-lower alkyl, such as trifluoromethyl. Unsubstituted or substituted aryl $R_2$ or (independently) $R_3$ is preferably mono-, di- or trisubstituted phenyl, especially substituted by up to four substituents independently selected from the substituents mentioned for aryl, especially from hydroxy, lower alkoxy (most preferred), preferably methoxy, halogen, preferably fluoro or chloro, and halogen-lower alkyl, preferably trifluoromethyl, especially phenyl substituted by up to three lower alkoxy, preferably methoxy, substituents, or in case of $R_3$ unsubstituted phenyl, or further unsubstituted or substituted napthyl, especially 1- or 2-naphthyl that is unsubstituted or substituted by up to four substituents independently selected from the substituents mentioned for aryl, especially from hydroxy, lower alkoxy (most preferred), preferably methoxy, halogen, preferably fluoro or chloro, and halogen-lower alkyl, preferably trifluoromethyl.

Unsubstituted heterocyclyl is preferably a heterocyclic radical that is unsaturated, saturated or partially saturated in the bonding ring and is preferably monocyclic or in a broader sense bicyclic or tricyclic ring; has 3 to 24, more preferably 4 to 16 ring atoms; wherein at least in the ring bonding to the radical of the molecule of formula I one or more, preferably one to four, especially one or two carbon atoms of a corresponding aryl radical are substituted by a heteroatom selected from the group consisting of nitrogen, oxygen and sulfur, the bonding ring preferably having 4 to 12, especially 5 to 7 ring atoms; heteroaryl being unsubstituted or substituted by one or more, especially 1 to 3, substituents independently selected from the group consisting of the substituents defined above as substituents of substituted aryl; and especially being a heteroaryl radical selected from the group consisting of imidazolyl, thienyl, furyl, tetrahydrofuryl, pyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazolidinyl, pyranyol, thiazolyl, isothiazolyl, oxazolyl, isoxazolyl, pyridyl, pyrazinyl, pyrimidinyl, piperidyl, piperazinyl, pyridazinyl, morpholinyl, thiomorpholinyl, indolizinyl, isoindolyl, 3H-indolyl, indolyl, indazolyl, triazolyl, tetrazolyl, purinyl, 4H-quinolizinyl, isoquinolyl, quinolyl, tetrahydroquinolyl, tetrahydroisoqionolyl, decahydroquinolyl, octahydroisoquinolyl, benzofuranyl, benzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, isochromanyl and chromanyl, each of these radicals being unsubstituted or substituted by one to two radicals selected from the group consisting of lower alkyl, especially methyl or tert-butyl, lower alkoxy, especially methoxy, and halo, especially bromo or chloro; pyridyl, especially 2- or 3-pyridyl, or indolyl is especially preferred, in a broader aspect lower alkyl-pyridyl, pyrimidinyl or lower alkylpyrimidinyl, halo-lower alkylpyridyl, lower alkoxy-pyridyl, di-lower alkyl-pyridyl, or halo-pyridyl. Heterocyclyl is unsubstituted or substituted by one or more, preferably up to three, substitutents independently selected from those mentioned above for aryl (where heterocyclyl as substituent of heterocyclyl carries no further heterocyclyl substituent other than pyridyl or indolyl) and from aryl as defined above, especially phenyl, especially those mentioned as being preferred. Unsubstituted heterocyclyl is preferred.

In heterocyclylalkylcarbonyl $R_1$, the heterocyclyl moiety is preferably substituted or especially unsubstituted heterocyclyl as mentioned above; preferred is substituted or preferably unsubstituted heterocyclyl-lower alkyl, especially with terminal substituted or preferably unsubstituted heterocyclyl, with heterocyclyl as described above; preferred is pyridyl-lower alkylcarbonyl, such as -acetyl or -propionyl.

As $R_1$, unsubstituted or substituted aryl or substituted aryl-lower alkylcarbonyl is preferred.

Heteroaryl $R_2$ is preferably unsubstituted or substituted heteroaryl as mentioned above, especially indolyl that is unsubstituted or substituted by one or more, especially up to three, substitutents independently selected from those mentioned above for substituted aryl, especially from hydroxy, lower alkoxy (most preferred), preferably methoxy, halogen, preferably fluoro or chloro, and halogen-lower alkyl, preferably trifluoromethyl.

$R_2$ is preferably substituted aryl.

An aliphatic radical preferably has up to 12 carbon atoms, preferably up to 7 carbon atoms, most preferably up to 4 carbon atoms, and is an aliphatic hydrocarbon radical, such as an unsubstituted or substituted alkynyl, alkenyl or preferably alkyl radical, more preferably lower alkyl, especially methyl, ethyl, n-propyl, iso-propyl, n-butyl, sec-butyl, iso-butyl or tert-butyl.

Alkyl, which may be branched or linear, preferably has up to 12 carbon atoms, and is more preferably lower alkyl. Alkyl $R_3$ is preferably lower alkyl, especially isobutyl.

The prefix "lower" denotes a radical having up to and including 7, preferably up to and including 4, carbon atoms.

Lower alkyl is, preferably, n-propyl, isopropyl, n-butyl, isobutyl, sec-butyl, tert-butyl, n-pentyl, isopentyl, neopentyl, n-hexyl or n-heptyl, preferably isobutyl, sec-butyl, tert-butyl, isopropyl, ethyl or methyl, most preferably isopropyl, ethyl or methyl.

Etherified hydroxy is, for example, alkoxy, especially lower alkoxy, such as ethoxy or methoxy, aryloxy, especially phenyloxy, aryl-lower alkoxy, especially phenyl-lower alkoxy, heterocyclyloxy, especially pyridyloxy, or heterocyclyl-lower alkoxy, especially pyridyl-lower alkoxy (aryl and heterocyclyl preferably have the meanings given above).

Esterified hydroxy is preferably hydroxy esterified by an organic carboxylic acid, such as an alkanoic acid, for example lower alkanoyloxy.

Esterified carboxy is, for example, alkoxycarbonyl, especially lower alkoxycarbonyl, such as e.g. methoxycarbonyl.

Mono- or di-substituted amino is, preferably, N-alkylamino or N,N-dialkylamino, especially N-lower alkylamino or lower N,N-di-lower alkylamino, such as N-methylamino or N,N-dimethylamino.

Halogen is fluorine, chlorine, bromine or iodine, preferably fluorine, chlorine or bromine.

Unsubstituted or substituted cycloalkyl preferably has up to 12, more preferably 3 to 8 ring carbonyl atoms and is substituted by one or more, especially up to three, substitutents independently selected from those mentioned for substituted aryl, or preferably unsubstituted. Preferred is cyclopentyl, cyclohexyl or cycloheptyl.

In alkyl $R_3$ substituted with unsubstituted or substituted cycloalkyl, alkyl is preferably as defined above, more preferably lower alkyl, especially isopropyl, and is (preferably terminally) substituted by cycloalkyl as defined above.

In alkyl $R_3$ substituted with unsubstituted or substituted aryl, alkyl is preferably as defined in the last paragraph, and aryl is defined as above and is substituted by one or more, especially up to three, substitutents independently selected from those mentioned for substituted aryl, or unsubstituted; especially aryl is phenyl substituted by one or more, especially up to three, substitutents independently selected from halogen, especially fluoro, hydroxy or lower alkoxy, especially methoxy, or it is unsubstituted phenyl.

In alkyl $R_3$ substituted with unsubstituted or substituted heterocyclyl, alkyl is preferably as defined for alkyl $R_3$ substituted with cycloalkyl, and heterocyclyl is defined as above and is substituted by one or more, especially up to three, substitutents independently selected from those mentioned for substituted heterocyclyl, or unsubstituted.

If $A_1$ and $A_2$ each are substituted hydroxy, then substituted hydroxy is preferably alkyloxy, especially lower alkyloxy, aryloxy, especially with unsubstituted or substituted aryl as defined above, or cycloalkyloxy with unsubstituted or substituted cycloalkyl as defined above.

If $A_1$ and $A_2$ together with the binding boron atom and oxygen atoms form a ring or the formula IA* shown above, then W preferably carries the two oxygen atoms bound to the boron atom on two different carbon atoms that are spatially nearby or neighbouring carbon atoms, especially in vicinal ("1,2-") or in "1,3"-position (relatively to each other).

Alkylene is preferably an unbranched $C_2$-$C_{12}$—, preferably $C_2$-$C_7$alkylene moiety, e.g. ethylene, or propylene, in a broader aspect butylene, pentylene or hexylene, bound via two different carbon atoms as just described, preferably vicinal or in "1,3"-position. One or more, especially one, of the carbon atoms not bound to the oxygen atoms binding to the boron atom may be replaced by a heteroatom selected from O, S or preferably N (carrying the required number of H atoms, respectively), for example in 1,5-(3-aza-pentylene).

Substituted alkylene is preferably an unbranched lower alkylene moiety as defined above which is subsituted or unsubstituted by one or more, especially up to three, substituents preferably independently selected from lower alkyl, such as methyl or ethyl, e.g. in 1-methylethylene, 1,2-dimethylethylene, hydroxy, e.g. in 2-hydroxy-propylene, or hydroxy-lower alkyl, such as hydroxymethyl, e.g. in 1-hydroxymethyl-ethylene.

Unsubstituted or substituted cycloalkylene is preferably $C_3$-$C_{12}$—, more preferably $C_3$-$C_8$-cycloalkylene bound via two different carbon atoms as described for W, preferably vicinal or in "1,3"-position, such as cyclohexylene or cyclopentylene, in which one or more, especially one, of the carbon atoms not bound to the oxygen atoms binding to the boron atom may be replaced by a heteroatom selected from O, S or N (carrying the required number of H atoms, respectively), for example in tetrahydrofurylene or tetrahydropyranylene, and may be unsubstituted or substituted by one or more, especially up to three substituents independently selected from lower alkyl, such as methyl or ethyl, hydroxy, hydroxy-lower alkyl, such as methoxy, or mono- or oligosaccharidyl bound via an oxyygen atom ("oligosaccharidyl" preferably comprising up to five saccaridyl moieties).

Unsubstituted or substituted Bicycloalkylene is preferably $C_5$-$C_{12}$-bicycloalkylene bound via two different carbon atoms as described for W, preferably vicinal or in "1,3"-position, in which one or more, especially one, of the carbon atoms not bound to the oxygen atoms binding to the boron atom may be replaced by a heteroatom selected from O, S or N (carrying the required number of H atoms, respectively), and may be unsubstituted or substituted by one or more, especially up to three substituents independently selected from lower alkyl, such as methyl or ethyl, hydroxy and hydroxy-lower alkyl, such as methoxy. Preferred is pinanylene (2,3-(2,6,6-trimethyl-bicyclo[3.1.1]heptane)).

Unsubstituted or substituted tricycloalkylene is preferably $C_8$-$C_{12}$-tricycloalkylene bound via two different carbon atoms as described for W, preferably vicinal or in "1,3"-position, in which one or more, especially one, of the carbon atoms not bound to the oxygen atoms binding to the boron atom may be replaced by a heteroatom selected from O, S or N (carrying the required number of H atoms, respectively), and may be unsubstituted or substituted by one or more, especially up to three substituents independently selected from lower alkyl, such as methyl or ethyl, hydroxy and hydroxy-lower alkyl, such as methoxy.

Most preferably, $R_4$ is —$B(OH)_2$ or 2,9,9-trimethyl-3,5-dioxa-4-bora-tricyclo[6.1.1.0$^{2,6}$]dec-4-yl, especially (1S,2S, 6R,8S)-2,9,9-trimethyl-3,5-dioxa-4-bora-tricyclo[6.1.1.0$^{2,6}$]dec-4-yl.

In unsubstituted or substituted alkyl $R_5$, alkyl, which may be branched or linear, preferably has up to 12 carbon atoms, and is more preferably lower alkyl. Alkyl $R_5$ is preferably lower alkyl, especially isopropyl. Substituents, of which one or more, especially up to two, may be present, are independently selected from unsubstituted or substituted aryl (especially phenyl or hydroxyphenyl), unsubsituted or substituted heterocyclyl (especially imidazolyl or indolyl), unsubstituted or substituted cycloalkyl, each as defined above; hydroxy (preferred), carboxy (preferred), carbamoyl, mercapto, lower alkylthio, e.g. methylthio, phenyl, hydroxyphenyl, indolyl, imidazolyl, amino, tri-lower alkylamino, e.g. trimethylamino, lower alkanoylamino, e.g. acetylamino, guanidino, N-lower alkylguanidino, e.g. N-methylguanidino, or any other substituent completing an amino acid comprising $R_5$. Preferably, $R_5$ may be methyl, isopropyl, isobutyl, sec-butyl, mercaptomethyl, 2-methylthio-ethyl, phenylmethyl, hydroxyphenylmethyl, indol-3-ylmethyl, hydroxymethyl, 1-hydroxyethyl, 2-hydroxyethyl, carbamoylmethyl, 2-carbamoylethyl, 4-aminobutyl, 3-guanidinopropyl, 5-imidazolylmethyl, carboxymethyl or 2-carboxyethyl.

Asymmetric carbon atoms of a compound of formula I that are present may exist in the (R), (S) or (R,S) configuration, preferably in the (R) or (S) configuration, most preferably in the configuration indicated in formula I* below. Substituents at a double bond or a ring may be present in cis-(=Z-) or trans (=E-) form. The compounds may thus be present as mixtures of isomers or preferably as pure isomers.

Salt-forming groups in a compound of formula I are groups or radicals having basic or acidic properties. Compounds having at least one basic group or at least one basic radical, for example amino, a secondary amino group not forming a peptide bond or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethanesulfonic acid, or aromatic sulfonic acids, for example benzene-, p-toluene- or naphthalene-2-sulfonic acid. When several basic groups are present mono- or polyacid addition salts may be formed.

Compounds of formula I having acidic groups, for example a free boronic acid group ($-B(OH)_2$, that is, in formula IA* $A_1$ and $A_2$ each are hydroxy) or a carboxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of salts are possible.

Compounds of formula I having both acidic and basic groups can form internal salts.

Exemplary compounds of formula I include those wherein
$R_1$ is either substituted aryl-lower alkylcarbonyl or unsubstituted or substituted aryl,
$R_2$ is substituted aryl or unsubstituted or substituted heterocyclyl,
$R_3$ is lower alkyl, unsubstituted or substituted aryl or lower alkyl which is substituted by unsubstituted or substituted aryl,
$R_4$ is a moiety of the formula IA given above wherein $A_1$ and $A_2$ are hydroxy, lower alkyloxy, aryloxy with unsubstituted or substituted aryl or cycloalkyloxy with unsubstituted or substituted cycloalkyl, or wherein $A_1$ and $A_2$, together with the binding boron atom and the two binding oxygen atoms form a ring of the formula IA* given above wherein W is unsubstituted or substituted lower alkylene bound via two different carbon atoms that are spatially nearby or vicinal, especially in vicinal or, relatively to each other, in "1,3"-position, and
$R_5$ is lower alkyl, or salts thereof.

Exemplary compounds of formula I include those wherein
$R_1$ is phenyloxyphenyl-lower alkylcarbonyl; phenyl-lower alkoxyphenyl-lower alkylcarbonyl; pyridyloxyphenyl-lower alkylcarbonyl; phenyl-lower alkylcarbonyl substituted by lower alkoxy, especially methoxy, halogen, especially fluoro or chloro, or halogen-lower alkyl, especially trifluoromethyl; or preferably unsubstituted or substituted phenyl or naphthyl, wherein in both cases the substituents if present are independently one or more, especially one to three, substituents selected from the group consisting of lower alkyl, hydroxy, lower alkoxy, lower alkanoyloxy, carboxy, lower alkoxycarbonyl, formyl, lower alkanoyl, amino, N-lower alkylamino, N,N-di-lower alkylamino, mercapto, sulfo, lower alkyl-thio, carbamoyl, N-lower alkyl-carbamoyl; N,N-di-lower alkyl-carbamoyl, phenyl, naphthyl, pyridyl, cyano and nitro, more preferably lower alkoxy alkoxy, especially methoxy or ethoxy;
$R_2$ is phenyl substituted by one or more, especially one to three, moieties independently selected from the group consisting of hydroxy, lower alkoxy, especially methoxy, halogen, especially fluoro or chloro, and halogen-lower alkyl, especially trifluoromethyl;
$R_3$ is lower alkyl, especially isobutyl, phenyl or phenyl substituted by one or more, especially up to three substituents independently selected from the group consisting of hydroxy, lower alkoxy, especially methoxy, halogen, especially fluoro or chloro, and halogen-lower alkyl, especially trifluoromethyl;
$R_4$ is $-B(OH)_2$ (especially preferred) or 2,9,9-trimethyl-3,5-dioxa-4-bora-tricyclo[6.1.1.0$^{2,6}$]dec-4-yl, especially (1S,2S,6R,8S)-2,9,9-trimethyl-3,5-dioxa-4-bora-tricyclo[6.1.1.0$^{2,6}$]dec-4-yl; and
$R_5$ is lower alkyl, especially isopropyl;
or salts thereof.

Exemplary compounds of formula I include those wherein
$R_1$ is phenyloxyphenylacetyl, benzyloxyphenylacetyl, pyridyloxyphenylacetyl, biphenylyl, pyridylphenyl, lower alkylphenyl or substituted phenylpropionyloxy wherein the phenyl substituents are up to three substituents independently selected from the group consisting of methoxy, fluoro, chloro and trifluoromethyl;
$R_2$ is phenyl substituted with up to three methoxy substituents, especially 2,3,4-trimethoxyphenyl or 3,4,5-trimethoxyphenyl;
$R_3$ is isobutyl or phenyl that is unsubstituted or substituted with up to three moieties independently selected from hydroxy, fluoro and methoxy;
$R_4$ is (1S,2S,6R,8S)-2,9,9-trimethyl-3,5-dioxa-4-bora-tricyclo[6.1.1.0$^{2,6}$]dec-4-yl or especially $-B(OH)_2$; and
$R_5$ is isopropyl; or salts thereof.

Exemplary compounds of formula I include those wherein
$R_1$ is biphenylyl, lower alkyl-phenyl, phenyl-lower alkyl-carbonyl, phenoxy-phenyl-lower alkyl-carbonyl, phenyl-lower alkoxy-phenyl-lower alkyl-carbonyl or pyridyl-phenyl;
$R_2$ is either phenyl substituted by 1 to 3 lower alkoxy radicals or phenyl-lower alkoxy-phenyl;
$R_3$ is lower alkyl or phenyl-lower alkyl;
$R_4$ is 4,4,5,5-tetramethyl-[1,3,2]dioxaborolan-2-yl, (1S,2S,6R,8S)-2,9,9-trimethyl-3,5-dioxa-4-bora-tricyclo[6.1.1.0$^{2,6}$]dec-4-yl or $-B(OH)_2$; and
$R_5$ is lower alkyl; or salts thereof.

Other exemplary compounds of formula I or salts thereof, include those wherein the stereochemistry is as depicted in formula I*

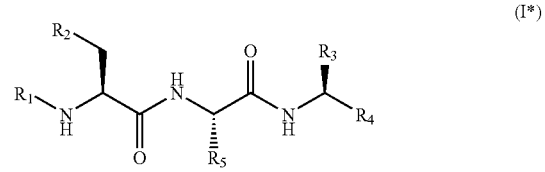

(I*)

wherein the shown configuration represents the absolute configuration and wherein $R_1$, $R_2$, $R_3$, $R_4$ and $R_5$ have the meanings as defined for a compound of formula I, especially those meanings described hereinabove as being preferred.

Other exemplary compounds of formula I or salts thereof, include those wherein the stereochemistry is as depicted in formula I**

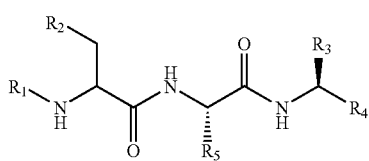

(I**)

wherein the shown configuration represents the absolute configuration and wherein $R_1$, $R_2$, $R_3$, $R_4$ and $R_5$ have the meanings as defined for a compound of formula I, especially those meanings described hereinabove as being preferred.

Other exemplary compounds of formula I or salts thereof, include mixtures of diastereomers, wherein the stereochemistry is as depicted in formula I***

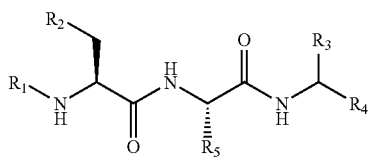

(I***)

wherein the shown configuration represents the absolute configuration and wherein $R_1$, $R_2$, $R_3$, $R_4$ and $R_5$ have the meanings as defined for a compound of formula I, especially those meanings described hereinabove as being preferred.

Most especially preferred are the compounds of formula I described in the Examples, or pharmaceutically acceptable salts thereof.

The compounds of formula I or salts thereof are prepared in accordance with processes known. The processes preferably comprise a) reacting a dipeptide analogue of the formula II,

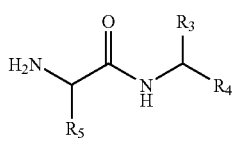

(II)

wherein $R_3$, $R_4$ and $R_5$ have the meanings given under formula I, with an amino acid of the formula III,

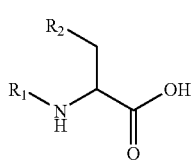

(III)

or a reactive derivative thereof, wherein $R_1$ and $R_2$ have the meanings given under formula I, functional groups present in a compound of formula II and/or III, with the exception of the groups participating in the reaction, being protected if necessary by readily removable protecting groups, and any protecting groups present are removed, or b) for the production of a compound of the formula I wherein $R_1$ is arylalkylcarbonyl or heterocyclylalkylcarbonyl and the other moieties $R_2$ to $R_5$ have the meanings given under formula I, reacting an amino compound of the formula IV,

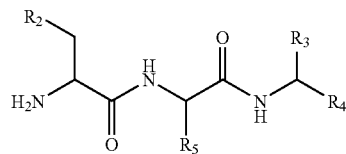

(IV)

wherein $R_2$, $R_3$, $R_4$ and $R_5$ have the meanings given under formula I, with a carbonic acid of the formula V,

(V)

or a reactive derivative thereof, wherein $R_1$ is arylalkylcarbonyl or heterocyclylalkylcarbonyl, functional groups present in a compound of formula IV and/or V, with the exception of the groups participating in the reaction, being protected if necessary by readily removable protecting groups, and any protecting groups present are removed, and, if desired, converting a compound of formula I obtained by process a) or b) into another compound of formula I, converting an obtained free compound of formula I into a salt, converting an obtained salt of a compound of formula I into a different salt or into its free form, and/or separating a mixture of isomeric compounds of formula I into the individual isomers.

The different possible stereoisomers of compounds of formula I can be prepared by using educts with the appropriate configuration. For example, compounds of formula I* or salts thereof can be prepared by a) reacting a dipeptide analogue of the formula II*,

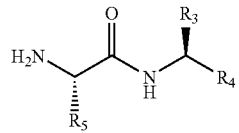

(II*)

wherein $R_3$, $R_4$ and $R_5$ have the meanings given under formula I, with an amino acid of the formula III*,

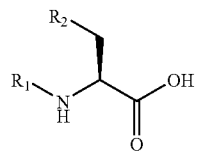

(III*)

or a reactive derivative thereof, wherein $R_1$ and $R_2$ have the meanings given under formula I, functional groups present in a compound of formula II* and/or III*, with the exception of the groups participating in the reaction, being protected if necessary by readily removable protecting groups, and any protecting groups present are removed, or b) for the production of a compound of the formula I* wherein $R_1$ is arylalkylcarbonyl or heterocyclylalkylcarbonyl and the other moieties $R_2$ to $R_5$ have the meanings given under formula I, reacting an amino compound of the formula IV*,

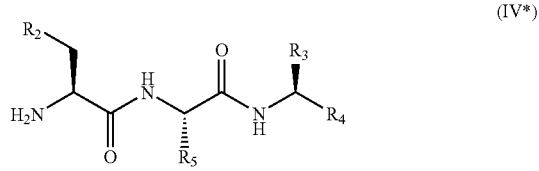

wherein $R_2$, $R_3$, $R_4$ and $R_5$ have the meanings given under formula I, with a carbonic acid of the formula V,

or a reactive derivative thereof, wherein $R_1$ is arylalkylcarbonyl or heterocyclylalkylcarbonyl, functional groups present in a compound of formula IV* and/or V, with the exception of the groups participating in the reaction, being protected if necessary by readily removable protecting groups, and any protecting groups present are removed, and, if desired, converting a compound of formula I* obtained by process a) or b) into another compound of formula I*, converting an obtained free compound of formula I* into a salt, or converting an obtained salt of a compound of formula I* into a different salt or into its free form.

The end products of formula I may contain substituents that can also be used as protecting groups in starting materials for the preparation of other end products of formula I, e.g. in the case of $R_4$ other than —$B(OH)_2$. Thus, within the scope of this text, only a readily removable group that is not a constituent of the particular desired end product of formula I is designated a "protecting group", unless the context indicates otherwise.

The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974.

A characteristic of protecting groups is that they can be removed readily (i.e. without the occurrence of undesired secondary reactions) for example by solvolysis, reduction, photolysis or alternatively under physiological conditions (e.g. by enzymatic cleavage).

Removal of a protecting group for the —$B(OH)_2$-group (in order to obtain a compound of the formula I wherein $R_4$ is —$B(OH)_2$) preferably takes place with an acid, e.g. hydrogen chloride, in an appropriate solvent, e.g. a lower alkanol, such as methanol, or a lower alkane, such as hexane, or a mixture thereof, at temperatures of 0 to 50° C., e.g. at room temperature.

At least two processes can be used to synthesize the proteasome inhibitors of formula I. In process "a", the reaction is carried out by dissolving the compounds of formulae II and III in a suitable solvent, for example N,N-dimethylformamide, N,N-dimethylacetamide, N-methyl-2-pyrrolidone, methylene chloride, or a mixture of two or more such solvents, and by the addition of a suitable base, for example triethylamine, diisopropylethylamine (DIEA) or N-methylmorpholine and a suitable coupling agent that forms a preferred reactive derivative of the carbonic acid of formula III in situ, for example dicyclohexylcarbodiimide/1-hydroxybenzotriazole (DCC/HOBT); O-(1,2-dihydro-2-oxo-1-pyridyl)-N,N,N',N'-tetramethyluronium tetrafluoroborate (TPTU); O-benzotriazol-1-yl)-N,N,N',N'-tetramethyluronium tetrafluoroborate (TBTU); or 1-(3-dimethylaminopropyl)-3-ethylcarbodiimide hydrochloride (EDC). For review of other possible coupling agents, see e.g. Klauser; Bodansky, *Synthesis* 1972, 453-463. The reaction mixture is preferably stirred at a temperature of between approximately –20 and 50° C., especially between 0° C. and room temperature, to yield a compound of formula I. The reaction is preferably carried out under an inert gas, e.g. nitrogen or argon.

In process "b", the reaction is preferably carried out under conditions analogous to those described for process a).

Salts of a compound of formula I with a salt-forming group may be prepared in a manner known per se. Acid addition salts of compounds of formula I may thus be obtained by treatment with an acid or with a suitable anion exchange reagent.

Salts can usually be converted to free compounds, e.g. by treating with suitable basic agents, for example with alkali metal carbonates, hydrogencarbonates, or hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

Compounds of the formula I wherein $R_4$ is other than —$B(OH)_2$ can be converted into compounds of the formula I wherein $R_4$ is —$B(OH)_2$ according to standard procedures, e.g. using isobutyl-boronic acid (i-BuB(OH)$_2$ in the presence of an acid, especially hydrohalic acid in a water/methanol/hexane mixture, at temperatures preferably ranging from 0 to 50° C., e.g. at room temperature.

In both process a) and b), for the conversion or for the synthesis of the intermediates or starting material, the solvents from which those can be selected which are suitable for the reaction in question include for example water, esters, typically lower alkyl-lower alkanoate, e.g., diethyl acetate, ethers, typically aliphatic ethers, e.g. diethylether, or cyclic ethers, e.g. tetrahydrofuran, liquid aromatic hydrocarbons, typically benzene or toluene, alcohols, typically methanol, ethanol or 1- or 2-propanol, nitriles, typically aceto-nitrile, halogenated hydrocarbons, typically dichloromethane, acid amides, typically dimethylformamide, bases, typically heterocyclic nitrogen bases, e.g. pyridine, carboxylic acids, typically lower alkanecarboxylic acids, e.g. acetic acid, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process. Such solvent mixtures may also be used in processing, for example through chromatography or distribution.

New starting materials and/or intermediates, as well as processes for the preparation thereof, are likewise the subject of this invention. In the preferred embodiment, such starting materials are used and reaction conditions selected such as to allow the manufacture of the preferred compounds.

The starting materials of formulae II-V or their precursors are known, can be prepared according to known processes, or are commercially obtainable; in particular, they can be prepared using processes identical or in analogy to those described in the Examples.

A compound of formula II, wherein the substituents are as defined above under formula I, is obtainable for example by the following reactions:

First, a boronic acid analogue of an amino acid of the formula VI

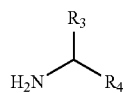

(VI)

comprising for example the configuration as indicated in formula VI*

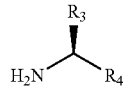

(VI*)

wherein $R_3$ has the meanings given above for compounds of formula I and $R_4$ has the meanings other than $-B(OH)_2$ mentioned above for compounds of formula I, especially is (1S,2S,6R,8S)-2,9,9-trimethyl-3,5-dioxa-4-bora-tricyclo [6.1.1.0$^{2,6}$]dec-4-yl, or an acid addition salt thereof, especially the salt thereof with trifluoroacetic acid, is condensed with an amino acid of the formula VII

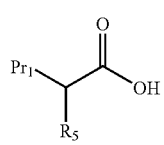

(VII)

comprising for example the configuration as indicated in formula VII*

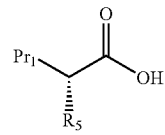

(VII*)

or a reactive derivative thereof, wherein $R_5$ has the meanings given above for compounds of the formula I and $Pr_1$ is a protected amino group, preferably tert-butoxycarbonylamino, under reaction conditions analogous to those described for reaction a) above (also a condensation reaction, also preferably with in situ formation of active carbonic acid derivatives), thus yielding a compound of formula II in N-protected form which is then N-deprotected, e.g. using conditions described in the standard textbooks mentioned above, in the case of tert-butoxycarbonylamino e.g. with hydrochloric acid in an appropriate solvent, e.g. dioxane and/or methylene chloride giving a compound of the formula II that can be used directly in process a).

The boronic acids of the formula VI are known, commercially available and/or can be synthesized according to known procedures. For example, compounds of the formula VI wherein $R_3$ is lower alkyl, especially isobutyl and $R_4$ is as described for compounds of the formula VI, preferably (1S, 2S,6R,8S)-2,9,9-trimethyl-3,5-dioxa-4-bora-tricyclo [6.1.1.0$^{2,6}$]dec-4-yl, can be prepared by reacting a compound of the formula VIII,

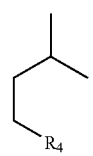

(VIII)

wherein $R_4$ has the meanings just described, in an appropriate solvent, e.g. methylene chloride, with n-lower alkyl lithium, especially n-butyllithium, and subsequently with zinc chloride, yielding a compound of the formula IX,

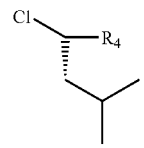

(IX)

wherein $R_4$ has the meanings given above under formula VI. This compound is then reacted with $LiN(SiCH_3)_2$, and the resulting compound of the formula is then reacted in the presence of trifluoro acetic acid to yield the salt of the formula X,

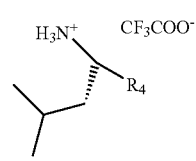

(X)

wherein R₄ has the meanings given under formula VI, which is a compound of the formula VI and can then be used directly for reaction with the compound of formula VII as shown above.

A compound of the formula III is known, commercially available and/or can be obtained according to standard procedures.

For example, a compound of the formula III wherein R₁ is aryl, especially biphenylyl, may be prepared by reacting a compound of the formula XI,

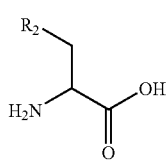
(XI)

comprising for example the configuration as indicated in formula XI*

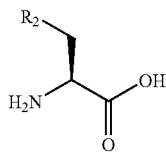
(XI*)

wherein R₂ has the meanings given for a compound of the formula I, which is known, commercially available or obtainable according to standard procedures, with a compound of the formula XII,

R₁—X  (XII)

wherein R₁ is aryl and X is halogen, especially bromo, in an appropriate solvent, e.g. in dimethylformamide, in the presence of a base, especially an alkali metal carbonate, e.g. potassium carbonate, at temperatures between 50 and 100° C., e.g. at 90° C., preferably under inert gas, e.g. nitrogen or argon. This directly yields the corresponding compound of the formula III.

Amino acid derivatives of the formula VII are known, commercially available or obtainable according to standard procedures. They are preferably used in the amino protected form, e.g. with tert-butoxycarbonylamino instead of the free amino group.

Compounds of the formula IV can be obtained e.g. by reacting a compound of the formula II comprising for example the configuration as indicated in formula II*, as defined in process a), with an N-protected amino acid of the formula XIII,

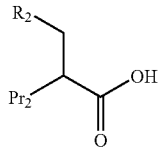
(XIII)

comprising for example the configuration as indicated in formula XIII*

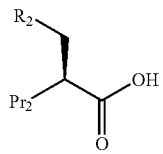
(XIII*)

or a reactive derivative thereof, wherein R₂ is as defined under formula I and Pr₂ is protected amino, especially tert-butoxycarbonylamino, under preferred condensation reaction conditions as described under process a) above. From the resulting compound, a compound of formula IV wherein the N-terminal amino group is present in protected form, then the N-terminal protecting group is removed, e.g. in the case of tert-butoxycarbonylamino with hydrogen chloride in dioxane.

In other embodiments, the apoptosis-inducing agent is a proteasome inhibitor from the 2,4-diamino-3-hyroxycarboxylic acid family of compounds. See, PCT WO 00/64863. For example, in some embodiments, the proteasome inhibitor is a 2,4-diamino-3-hydroxycarboxylic acids of formula XIV,

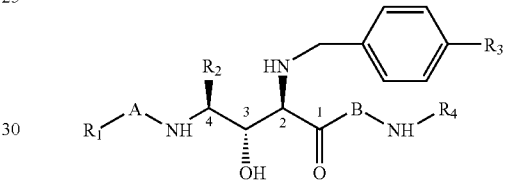

wherein

A and B independently represent a bond or an unsubstituted or substituted aminoacyl moiety;

R₁ represents hydrogen; an amino protecting group; or a group of formula R₅Y-wherein R₅ represents hydrogen or an unsubstituted or substituted alkyl, alkenyl, alkinyl, aryl, arylalkyl, heteroaryl, heteroarylalkyl, heterocyclyl or heterocyclylalkyl group; and Y represents —CO—; —NH—CO—; —NH—CS—; —SO₂—; —O—CO—; or —O—CS—;

R₂ represents the side chain of a natural amino acid; an alkyl, arylalkyl, heteroarylalkyl or cycloalkylalkyl group; or trimethylsilylmethyl, 2-thienylmethyl or styrylmethyl;

R₃ represents halogen, alkyl, alkoxy or hydroxyalkoxy; and

R₄ represents 2(R)-hydroxyindan-1(S)-yl; (S)-2-hydroxy-1-phenylethyl; or 2-hydroxy-benzyl unsubstituted or substituted in 4 position by methoxy; wherein the 2,4-diamino-3-hydroxycarboxylic acid is in free form, is a pharmaceutically acceptable salt thereof or in a pharmaceutical composition.

Unsubstituted or substituted alkyl preferably is alkyl of 1 to 5 carbon atoms, preferably of 1 to 4 carbon atoms; e.g. methyl, ethyl, isopropyl or tert-butyl; it is especially of 1 or 4 carbon atoms. The substituent is e.g. phenoxy, hydroxy or unprotected or protected amino.

Unsubstituted or substituted arylalkyl is e.g. phenylalkyl of altogether 7 to 10 carbon atoms, such as benzyl or 2-phenylethyl. It is unsubstituted or substituted in the aryl or alkyl moiety by e.g. hydroxy, such as in benzyl-CH(OH)— or phenyl —CH(CH₂OH)—, by alkyl, amino or alkylamino; or is e.g. naphthylalkyl of 1 to 4 carbon atoms in the alkylene part, especially naphthylmethyl.

An amino protecting group preferably is benzyloxycarbonyl, cycloalkylalkoxycarbonyl, especially cyclohexylmethoxycarbonyl, or tert-butoxycarbonyl. Unsubstituted or substituted heteroarylalkyl preferably is pyrldylalkyl, especially 2-pyridylmethyl and 4-pyddylmethyl.

Aryl, heteroaryl and the aryl parts of arylalkyl and heteroarylalkyl may be mono- or polycyclic, such as e.g. pyridyl, naphthyl, 9-fluorenylmethoxycarbonyl (FMOC) or benz-imidazolyl. The alkylene part of arylalkyl or heteroarylalkyl may be substituted by e.g. hydroxy.

A heterocyclyl group, and the heterocyclyl part of a heterocyclylalkyl group, is a saturated heterocyclic group having one or more heteroatoms selected from nitrogen, oxygen and sulfur. It preferably has 5 or 6 ring constitutent atoms, and preferably up to 3 heteroatoms.

Cycloalkylalkyl preferably is cyclohexylalkyl; it preferably is of 1 to 4 carbon atoms in the alkylene part.

Halogen is fluorine, chlorine, bromine or iodine, preferably chlorine or bromine.

Alkyl and alkoxy preferably are of 1 to 4 carbon atoms, especially of 1 or 2 carbon atoms, more especially methyl or methoxy.

Hydroxyalkoxy preferably is ω-hydroxyalkoxy of 2 to 4 carbon atoms, especially 2-hydroxyethoxy.

A salt is e.g. an acid addition salt such as a hydrochloride.

The compounds of formula I have several chiral centers and can therefore exist in a variety of stereoisomers. The invention provides all stereoisomers as well as racemic mixtures unless specified otherwise. The isomers may be resolved or separated by conventional techniques, e.g. chromatographically. As appears from formula I the configuration at the carbon atom in the 2 position is R, in the 3 and 4 positions it is S.

$R_1$ preferably is hydrogen, pyridylalkoxycarbonyl, naphthylalkoxycarbonyl, naphthylalkylcarbonyl, benzyl-CH(OH)-carbonyl, phenoxymethylcarbonyl, phenylalkylcarbonyl or an amino protecting group such as tert.-butoxycarbonyl, cycloalkylalkoxycarbonyl, especially cyclohexylmethoxycarbonyl, or benzyloxycarbonyl which is unsubstituted or substituted by alkyl or amino; it especially is naphthylmethoxycarbonyl, naphthylmethylcarbonyl, pyridylmethoxycarbonyl, phenylpropionyl, aminophenylpropionyl, tert.-butoxycarbonyl, aminobenzyfoxycarbonyl, alkylbenzyloxycarbonyl, dialkylbenzyloxycarbonyl or benzyloxycarbonyl, even more preferably benzyloxycarbonyl.

When A is an unsubstituted or substituted aminoacyl moiety, it preferably is an unsubstituted or substituted α-aminoacyl moiety such as alanine, leucine, isoleucine, asparagine, valine, tert-butylglycine, tert-leucine or histidine. It preferably is the protected or unprotected moiety of a natural α-amino acid, preferably of an amino acid which is a normal constitutive part of proteins, or tent leucine. It preferably has the L configuration. A is especially glycine, L-valine, L-tert-leucine or a bond, even more preferably L-tert-leucine.

$R_2$ preferably is the side chain of a natural amino acid, preferably of an α-amino acid, preferably of an amino acid which is a normal constitutive part of proteins. It is e.g. isopropyl, aminocarbonylmethyl, methyl, 1-methylpropyl, benzyl, 4-hydroxybenzyl or isobutyl, preferably benzyl.

When B is an unsubstituted or substituted aminoacyl moiety, it preferably is an unsubstituted or substituted α-aminoacyl moiety, such as phenylalanine, valine, leucine, isoleucine, alanine or asparagine. It preferably is the unsubstituted or substituted moiety of a natural α-amino acid, preferably of an amino acid which is a normal constitutive part of proteins. α-Amino acids with a second carboxyl group, e.g. glutaminic acid, are preferably esterified with an $C_1$-$C_3$ alcohol, especially methanol. It preferably has the L-configuration. B especially is L-valine, L-glutaminic acid methyl ester or a bond, even more preferably L-valine.

$R_3$ preferably is halogen, methyl or methoxy, especially methoxy.

$R_4$ preferably is 2(R)-hydroxyindan-1(S)-yl or 2-hydroxybenzyl unsubstituted or substituted as defined above, especially 2-hydroxy-4-methoxy-benzyl.

Y preferably is —CO— or —O—CO—, especially —O—CO—.

$R_5$ preferably is an unsubstituted or substituted alkyl, arylalkyl or heteroarylalkyl group, especially alkyl; when it is unsubstituted or substituted heteroarylalkyl it preferably is pyridylalkyl, especially 2-pyddylmethyl; when it is unsubstituted or substituted arylalkyl it preferably is benzyl-CH(OH)—; when it is substituted alkyl it preferably is phenoxymethyl.

In some embodiments, the proteasome inhibitor is a 2-amino-3-hydroxy-4tert-leucyl-amino-5-phenyl-pentanoic acid amide derivative. See, e.g., PCT 01/89282.

For example, in some embodiments, the proteasome inhibitors of the invention relate to compounds of formula XV

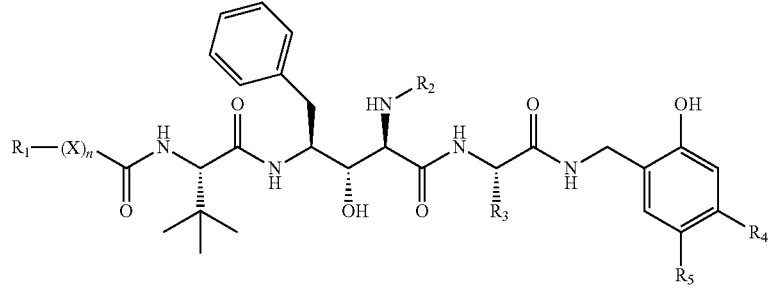

wherein n is 0 or 1;

$R_1$ and $R_2$ are independently of the other an aliphatic radical, or an aromatic, aromatic-aliphatic, cycloaliphatic, cycloaliphatic-aliphatic, heterocyclic or heterocyclic-aliphatic radical, each radical having not more than 20 carbon atoms;

$R_3$ is hydrogen, oxa-alkyl, an aliphatic radical or a radical with up to 20 carbon atoms of the formula —$(Y)_m$—$R_6$, wherein Y is alkyl, m is 0 or 1 and $R_6$ is an unsubstituted or substituted monocyclic radical with 5 or 6 ring members containing up to 3 hetero atoms selected from the group consisting of nitrogen, oxygen and sulfur, wherein said monocyclic radical can also be fused to a benzo ring;

$R_4$ and $R_5$ are independently selected from the group consisting of hydrogen; an aliphatic radical; free, etherified or esterified hydroxy; free or esterified carboxy; formyl; alkanol; unsubstituted, mono-or di-substituted amino; mercapto; sulfo; alkyl-thio; carbamoyl; N-alkyl-carbamoyl; N,N-di-alkyl-carbamoyl; cyano and nitro; wherein carbon containing radicals $R_4$ and $R_5$ have up to 12 carbon atoms, with the proviso that $R_4$ and $R_5$ are not both hydrogen if n is 1, $R_1$ is benzyl or tert-butyl, $R_2$ is benzyl or 4-methoxy-benzyl, $R_3$ is isopropyl and X is oxygen and that $R_4$ is not methoxy if n is 0 or 1, $R_2$ is 4-methoxy-benzyl, $R_3$ is hydrogen and X is oxygen; and X is nitrogen, oxygen or sulfur;

or salts thereof.

Within the context of the 2-amino-3-hydroxy-4-tert-leucyl-amino-5-phenyl-pentanoic acid amide derivatives, the general terms used hereinbefore and hereinafter preferably have the following meanings: n is 0 or 1, preferably 0.

An aliphatic radical has up to 12 carbon atoms, preferably up to 7 carbon atoms, most preferably up to 4 carbon atoms, and is such an unsubstituted or substituted aliphatic hydrocarbon radical, that is to say such an unsubstituted or substituted alkynyl, alkenyl or preferably alkyl radical, one or more substituents preferably being independently selected from the group consisting of free, etherified or esterified hydroxy; free or esterified carboxy; formyl; alkanol; unsubstituted, mono-or di-substituted amino; guanidino; mercapto; sulfo; alkyl-thio; carbamoyl; N-alkyl-carbamoyl; N,N-di-alkyl-carbamoyl; cyano and nitro.

An aliphatic radical $R_1$ is preferably lower alkyl, such as especially tert-butyl.

An aliphatic radical $R_3$ is preferably unsubstituted lower alkyl or lower alkyl substituted by hydroxy, carboxy, amino, carbamoyl, guanidino, mercapto or alkyl-thio, most preferably a side chain of the amino acids alanine, leucine, isoleucine, serine, threonine, cysteine, methionine, asparagine, glutamin, aspartate, glutamate, lysine or arginine, especially valine.

An aliphatic radical $R_4$ is preferably methoxy.

An aromatic radical $R_1$ or $R_2$ has not more than 20 carbon atoms, especially not more than 12 carbon atoms, and is unsubstituted or substituted, preferably in each case unsubstituted or substituted phenyl or naphthyl, especially 1-naphthyl, one or more substituents preferably being independently selected from the group consisting of an aliphatic radical; free, etherified or esterified hydroxy; free or esterified carboxy; formyl; alkanol; unsubstituted, mono-or di-substituted amino; mercapto; sulfo; alkyl-thio; carbamoyl; N-alkyl-carbamoyl; N,N-di-alkyl-carbamoyl; cyano and nitro, more preferably being selected from alkyl, e. g. methyl, ethyl or propyl; alkoxy, e. g. methoxy or ethoxy; di-substituted amino, e. g. dimethylamino; halogen, e. g. chloro or bromo; and halogen-alkyl, e. g. trifluoromethyl.

In an aromatic-aliphatic radical $R_1$ or $R_2$ having not more than 20 carbon atoms the aromatic moiety is as defined above and the aliphatic moiety is preferably lower alkyl, such as especially $C_1$-$C_2$ alkyl, which is substituted preferably as defined for the aromatic radical or preferably unsubstituted. An aromatic-aliphatic radical $R_1$ is preferably benzyl or naphthalen-1-ylmethyl. An aromatic-aliphatic radical $R_2$ is preferably benzyl substituted in the benzene moiety by 1-5, preferably by 1-3 methoxy groups; benzyl substituted in the benzene moiety, preferably in position 4, by a dimethylamino group; or naphthalen-1-ylmethyl. Most preferably an aromatic-aliphatic radical R2 is 2,3,4- or 3,4,5-trimethoxybenzyl.

A cycloaliphatic radical $R_1$ or $R_2$ has up to 20, especially up to 10 carbon atoms, is mono-or poly-cyclic and is substituted preferably as defined for the aromatic radical or preferably unsubstituted, for example such a cycloalkyl radical, especially such a 5-or 6-membered cycloalkyl radical, such as preferably cyclohexyl.

In a cycloaliphatic-aliphatic radical $R_1$ or $R_2$ having not more than 20 carbon atoms the cycloaliphatic moiety is as defined above and the aliphatic moiety is preferably lower alkyl, such as especially $C_1$-$C_2$ alkyl, which is substituted preferably as defined for the aromatic radical or preferably unsubstituted, for example cyclohexyl-methyl.

A heterocyclic radical $R_1$ or $R_2$ contains up to 20 carbon atoms, generally up to 12 carbon atoms, and is substituted preferably as defined for the aromatic radical or unsubstituted and is preferably a saturated or unsaturated monocyclic radical having 5 or 6 ring members and 1 to 3 hetero atoms which are preferably selected from the group consisting of nitrogen, oxygen and sulfur, for example, thienyl or pyridyl, or a bi-or tri-cyclic radical wherein, for example, a benzene radical is fused to the mentioned monocyclic radical, especially, for example, indolyl, such as 5-indolyl, or chinolyl, such as 8-chinolyl.

In a heterocyclic-aliphatic radical $R_1$ or $R_2$ having not more than 20 carbon atoms the heterocyclic moiety is as defined above and the aliphatic moiety is preferably lower alkyl, such as especially $C_1$-$C_2$ alkyl, which is substituted preferably as defined for the aromatic radical or preferably unsubstituted. A heterocyclic-aliphatic radical $R_1$ or $R_2$ is for example indolylmethyl, especially 5-indolyl-methyl, or chinolyl-methyl, especially 8-chinolyl-methyl.

Oxa-alkyl $R_3$ is a radical of the formula $-G(O-CH_2-CH_2)_t-R_7$, in which G and $R_7$ are alkyl, preferably lower alkyl, and t is 1 to 3, preferably 2, and is especially 2-(1,4-dioxa-hexyl)-ethyl.

In a radical of the formula $-(Y)_m-R_6$ having up to 20 carbon atoms, Y is alkyl, preferably lower alkyl, m is 0 or 1 and the radical $R_6$ is a saturated or unsaturated monocyclic radical having 5 or 6 ring members and up to 3 hetero atoms selected from the group consisting of nitrogen, oxygen and sulfur and alternatively containing a fused benzo ring, such a radical being substituted preferably as defined for the aromatic radical or preferably unsubstituted.

A radical $R_6$ is preferably bound to Y via a ring carbon atom and is for example an unsubstituted or substituted member selected from the group consisting of cyclopentyl, cyclohexyl, cyclopentadienyl, phenyl, pyrrolidyl, pyrazolidyl, imidazolidyl, tetrahydrofuryl, piperidyl, piperazinyl, morpholinyl, pyrrolyl, pyrazolyl, imidazolyl, furyl, thienyl, pyridyl, pyrazinyl, pyridazinyl, pyrimidinyl, indenyl, naphthyl, indolyl and chinolyl.

Most preferably a radical of the formula $-(Y)_m-R_6$ is piperidyl, especially 4-piperidyl, piperazin-ethyl, especially piperazin-1-ylethyl, morpholinyl-ethyl, especially morpholin-4-ylethyl, pyridyl-methyl, such as 2-, 3-or 4-pyridyl-methyl, or a side chain of the amino acids phenylalanine, tyrosine, tryptophane or histidine.

X is preferably oxygen (—O—).

Alkyl is preferably lower alkyl.

The prefix "lower" denotes a radical having up to and including 7, preferably up to and including 4, carbon atoms.

Lower alkyl is, for example, n-propyl, isopropyl, n-butyl, isobutyl, sec-butyl, tert-butyl, n- pentyl, isopentyl, neopentyl, n-hexyl or n-heptyl, preferably isobutyl, sec-butyl, tert-butyl, isopropyl, ethyl or methyl, most preferably isobutyl, ethyl or methyl.

Etherified hydroxy is, for example, alkoxy, especially lower alkoxy, such as ethoxy or methoxy. Esterified hydroxy is preferably hydroxy esterified by an organic carboxylic acid, such as alkanoic acid, or a mineral acid, such as a hydrohalic acid, for example lower alkanoyloxy or especially halogen, such as iodine or especially fluorine, chlorine or bromine.

Esterified carboxy is, for example, alkoxycarbonyl, especially lower alkoxycarbonyl, such as e. g. methoxycarbonyl.

Alkanol is, for example, alkylcarbonyl, especially lower alkylcarbonyl, such as e. g. acetyl.

Mono-or di-substituted amino is, for example, N-alkylamino or N,N-dialkylamino, especially N-lower alkylamino or lower N,N-di-lower alkylamino, such as e. g. N-methylamino or N,N-dimethylamino.

Halogen is fluorine, chlorine, bromine or iodine, preferably fluorine, chlorine or bromine.

The structure of Formula XV as shown above indicates the absolute configuration.

Salt-forming groups in a compound of Formula XV are groups or radicals having basic or acidic properties. Compounds having at least one basic group or at least one basic radical, for example a free amino group, a pyrazinyl radical or a pyridyl radical, may form acid addition salts, for example with inorganic acids, such as hydrochloric acid, sulfuric acid or a phosphoric acid, or with suitable organic carboxylic or sulfonic acids, for example aliphatic mono-or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxybenzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene-or naphthalene-2-sulfonic acid. When several basic groups are present mono-or poly-acid addition salts may be formed.

Compounds of Formula XV having acidic groups, for example a free carboxy group in the radical Rio, may form metal or ammonium salts, such as alkali metal or alkaline earth metal salts, for example sodium, potassium, magnesium or calcium salts, or ammonium salts with ammonia or suitable organic amines, such as tertiary monoamines, for example triethyl- amine or tri-(2-hydroxyethyl)-amine, or heterocyclic bases, for example N-ethyl-piperidine or N,N'-dimethyl-piperazine.

Compounds of Formula XV having both acidic and basic groups can form internal salts.

For the purposes of isolation or purification, as well as in the case of compounds that are used further as intermediates, it is also possible to use pharmaceutically unacceptable salts.

Only pharmaceutically acceptable, non-toxic salts are used for therapeutic purposes, however, and those salts are therefore preferred.

Owing to the close relationship between the novel compounds in free form and in the form of their salts, including those salts that can be used as intermediates, for example in the purification of the novel compounds or for the identification thereof, hereinbefore and hereinafter any reference to the free compounds should be understood as including the corresponding salts, where appropriate and expedient.

VII. Administration and Pharmaceutical Compositions

The antibodies and agents of the invention can be administered directly to the mammalian subject for treatment, e.g., of hyperproliferative disorders including cancer such as, but not limited to: carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, multiple myelomas, Hodgkin's lymphoma, and non-Hodgkin's lymphoma (see, CANCER:PRINCIPLES AND PRACTICE (DeVita, V. T. et al. eds 1997) for additional cancers).

Administration of the compositions of the present invention is by any of the routes normally used for introducing a chemotherapeutic compound into ultimate contact with the tissue to be treated. The antibodies and agents are administered in any suitable manner, optionally with pharmaceutically acceptable carriers. Suitable methods of administering such antibodies and agents are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences,* 17th ed. 1985)).

The antibodies and agents, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, by orally, topically, intravenously, intraperitoneally, intravesically or intrathecally. Optionally, the compositions are administered nasally. The formulations of compounds can be presented in unit-dose or multi-dose sealed containers, such as ampules and vials. Solutions and suspensions can be prepared from sterile powders, granules, and tablets of the kind previously described. The modulators can also be administered as part a of prepared food or drug. The compounds of the present invention can also be used effectively in combination with one or more additional active agents (e.g., chemotherapeutics) depending on the desired therapy or effect.

The dose administered to a patient, in the context of the present invention should be sufficient to effect a beneficial response in the subject over time. The dose will be determined by the efficacy of the particular modulators employed and the condition of the subject, as well as the body weight or surface area of the area to be treated. The size of the dose also will be determined by the existence, nature, and extent of any adverse side-effects that accompany the administration of a particular compound or vector in a particular subject. Administration can be accomplished via single or divided doses.

The antibody agonist and the apoptosis-inducing agent can be administered together in a mixture or each can be administered separately. The antibody agent and the apoptosis inducing agent can, but need not, be administered concurrently.

VIII. Inhibitors of Apoptosis

As described herein, a variety of gene products either inhibit (e.g., molecules listed in the first portion of FIG. 27; and UbcH10) or promote (e.g., molecules listed in the bottom portion of FIG. 27) TRAIL-induced (and anti-DR4 or anti-DR5-induced) apoptosis. Those gene products that inhibit TRAIL-induced apoptosis can be targeted with inhibitors to synergistically increase apoptosis induced by TRAIL, anti-DR4 or anti-DR5 antibodies. Similarly, those gene products that promote TRAIL-induced apoptosis can be targeted with activators to synergistically increase apoptosis induced by TRAIL, anti-DR4 or anti-DR5 antibodies.

Alternatively, activators of gene products that inhibit TRAIL-induced apoptosis can be used to reduce apoptosis where and when it is detrimental. Similarly, inhibitors of those gene products that promote TRAIL-induced apoptosis can also be used to reduce apoptosis where and when it is detrimental. One such disorder is thrombotic thrombocytopenic purpura (TTP) (Kwaan, H. C., *Semin. Hematol.*, 24:71 (1987); Thompson et aL, *Blood,* 80:1890, (1992)). Increasing TTP-associated mortality rates have been reported by the U.S. Centers for Disease Control (Torok et al., *Am. J. Hematol.* 50:84, 1995).

Plasma from patients afflicted with TTP (including HIV$^+$ and HIV$^-$ patients) induces apoptosis of human endothelial cells of dermal microvascular origin, but not large vessel origin (Laurence et aL, *Blood,* 87:3245 (1996)). Plasma of TTP patients thus is thought to contain one or more factors that directly or indirectly induce apoptosis. As described in PCT application WO 97/01633 (hereby incorporated by reference), TRAIL is present in the serum of TTP patients, and may play a role in inducing apoptosis of microvascular endothelial cells.

Another thrombotic microangiopathy is hemolytic-uremic syndrome (HUS) (Moake, J. L., *Lancet,* 343:393 (1994); Melnyk et al., *Arch. Intern. Med.* 155:2077, (1995)). One embodiment of the invention is directed to treat the condition that is often referred to as "adult HUS" (even though it can strike children as well). A disorder known as childhood/diarrhea-associated HUS differs in etiology from adult HUS.

Other conditions characterized by clotting of small blood vessels. Such conditions include but are not limited to the following: Cardiac problems seen in about 5-10% of pediatric AIDS patients are believed to involve clotting of small blood vessels. Breakdown of the microvasculature in the heart has been reported in multiple sclerosis patients. As a further example, treatment of systemic lupus erythematosus (SLE) is contemplated.

IX. Predicting Efficacy of Anti-cancer Treatments With Anti-DR5 Agonists

The inventors have discovered that expression of the gene product Myc is necessary but not sufficient for efficacy of anti-DR5 antibodies to induce apoptosis in tumor cells. Accordingly, expression of Myc in tumor cells (e.g., from a biopsy) provides a marker for identifying cells (and therefore subjects) that are unlikely to respond to DR5-targeted therapies. Specifically, if tumor cells express less Myc than wild-type cells, it is less likely that DR5-targeted therapy will be effective than if Myc is expressed at or above wildtype expression levels. Thus, the present invention provides methods of determining the efficacy of anti-DR5 agonist antibody-based therapies by obtaining a sample of tumor cells from a subject and detecting expression levels of Myc in the cells, wherein a lower than wild type expression level of Myc indicates that the therapies will have reduced or no efficacy in killing tumor cells.

EXAMPLES

The following examples are provided to further illustrate the invention but not to limit its scope. Other variants of the invention will be readily apparent to one of ordinary skill in the art and are encompassed by the appended claims.

Abbreviations:
  abs. absolute
  i-BuB(OH)2 Isobutyl-boronic acid
  DIEA N-Ethyldiisopropylamine
  DMF N,N-Dimethyl-formamide
  equiv equivalent(s)
  ES-MSElectrospray Mass Spectroscopy
  EtOAc ethyl acetate
  h hour(s)
  HPLC High Performance Liquid Chromatography
  MeOH methanol
  min minute(s)
  m.p. melting point
  MPLC Medium Pressure Liquid Chromatography
  Rf ratio of fronts value obtained by TLC on silica gel 60 F254 (Merck, Darmstadt)
  rt room temperature
  TBTU O-(Benzotriazol-1-yl)-N,N,N',N'-tetramethyluronium tetrafluoroborate
  TFA trifluoroacetic acid
  TLC Thin Layer Chromatography
  tR retention time Ratios of eluents and other solvent mixtures are given in volume by volume (v/v), if not mentioned otherwise.

Visualization of TLC:

TLC spots of final compounds or interemediates that are not detectable by UV-irradiation are visualized using a potassium permanganate staining solution followed by heating the plate.

Composition of potassium permanganate staining solution: 2.5 g of KMnO4 (Potassium permanganate) (Fluka, Buchs, Switzerland) in 800 ml of H2O and 200 ml of 1N H$_2$SO$_4$.

Analytical HPLC Conditions:

System 1

Linear gradient 2-100% CH$_3$CN (0.1% TFA) and H$_2$O (0.1% TFA) in 10 min+2 min 100% CH$_3$CN (0.1% TFA); detection at 215 nm, flow rate 0.7 mL/min at 25° C. Column: Nucleosil 120-3 C18 (125×3.0 mm).

System 2

Linear gradient 20-100% CH$_3$CN (0.1% TFA) and H$_2$O (0.1% TFA) in 7 min+2 min 100% CH$_3$CN (0.1% TFA); detection at 215 nm, flow rate 1 mL/min at 30° C. Column: Nucleosil 100-3 C18HD (125×4 mm).

System 3

Linear gradient 20-100% CH$_3$CN (0.1% TFA) and H$_2$O (0.1% TFA) in 7 min+2 min 100% CH$_3$CN (0.1% TFA); detection at 215 nm, flow rate 1 mL/min at 30° C. Column: Nucleosil 100-3 C8 HD (125×4 mm).

Synthetic Scheme 1 (Examples 1 and 2):
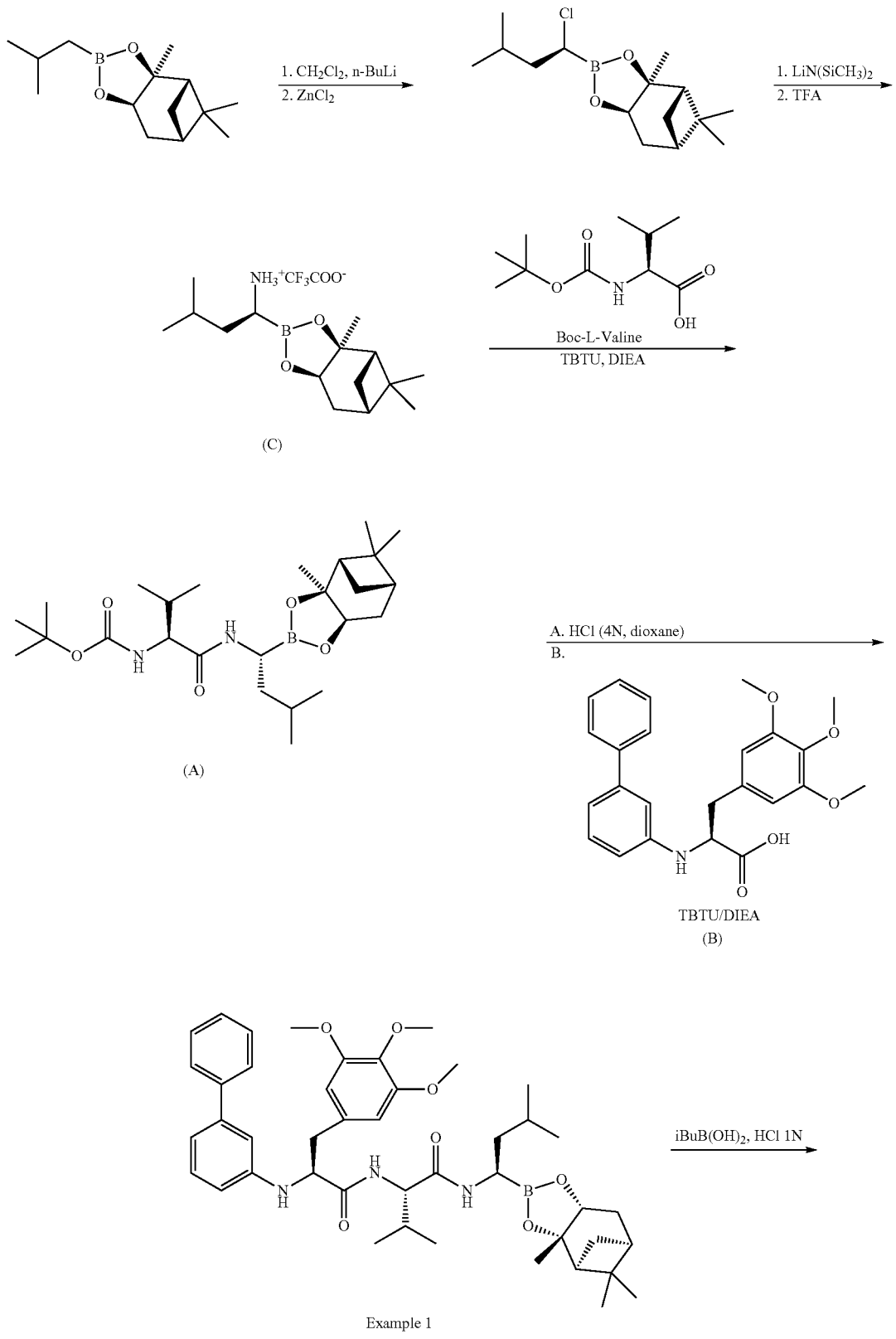
Example 1

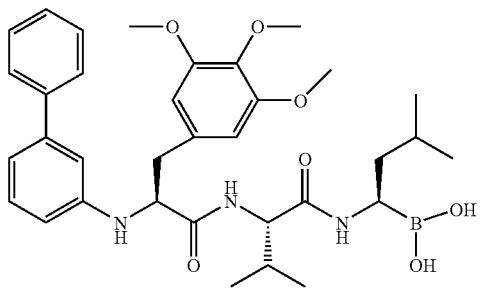

Example 2

Example 1

(S)-2-[(S)-2-(Biphenyl-3-ylamino)-3-(3,4,5-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide Step A: A 4N solution of HCl in dioxane (5.7 mL, 22.77 mMol, 30 equiv) is added to a cold (0° C.) solution of {(S)-2-Methyl-1-[(R)-3-methyl-1-(1S,2S,6R,8S)-2,9,9-trimethyl-3,5-dioxa4-bora-tricyclo[6.1.1.0$^{2,6}$]dec4-yl)-butylcarbamoyl]-propyl}-carbamic acid tert-butyl ((A) in Synthetic Scheme 1) (0.352 g, 0.759 mMol) in CH$_2$Cl$_2$ abs. (5.5 mL), under an argon atmosphere. The resulting mixture is allowed to warm to rt and stirred for 10 min. Additional 4N HCl (1.9 mL, 7.59 mMol, 10 equiv) is added. The reaction mixture is stirred for 10 min and concentrated to afford the crude hydrochloride as a yellow foam.

Step B: DIEA abs. (0.72 mL, 4.14 mMol, 5 equiv) is added dropwise (1.9 mL/min) to a cold (0° C.) solution of the crude hydrochloride (0.331 g, 0.828 mMol), (S)-2-(Biphenyl-3-ylamino)-3-(3,4,5-trimethoxy-phenyl)-propionic acid ((B) in Synthetic Scheme 1) (0.518 g, 0.994 mMol, 1.2 equiv), and TBTU (0.292 g, 0.910 mMol, 1.1 equiv) in DMF abs. (3.0 mL), under an argon atmosphere. The reaction mixture is allowed to warm to rt, stirred for 40 min and poured onto 0° C. H$_2$O (45 mL). The resulting precipitate is collected by vacuum filtration, dissolved in EtOAc and washed with H$_2$O. The organic phase is dried (Na$_2$SO$_4$), filtered and concentrated. The residue is purified by silica gel (25 g) column chromatography (CH$_2$Cl$_2$/MeOH, 90/10) to afford the title compound as a yellow foam.

Title compound: ES-MS: 754.2 [M+H]$^+$; HPLC: single peak at t$_R$=11.85 min (System 1); R$_f$=0.72 (CH$_2$Cl$_2$/MeOH, 90/10).

The starting materials are prepared as follows:

(a) (S)-2-(Biphenyl-3-ylamino)-3-(3,4,5-trimethoxy-phenyl)-propionic acid (for Step B)

The title compound is prepared by heating a suspension of 3-bromo-biphenyl (1.47 mL, 8.54 mMol, Aldrich 25,538-6), (S)-2-amino-3-(3,4,5-trimethoxy-phenyl)-propionic acid (3,4,5-OCH$_3$-phe-OH) (3.27 g, 12.81 mMol), K$_2$CO$_3$ (1.18 g, 8.54 mMol) and CuI (163 mg, 0.854 mMol) in DMF abs. (10.6 mL) for 24 h at 90° C., under an argon atmosphere. The resulting mixture is allowed to cool to rt, then concentrated in vacuo and purified by MPLC (CH$_3$CN/H$_2$O/TFA) to afford the title compound.

Title compound: ES-MS: 408.2 [M+H]$^+$; HPLC: single peak at t$_R$=8.86 min (System 1).

(b) (S)-2-Amino-3-(3,4,5-trimethoxy-phenyl)-propionic acid (L-3,4,5-Trimethoxy-phenyl-alanine)

The title compound is prepared from commercially available 3,4,5-trimethoxybenzaldehyde and N-acetylglycine according to a literature procedure (E.M. Oltz, R. C. Bruening, M. J. Smith, K. Kustin and K. Nakanishi in *J. Am. Chem.* 1998, 110 (18), 6162-6172). The resolution of the racemic N-acetyl-3,4,5-trimethoxy-phenylalanine methyl ester is performed by enzyme-catalyzed hydrolysis of the L-ester using Alcalase® (Novo Nordisk) as described in the literature (J. J. Nestor, Jr., T. L. Ho, R. A. Simpson, B. L. Horner, G. H. Jones, G. I. McRae and B. H. Vickery in *J. Med. Chem.* 1982, 25 (7), 795-801; or O. D. Tyagi & P. M. Boll in *Indian J. Chem.* 1992, pp. 851-854).

Title compound: [α]$_D^{20}$=−18.9° (c=1.025, H$_2$O); ES-MS: 256.1 [M+H]$^+$; HPLC: single peak at t$_R$=2.08 min (System 2).

(c) {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester The title compound is prepared as described in step B of example 1 but using (S)-3-Methyl-1-((1S,2S,6R,8S)-2,9,9-trimethyl-3,5-dioxa-4-bora-tricyclo[6.1.1.0$^{2,6}$]dec-4-yl)-butylammonium trifluoroacetate ((C) in Synthetic Scheme 1) (for preparation see Kettner, C. A. and Shenvi, A. B. *J. Biol. Chem.* 1984, 259, p. 15106-15114 and Matteson, D. S. and Sadhu, K. M. *J. Am. Chem. Soc.* 1981, 103, p. 5241-5242) (2.395 g, 6.32 mMol), Boc-L-valine (1.373 g, 6.32 mMol), TBTU (2.23 g, 6.95 mMol, 1.1 equiv), DIEA (3.3 mL, 18.95 mMol, 3.0 equiv) and DMF (24 mL).

Title compound: ES-MS: 465.1 [M+H]$^+$; HPLC: single peak at t$_R$=9.95 min (System 1).

Example 2

(R)-1-{(S)-2-[(S)-2-(Biphenyl-3-ylamino)-3-(3,4,5-trimethoxy-phenyl)-propionylamino]-3-methyl-butyrylamino}-3-methyl-butylboronic acid i-BuB(OH)$_2$ is added to a mixture of (S)-2-[(S)-2-(Biphenyl-3-ylamino)-3-(3,4,5-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0²,⁶]dec-4-yl)-butyl]-butyramide, methanol (4.3 mL), hexane (4.3 mL) and 1N HCl (1.45 mL). The reaction mixture is stirred for 2 h at rt and then diluted with methanol (8 mL) and hexane (8 mL). The two layers are separated. The methanol layer is washed twice with hexane, diluted with CH$_2$Cl$_2$, washed with H$_2$O, dried (Na$_2$SO$_4$), filtered and concentrated. The residue is dissolved in CH$_2$Cl$_2$ and purified by silica gel (20 g) column chromatography (CH$_2$Cl$_2$/MeOH, 80/20) to afford the title compound as a pale yellow foam.

Title compound: ES-MS: 618.2 [M−H]⁻; R$_f$=0.03 (CH$_2$Cl$_2$/MeOH, 95/5).

Synthetic Scheme 2 (Examples 3 and 4):

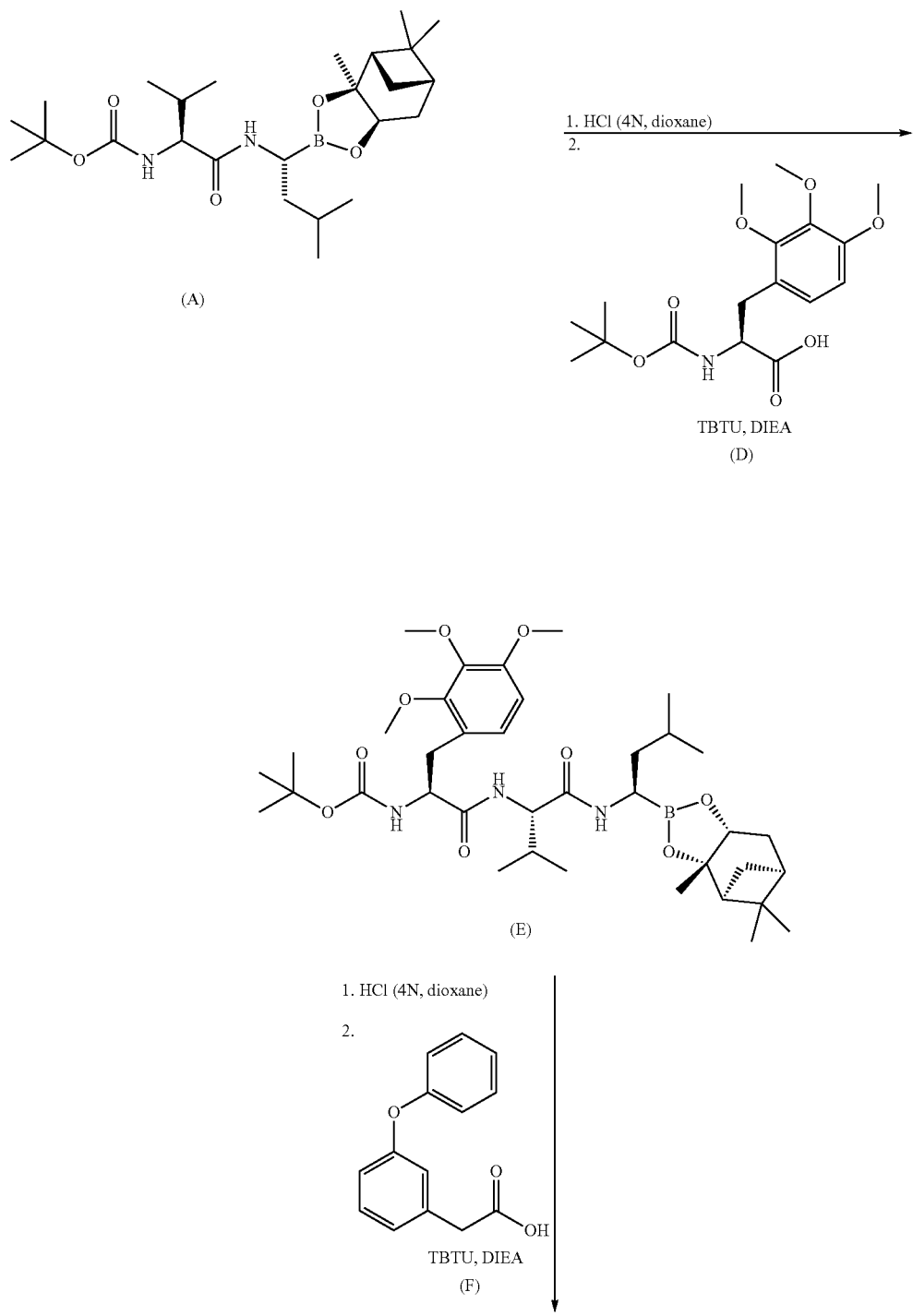

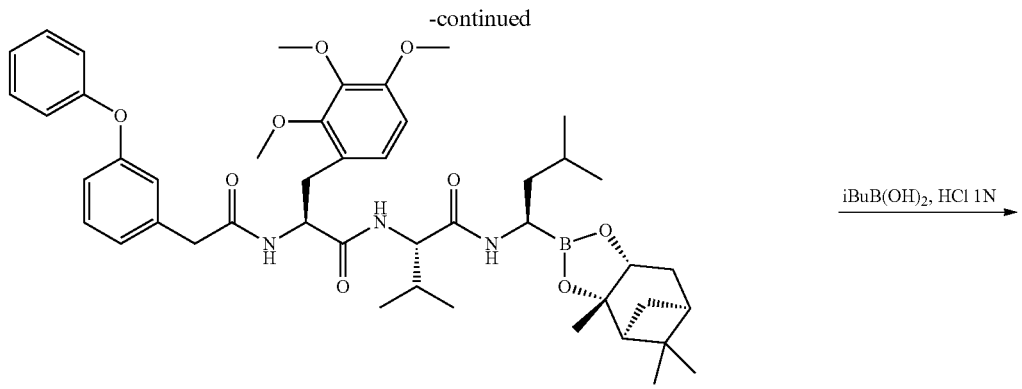

Example 3 iBuB(OH)₂, HCl 1N

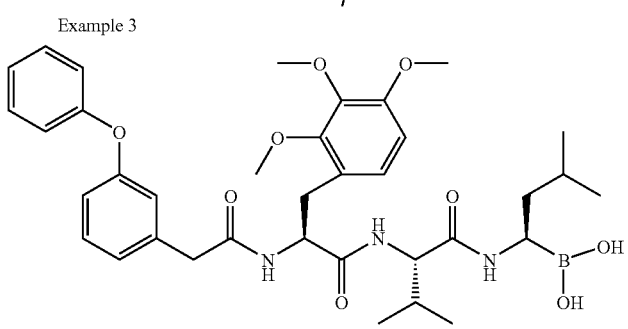

Example 4

Example 3

(S)-3-Methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-2-[(S)-2-[2-(3-phenoxy-phenyl)-acetylamino]-3-(2,3,4-trimethoxy-phenyl)-propionylamino]-butyramide The title compound is prepared from {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester ((A) in Synthetic Scheme 2) by reiteration of the 2-step (deprotection/coupling) procedure described in example 1 but using (S)-2-tert-Butoxycarbonylamino-3-(2,3,4-trimethoxy-phenyl)-propionic acid ((D) in Synthetic Scheme 2) and (3-Phenoxy-phenyl)-acetic acid ((F) in Synthetic Scheme 2) (Trans World Chemicals, Inc.; Rockville, Md., USA) as the partners in each coupling reaction (step B, example 1), respectively. The title compound is obtained as a white solid.

Title compound: ES-MS: 812.1 [M+H]⁺; HPLC: single peak at t$_R$=11.13 min (System 1); R$_f$=0.41 (CH₂Cl₂/MeOH, 95/5).

Step 3.1: (S)-2-Amino-3-(2,3,4-trimethoxy-phenyl)-propionic acid (L-2,3,4-Trimethoxy-phenyl-alanine)

The title compound is prepared as described for (S)-2-Amino-3-(3,4,5-trimethoxy-phenyl)-propionic acid (example 1).

Title compound: ES-MS: 256.1 [M+H]⁺; HPLC: t$_R$=2.54 min (System 2); [α]$_D^{20}$=−18.5° (c=0.99, H₂O).

Step 3.2: (S)-2-tert-Butoxycarbonylamino-3-(2,3,4-trimethoxy-phenyl)-propionic acid The title compound is synthesised starting from (S)-2-Amino-3-(2,3,4-trimethoxy-phenyl)-propionic acid according to a procedure known in the art (M. Bodanszky in Principles of Peptide Synthesis, Akad.-Verlag, 1984).

Title compound: ES-MS: 356.1 [M+H]⁺; HPLC: t$_R$=5.35 min (System 1); [α]$_D^{20}$=−2.5° (c=0.985, MeOH).

Example 4

(R)-3-Methyl-1-{(S)-3-methyl-2-[(S)-2-[2-(3-phenoxy-phenyl)-acetylamino]-3-(2,3,4-trimethoxy-phenyl)-propionylamino]-butyrylamino}-butylboronic acid The title compound is prepared as described in example 2; ES-MS: 676.0 [M−H]⁻; R$_f$=0.025 (CH₂Cl₂/MeOH, 95/5).

Example 5

(S)-3-Methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-2-[(S)-2-(3-phenyl-propionyl-amino)-3-(2,3,4-trimethoxy-phenyl)-propionylamino]-butyramide The title compound is prepared from {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester by reiteration of the 2-step (deprotection/coupling) procedure described in example 1 but using (S)-2-(tert-butyloxycarbonyl-amino)-3-(2,3,4-trimethoxy-phenyl)-propionic acid and 3-Phenyl-propionic acid (Fluka, Buchs, Switzerland) as the partners in each coupling reaction (step B, example 1), respectively.

Title compound: ES-MS: 734.1 [M+H]$^+$; HPLC: single peak at $t_R$=11.25 min (System 1); $R_f$=0.41 (CH$_2$Cl$_2$/MeOH, 95/5).

Example 6

(R)-3-Methyl-1-{(S)-3-methyl-2-[(S)-2-(3-phenyl-propionylamino)-3-(2,3,4-trimethoxy-phenyl)-propionylamino]-butyrylamino}-butylboronic acid The title compound is prepared as described in example 2; ES-MS: 598.2 [M–H]$^-$; $R_f$=0.025 (CH$_2$Cl$_2$/MeOH, 95/5).

Example 7

(S)-2-[(S)-2-(Biphenyl-3-ylamino)-3-(4-methoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared as described in example 1 but using (S)-2-(Biphenyl-3-ylamino)-3-(4-methoxy-phenyl)-propionic acid.

Title compound: ES-MS: 694.4 [M+H]$^+$; HPLC: single peak at $t_R$=12.01 min (System 1); $R_f$=0.56 (CH$_2$Cl$_2$/MeOH, 95/5).

Step 7.1: (S)-2-(Biphenyl-3-ylamino)-3-(4-methoxy-phenyl)-propionic acid

The title compound is prepared as described for (S)-2-(Biphenyl-3-ylamino)-3-(3,4,5-trimethoxy-phenyl)-propionic acid (example 1) but using O-methyl-L-tyrosine (Bachem). Purification by MPLC (CH$_3$CN/H$_2$O/TFA) afforded the title compound; ES-MS: 348.3 [M+H]$^+$; HPLC: single peak at $t_R$=9.52 min (System 1).

Example 8

(R)-1-{(S)-2-[(S)-2-(Biphenyl-3-ylamino)-3-(4-methoxy-phenyl)-propionylamino]-3-methyl-butyrylamino}-3-methyl-butylboronic acid The title compound is prepared as described in example 2; ES-MS: 558.0 [M–H]$^-$; HPLC: $t_R$=6.47 min (System 3); $R_f$=0.086 (CH$_2$Cl$_2$/MeOH, 95/5).

Example 9

(S)-2-[(S)-2-(Biphenyl-3-ylamino)-3-(3,4-dimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared as described in example 1 but using (S)-2-(Biphenyl-3-ylamino)-3-(3,4-dimethoxy-phenyl)-propionic acid.

Title compound: ES-MS: 724.4 [M+H]$^+$; HPLC: single peak at $t_R$=11.75 min (System 1); $R_f$=0.41 (CH$_2$Cl$_2$/MeOH, 95/5).

Step 9.1: (S)-2-(Biphenyl-3-ylamino)-3-(3,4-dimethoxy-phenyl)-propionic acid

The title compound is prepared as described for (S)-2-(Biphenyl-3-ylamino)-3-(3,4,5-trimethoxy-phenyl)-propionic acid (example 1) but using 3-(3,4-dimethoxyphenyl)-L-alanine (Aldrich). Purification by MPLC (CH$_3$CN/H$_2$O/TFA) afforded the title compound; ES-MS: 378.2 [M+H]$^+$; HPLC: single peak at $t_R$=9.10 min (System 1).

Example 10

(R)-1-{(S)-2-[(S)-2-(Biphenyl-3-ylamino)-3-(3,4-dimethoxy-phenyl)-propionylamino]-3-methyl-butyrylamino}-3-methyl-butylboronic acid The title compound is prepared as described in example 2; ES-MS: 588.2 [M–H]$^-$; $R_f$=0.090 (CH$_2$Cl$_2$/MeOH, 95/5).

Example 11

(S)-2-[(S)-2-(3-Isopropyl-phenylamino)-3-(3,4,5-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared as described in example 1 but using (S)-2-(3-Isopropyl-phenylamino)-3-(3,4,5-trimethoxy-phenyl)-propionic acid.

Title compound: ES-MS: 720.4 [M+H]$^+$; HPLC: single peak at $t_R$=11.85 min (System 1); $R_f$=0.43 (CH$_2$Cl$_2$/MeOH, 95/5).

Step 11.1: (S)-2-(3-Isopropyl-phenylaminoc-3-(3,4,5-trimethoxy-phenyl)-propionic acid The title compound is prepared as described for (S)-2-(Biphenyl-3-ylamino)-3-(3,4,5-trimethoxy-phenyl)-propionic acid (example 1) but using 1-bromo-3-isopropylbenzene (Lancaster). Purification by MPLC (CH$_3$CN/H$_2$O/TFA) afforded the title compound; ES-MS: 374.1 [M+H]$^+$; HPLC: single peak at $t_R$=8.95 min (System 1).

Example 12

(R)-1-{(S)-2-[(S)-2-(3-Isopropyl-phenylamino)-3-(3,4,5-trimethoxy-phenyl)-propionylamino]-3-methyl-butyrylamino}-3-methyl-butylboronic acid The title compound is prepared as described in example 2; ES-MS: 584.3 [M–H]$^-$; $R_f$=0.13 (CH$_2$Cl$_2$/MeOH, 95/5).

Example 13

(S)-3-Methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-2-[(S)-2-(3-pyridin-2-yl-phenylamino)-3-(3,4,5-trimethoxy-phenyl)-propionylamino]-butyramide The title compound is prepared as described in example 1 but using (S)-2-(3-Pyridin-2-yl-phenylamino)-3-(3,4,5-trimethoxy-phenyl)-propionic acid.

Title compound: ES-MS: 755.3 [M+H]$^+$; HPLC: single peak at $t_R$=9.97 min (System 1); $R_f$=0.23 (CH$_2$Cl$_2$/MeOH, 95/5).

Step 13.1: 2-(3-Bromo-phenyl)-pyridine

The title compound is prepared according to literature procedures: Zhang, Biliang, Breslow, Ronald *Ester Hydrolysis* by a Catalytic Cyclodextrin Dimer Enzyme Mimic with a Metallobipyridyl Linking Group. J. Am. Chem. Soc. (1997), 119(7), 1676-1681; M. Van der Sluis, V. Beverwijk, A. Termaten, F. Bickelhaupt, H. Kooijman, A. L. Spek *Synthesis of Novel Phosphaalkene-Based Bidentate Ligands Mes \*P: CH(3-R-Ar) (R=Pyridyl, Carbaldimino) and Formation of Three-Membered Palladacycles Mes \*(Me)P-CH(3-R-Ar)-PdCl by Carbopalladation of the P:C Double Bond*. Organometallics (1999), 18(8), 1402-1407.

Title compound: ES-MS: 235.0 [M+H]$^+$; HPLC: single peak at $t_R$=6.64 min (System 1); $R_f$=0.17 (Hexane/Et$_2$O, 80/20).

Step 13.2: (S)-2-(3-Pyridin-2-yl-phenylamino)-3-(3, 4,5-trimethoxy-phenyl)-propionic acid The title compound is prepared as described for (S)-2-(Biphenyl-3-ylamino)-3-(3,4,5-trimethoxy-phenyl)-propionic acid (example 1) but using 2-(3-Bromo-phenyl)-pyridine. Purification by MPLC (CH$_3$CN/H$_2$O/TFA) afforded the title compound; ES-MS: 409.2 [M+H]$^+$; HPLC: single peak at $t_R$=6.64 min (System 1).

Example 14

(R)-3-Methyl-1-{(S)-3-methyl-2-[(S)-2-(3-pyridin-2-yl-phenylamino)-3-(3,4,5-trimethoxy-phenyl)-propionylamino]-butyrylamino}-butylboronic acid The title compound is prepared as described in example 2; ES-MS: 619.2 [M−H]$^-$; $R_f$=0.044 (CH$_2$Cl$_2$/MeOH, 95/5).

Example 15

(S)-2-[(S)-2-(Biphenyl-3-ylamino)-3-(2,3,4-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared as described in example 1 but using (S)-2-(Biphenyl-3-ylamino)-3-(2,3,4-trimethoxy-phenyl)-propionic acid.

Title compound: ES-MS: 754.4 [M+H]$^+$; HPLC: single peak at $t_R$=12.08 min (System 1); $R_f$=0.66 (CH$_2$Cl$_2$/MeOH, 95/5).

Step 15.1: (S)-2-(Biphenyl-3-ylamino)-3-(2,3,4-trimethoxy-phenyl)-propionic acid The title compound is prepared as described for (S)-2-(Biphenyl-3-ylamino)-3-(3,4,5-trimethoxy-phenyl)-propionic acid (example 1) but using (S)-2-Amino-3-(2,3,4-trimethoxy-phenyl)-propionic acid. Purification by MPLC (CH$_3$CN/H$_2$O/TFA) afforded the title compound; ES-MS: 408.2 [M+H]$^+$; HPLC: single peak at $t_R$=9.42 min (System 1).

Example 16

(R)-1-{(S)-2-[(S)-2-(Biphenyl-3-ylamino)-3-(2,3,4-trimethoxy-phenyl)-propionylamino]-3-methyl-butyrylamino}-3-methyl-butylboronic acid The title compound is prepared as described in example 2; ES-MS: 618.3 [M−H]$^-$; $R_f$=0.23 (CH$_2$Cl$_2$/MeOH, 95/5).

Example 17

(S)-2-[(S)-3-(4-Benzyloxy-phenyl)-2-(biphenyl-3-ylamino)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared as described in example 1 but using (S)-3-(4-Benzyloxy-phenyl)-2-(biphenyl-3-ylamino)-propionic acid.

Title compound: ES-MS: 770.3 [M+H]$^+$; HPLC: single peak at $t_R$=12.45 min (System 1); $R_f$=0.74 (CH$_2$Cl$_2$/MeOH, 95/5).

Step 17.1: (S)-3-(4-Benzyloxy-phenyl)-2-(biphenyl-3-ylamino)-propionic acid

The title compound is prepared as described for (S)-2-(Biphenyl-3-ylamino)-3-(3,4,5-trimethoxy-phenyl)-propionic acid (example 1) but using (S)-2-Amino-3-(4-benzyloxy-phenyl)-propionic acid (O-benzyl-L-tyrosine). Purification by MPLC (CH$_3$CN/H$_2$O/TFA) afforded the title compound; ES-MS: 424.3 [M+H]$^+$; HPLC: single peak at $t_R$=10.40 min (System 1).

Example 18

(R)-1-{(S)-2-[(S)-3-(4-Benzyloxy-phenyl)-2-(biphenyl-3-ylamino)-propionylamino]-3-methyl-butyrylamino}-3-methyl-butylboronic acid The title compound is prepared as described in example 2; ES-MS: 633.9 [M−H]$^-$; $R_f$=0.65 (CH$_2$Cl$_2$/MeOH, 90/10).

Example 19

(R)-2-[(S)-2-(Biphenyl-3-ylamino)-3-(3,4,5-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared as described in example 1 but using {(R)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester.

Title compound: ES-MS: 754.1 [M+H]$^+$; HPLC: single peak at $t_R$=11.73 min (System 1); $R_f$=0.52 (CH$_2$Cl$_2$/MeOH, 95/5).

Step 19.1: {(R)-2-Methyl-1-[(R)-3-methyl-1-((1S, 2S,6R,8S)-2,9,9-trimethyl-3,5-dioxa-4-bora-tricyclo [6.1.1.0$^{2,6}$]dec-4-yl)-butylcarbamoyl]-propyl}-carbamic acid tert-butyl ester The title compound is prepared as described for {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester (example 1 (c)) but using Boc-D-valine (Fluka).

Title compound: ES-MS: 465.4 [M+H]$^+$.

Example 20

(R)-1-{(R)-2-[(S)-2-(Biphenyl-3-ylamino)-3-(3,4,5-trimethoxy-phenyl)-propionylamino]-3-methyl-butyrylamino}-3-methyl-butylboronic acid The title compound is prepared as described in example 2; ES-MS: 618.2 [M−H]$^-$; $R_f$=0.088 (CH$_2$Cl$_2$/MeOH, 95/5).

Example 21

(S)-2-[(R)-2-(Biphenyl-3-ylamino)-3-(3,4,5-trimethoxy-phenyl)-propionylamino]-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared as described in example 1 but using (R)-2-(Biphenyl-3-ylamino)-3-(3,4,5-trimethoxy-phenyl)-propionic acid.
Title compound: ES-MS: 754.3 [M+H]$^+$; HPLC: single peak at $t_R$=11.71 min (System 1); $R_f$=0.67 (CH$_2$Cl$_2$/MeOH, 95/5).

Step 21.1: (R)-2-(Biphenyl-3-ylamino)-3-(3,4,5-trimethoxy-phenyl)-propionic acid The title compound is prepared as described for (S)-2-(Biphenyl-3-ylamino)-3-(3,4,5-trimethoxy-phenyl)-propionic acid (example 1) but using (R)-2-amino-3-(3,4,5-trimethoxy-phenyl)-propionic acid (3,4,5-OCH$_3$-phe-OH).
Title compound: ES-MS: 408.2 [M+H]$^+$; HPLC: single peak at $t_R$=9.10 min (System 1).
For the synthesis of (R)-2-amino-3-(3,4,5-trimethoxy-phenyl)-propionic acid see example 1.
After the enzymatic resolution, the remaining D-aminoacid-methylester is hydrolysed and deacetylated using protocols known in the art; $[\alpha]_D^{20}$=+19.7° (c=1.04, H$_2$O); ES-MS: 256.2 [M+H]$^+$; single peak at $t_R$=2.11 min (System 2).

Example 22

(R)-1-{(S)-2-[(R)-2-(Biphenyl-3-ylamino)-3-(3,4,5-trimethoxy-phenyl)-propionylamino]-3-methyl-butyrylamino}-3-methyl-butylboronic acid The title compound is prepared as described in example 2; ES-MS: 618.2 [M−H]$^-$; $R_f$=0.20 (CH$_2$Cl$_2$/MeOH, 90/10).

Example 23

(S)-2-[(S)-2-(Biphenyl-3-ylamino)-3-(3,4,5-trimethoxy-phenyl)-propionylamino]-3-methyl-N-[3-methyl-1-(4,4,5,5-tetramethyl-[1,3,2]dioxaborolan-2-yl)-butyl]-butyramide The title compound is prepared as described in example 1 but using {(S)-2-Methyl-1-[3-methyl-1-(4,4,5,5-tetramethyl-[1,3,2]dioxaborolan-2-yl)-butylcarbamoyl]-propyl}-carbarnic acid tert-butyl ester.
The title compound is obtained as a crude product; ES-MS: 702.3 [M+H]$^+$; HPLC: $t_R$=10.31 min (System 1).

Step 23.1: {(S)-2-Methyl-1-[3-methyl-1-(4,4,5,5-tetramethyl-[1,3,2]dioxaborolan-2-yl)-butylcarbamoyl]-propyl}-carbamic acid tert-butyl ester The title compound is prepared in analogy to the synthesis of {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester (example 1 (c)).
Title compound: ES-MS: 413.3 [M+H]$^+$.

Example 24

1-{(S)-2-[(S)-2-(Biphenyl-3-ylamino)-3-(3,4,5-trimethoxy-phenyl)-propionylamino]-3-methyl-butyrylamino}-3-methyl-butylboronic acid The title compound is prepared as described in example 2; ES-MS: 618.2 [M−H]$^-$; $R_f$=0.076 (CH$_2$Cl$_2$/MeOH, 95/5); HPLC: two peaks at $t_R$=6.23 min and 6.36 min (ratio 1:1) (System 3).

Example 25

(S)-2-{(S)-3-(3,4-Dimethoxy-phenyl)-2-[2-(3-phenoxy-phenyl)-acetylamino]-propionylamino}-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared from {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester by reiteration of the 2-step (deprotection/coupling) procedure described in example 1 but using Boc-L-3,4-dimethoxyphenylalanine (Synthetech) and (3-Phenoxy-phenyl)-acetic acid (Trans World Chemicals, Inc.; Rockville, Md., USA) as the partners in each coupling reaction (step B, example 1), respectively. The title compound is obtained as a foam; ES-MS: 782.3 [M+H]$^+$; HPLC: single peak at $t_R$=11.76 min (System 1); $R_f$=0.61 (CH$_2$Cl$_2$/MeOH, 90/10).

Example 26

(R)-1-((S)-2-{(S)-3-(3,4-Dimethoxy-phenyl)-2-[2-(3-phenoxy-phenyl)-acetylamino]-propionylamino}-3-methyl-butyrylamino)-3-methyl-butylboronic acid The title compound is prepared as described in example 2; ES-MS: 646.2 [M−H]$^-$; HPLC: single peak at $t_R$=5.90 min (System 3); $R_f$=0.12 (CH$_2$Cl$_2$/MeOH, 90/10).

Example 27

(S)-3-Methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-2-[(S)-2-[2-(3-phenoxy-phenyl)-acetylamino]-3-(3,4,5-trimethoxy-phenyl)-propionylamino]-butyramide The title compound is prepared from {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester by reiteration of the 2-step (deprotection/coupling) procedure described in example 1 but using (S)-2-tert-Butoxycarbonylamino-3-(3,4,5-trimethoxy-phenyl)-propionic acid and (3-Phenoxy-phenyl)-acetic acid (Trans World Chemicals, Inc.; Rockville, Md., USA) as the partners in each coupling reaction (step B, example 1), respectively. The title compound is obtained as a yellow foam; ES-MS: 812.4 [M+H]$^+$; HPLC: single peak at $t_R$=11.36 min (System 1); $R_f$=0.53 (CH$_2$Cl$_2$/MeOH, 95/5).

Step 27.1: (S)-2-tert-Butoxycarbonylamino-3-(3,4,5-trimethoxy-phenyl)-propionic acid The title compound is synthesised as described for (S)-2-tert-Butoxycarbonylamino-3-(2,3,4-trimethoxy-phenyl)-propionic acid (Example 3) but starting from (S)-2-Amino-3-(3,4,5-trimethoxy-phenyl)-propionic acid.

Title compound: ES-MS: 356 [M+H]$^+$; HPLC: $t_R$=4.83 min (System 2); m.p.=76-80° C.; $[\alpha]_D^{20}$=+13.4° (c=1.01, methanol).

Example 28

(R)-3-Methyl-1-{(S)-3-methyl-2-[(S)-2-[2-(3-phenoxy-phenyl)-acetylamino]-3-(3,4,5-trimethoxy-phenyl)-propionylamino]-butyrylamino}-butylboronic acid The title compound is prepared as described in example 2; ES-MS: 676.2 [M−H]$^-$; $R_f$=0.14 (CH$_2$Cl$_2$/MeOH, 95/5).

Example 29

(S)-2-{(S)-3-(4-Benzyloxy-phenyl)-2-[2-(3-benzyloxy-phenyl)-acetylamino]-propionylamino}-3-methyl-N-[(R)-3-methyl-1-((1S,2S,6R,8S)-2,9,9-trimethyl-3,5-dioxa-4-bora-tricyclo[6.1.1.0$^{2,6}$]dec-4-yl)-butyl]-butyramide The title compound is prepared from {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester by reiteration of the 2-step (deprotection/coupling) procedure described in example 1 but using (S)-3-(4-Benzyloxy-phenyl)-2-tert-butoxycarbonylamino-propionic acid and (3-Phenoxy-phenyl)-acetic acid (Trans World Chemicals, Inc.; Rockville, Md., USA) as the partners in each coupling reaction (step B, example 1), respectively. The title compound is obtained as a beige foam; ES-MS: 842.0 [M+H]$^+$; HPLC: single peak at $t_R$=12.19 min (System 1); $R_f$=0.37 (CH$_2$Cl$_2$/MeOH, 95/5).

Step 29.1: (S)-3-(4-Benzyloxy-phenyl)-2-tert-butoxycarbonylamino-propionic acid

The title compound is synthesised as described for (S)-2-tert-Butoxycarbonylamino-3-(2,3,4-trimethoxy-phenyl)-propionic acid (Example 3) but starting from O-Benzyl-L-tyrosine (Fluka).

Title compound: ES-MS: 370.1 [M−H]$^-$; HPLC: $t_R$=9.23 min (System 1).

Example 30

(R)-1-((S)-2-{(S)-3-(4-Benzyloxy-phenyl)-2-[2-(3-benzyloxy-phenyl)-acetylamino]-propionylamino}-3-methyl-butyrylamino)-3-methyl-butylboronic acid The titled compound is prepared as described in example 2; ES-MS: 705.8 [M−H]$^-$; $R_f$=0.12 (CH$_2$Cl$_2$/MeOH, 95/5).

Example 31

(S)-2-[(S)-2-(Biphenyl-3-ylamino)-3-(3,4,5-trimethoxy-phenyl)-propionylamino]-4-methyl-pentanoic acid [(R)-3-methyl-1-((1S,2S,6R,8S)-2,9,9-trimethyl-3,5-dioxa-4-bora-tricyclo[6.1.1.0$^{2,6}$]dec-4-yl)-butyl]-amide The title compound is prepared as described in example 1 but using {(S)-3-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-butyl}-carbamic acid tert-butyl ester.

Title compound: ES-MS: 768.2 [M+H]$^+$; HPLC: single peak at $t_R$=11.79 min (System 1); $R_f$=0.72 (CH$_2$Cl$_2$/MeOH, 95/5).

Step 31.1: {(S)-3-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-butyl}-carbamic acid tert-butyl ester The title compound is prepared as described for {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester (example 1 (c)) but using Boc-L-leucine.

Title compound: ES-MS: 479.2 [M+H]$^+$; HPLC: single peak at $t_R$=10.05 min (System 1).

Example 32

(R)-1-{(S)-2-[(S)-2-(Biphenyl-3-ylamino)-3-(3,4,5-trimethoxy-phenyl)-propionylamino]-4-methyl-pentanoylamino}-3-methyl-butylboronic acid The title compound is prepared as described in example 2; ES-MS: 632.2 [M−H]$^-$; $R_f$=0.15 (CH$_2$Cl$_2$/MeOH, 95/5).

Example 33

(S)-2-[(S)-2-(Biphenyl-3-ylamino)-3-(3,4-dimethoxy-phenyl)-propionylamino]-4-methyl-pentanoic acid [(R)-3-methyl-1-((1S,2S,6R,8S)-2,9,9-trimethyl-3,5-dioxa-4-bora-tricyclo[6.1.1.0$^{2,6}$]dec-4-yl)-butyl]-amide The title compound is prepared as described in example 1 but using {(S)-3-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-butyl}-carbamic acid tert-butyl ester and (S)-2-(Biphenyl-3-ylamino)-3-(3,4-dimethoxy-phenyl)-propionic acid.

Title compound: ES-MS: 738.3 [M+H]$^+$; HPLC: single peak at $t_R$=11.76 min (System 1); $R_f$=0.59 (CH$_2$Cl$_2$/MeOH, 95/5).

Example 34

(R)-1-{(S)-2-[(S)-2-(Biphenyl-3-ylamino)-3-(3,4,5-trimethoxy-phenyl)-propionylamino]-4-methyl-pentanoylamino}-3-methyl-butylboronic acid The title compound is prepared as described in example 2; ES-MS: 602.2 [M−H]$^-$; $R_f$=0.14 (CH$_2$Cl$_2$/MeOH, 95/5).

Example 35

(S)-2-[(S)-2-(Biphenyl-3-ylamino)-3-(4-methoxy-phenyl)-propionylamino]-4-methyl-pentanoic acid [(R)-3-methyl-1-((1S,2S,6R,8S)-2,9,9-trimethyl-3,5-dioxa-4-bora-tricyclo[6.1.1.0$^{2,6}$]dec-4-yl)-butyl]-amide The title compound is prepared as described in example 1 but using {(S)-3-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-butyl}-carbamic acid tert-butyl ester and (S)-2-(Biphenyl-3-ylamino)-3-(4-methoxy-phenyl)-propionic acid.

Title compound: ES-MS: 708.3 [M+H]$^+$; HPLC: single peak at $t_R$=12.03 min (System 1); $R_f$=0.70 (CH$_2$Cl$_2$/MeOH, 95/5).

Example 36

(R)-1-{(S)-2-[(S)-2-(Biphenyl-3-ylamino)-3-(4-methoxy-phenyl)-propionylamino]-4-methyl-pentanoylamino}-3-methyl-butylboronic acid The title compound is prepared as described in example 2; ES-MS: 572.1 [M−H]$^-$; $R_f$=0.25 (CH$_2$Cl$_2$/MeOH, 90/10).

Example 37

(S)-2-(Biphenyl-3-ylamino)-N-{(S)-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-3-(3,4,5-trimethoxy-phenyl)-propionamide The title compound is prepared as described in example 1 but using {(S)-1-[(R)-3-Methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-carbamic acid tert-butyl ester.

Title compound: ES-MS: 726.3 [M+H]$^+$; HPLC: single peak at $t_R$=11.24 min (System 1); $R_f$=0.41 (CH$_2$Cl$_2$/MeOH, 95/5).

Step 37.1: {(S)-1-[(R)-3-Methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-carbamic acid tert-butyl ester The title compound is prepared as described for {(S)-2-Methyl-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-propyl}-carbamic acid tert-butyl ester (step 1.1, example 1) but using Boc-L-alanine (Fluka).

Title compound: ES-MS: 437.4 [M+H]$^+$; HPLC: single peak at $t_R$=10.91 min (System 1).

Example 38

(R)-1-{(S)-2-[(S)-2-(Biphenyl-3-ylamino)-3-(3,4,5-trimethoxy-phenyl)-propionylamino]-propionylamino}-3-methyl-butylboronic acid The title compound is prepared as described in example 2; ES-MS: 590.0 [M−H]$^-$; $R_f$=0.12 (CH$_2$Cl$_2$/MeOH, 95/5).

Example 39

(S)-2-(Biphenyl-3-ylamino)-N-{(S)-1-[(R)-3-methyl-1-((1S,2S6R,8S)-2,9,9-trimethyl-3,5-dioxa-4-bora-tricyclo[6.1.1.0$^{2,6}$]dec-4-yl)-butylcarbamoyl]-ethyl}-3-(2,3,4-trimethoxy-phenyl)-propionamide The title compound is prepared as described in example 1 but using {(S)-1-[(R)-3-Methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-carbamic acid tert-butyl ester and (S)-2-(Biphenyl-3-ylamino)-3-(2,3,4-trimethoxy-phenyl)-propionic acid.

Title compound: ES-MS: 726.3 [M+H]$^+$; HPLC: single peak at $t_R$=11.71 min (System 1); $R_f$=0.45 (CH$_2$Cl$_2$/MeOH, 95/5).

Example 40

(R)-1-{(S)-2-[(S)-2-(Biphenyl-3-ylamino)-3-(2,3,4-trimethoxy-phenyl)-propionylamino]-propionylamino}-3-methyl-butylboronic acid The title compound is prepared as described in example 2; ES-MS: 590.0 [M−H]$^-$; $R_f$=0.033 (CH$_2$Cl$_2$/MeOH, 95/5).

Example 41

(S)-2-(Biphenyl-3-ylamino)-3-(4-methoxy-phenyl)-N-{(S)-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-propionamide The title compound is prepared as described in example 1 but using {(S)-1-[(R)-3-Methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-carbamic acid tert-butyl ester and (S)-2-(Biphenyl-3-ylamino)-3-(4-methoxy-phenyl)-propionic acid.

Title compound: ES-MS: 666.3 [M+H]$^+$; HPLC: single peak at $t_R$=11.63 min (System 1); $R_f$=0.46 (CH$_2$Cl$_2$/MeOH, 95/5).

Example 42

(R)-1-{(S)-2-[(S)-2-(Biphenyl-3-ylamino)-3-(4-methoxy-phenyl)-propionylamino]-propionylamino}-3-methyl-butylboronic acid The title compound is prepared as described in example 2; ES-MS: 530.3 [M−H]$^-$; $R_f$=0.051 (CH$_2$Cl$_2$/MeOH, 95/5).

Example 43

(S)-2-(Biphenyl-3-ylamino)-3-(3,4-dimethoxy-phenyl)-N-{(S)-1-[(R)-3-methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-propionamide The title compound is prepared as described in example 1 but using {(S)-1-[(R)-3-Methyl-1-((1S,2S,6R,8S)-2,9,9-trimethyl-3,5-dioxa-4-bora-tricyclo[6.1.1.0$^{2,6}$]dec-4-yl)-butylcarbamoyl]-ethyl}-carbamic acid tert-butyl ester and (S)-2-(Biphenyl-3-ylamino)-3-(3,4-dimethoxy-phenyl)-propionic acid.

Title compound: ES-MS: 696.3 [M+H]⁺; HPLC: single peak at $t_R$=11.39 min (System 1); $R_f$=0.53 (CH$_2$Cl$_2$/MeOH, 95/5).

Example 44

(R)-1-{(S)-2-[(S)-2-(Biphenyl-3-ylamino)-3-(3,4-dimethoxy-phenyl)-propionylamino]-propionylamino}-3-methyl-butylboronic acid The title compound is prepared as described in example 2; ES-MS: 560.2 [M−H]⁻; $R_f$=0.023 (CH$_2$Cl$_2$/MeOH, 95/5).

Example 45

(S)-2-(3-Isopropyl-phenylamino)-N-{(S)-1-[(R)-3-methyl-1-((1S,2S,6R,8S)-2,9,9-trimethyl-3,5-dioxa-4-bora-tricyclo[6.1.1.0²,⁶]dec-4-yl)-butylcarbamoyl]-ethyl}-3-(3,4,5-trimethoxy-phenyl)-propionamide The title compound is prepared as described in example 1 but using {(S)-1-[(R)-3-Methyl-1-((1S,2S,6R,8S)-2,9,9-trimethyl-3,5-dioxa-4-bora-tricyclo[6.1.1.0²,⁶]dec-4-yl)-butylcarbamoyl]-ethyl}-carbamic acid tert-butyl ester and (S)-2-(3-Isopropyl-phenylamino)-3-(3,4,5-trimethoxy-phenyl)-propionic acid.

Title compound: ES-MS: 692.3 [M+H]⁺; HPLC: single peak at $t_R$=11.49 min (System 1); $R_f$=0.24 (CH$_2$Cl$_2$/MeOH, 95/5).

Example 46

(R)-1-{(S)-2-[(S)-2-(3-Isopropyl-phenylamino)-3-(3,4,5-trimethoxy-phenyl)-propionylamino]-propionylamino}-3-methyl-butylboronic acid The title compound is prepared as described in example 2; ES-MS: 560.2 [M−H]⁻; $R_f$=0.22 (CH$_2$Cl$_2$/MeOH, 95/5).

Example 47

(S)-N-{(S)-1-[(R)-3-Methyl-1-((1S,2S,6R,8S)-2,9,9-trimethyl-3,5-dioxa-4-bora-tricyclo[6.1.1.0²,⁶]dec-4-yl)-butylcarbamoyl]-ethyl}-2-(3-phenyl-propionylamino)-3-(2,3,4-trimethoxy-phenyl)-propionamide The title compound is prepared from {(S)-1-[(R)-3-Methyl-1-((1S,2S,6R,8S)-2,9,9-trimethyl-3,5-dioxa-4-bora-tricyclo[6.1.1.0²,⁶]dec-4-yl)-butylcarbamoyl]-ethyl}-carbamic acid tert-butyl ester by reiteration of the 2-step (deprotection/coupling) procedure described in example 1 but using (S)-2-Amino-3-(2,3,4-trimethoxy-phenyl)-propionic acid and 3-Phenyl-propionic acid (Fluka) as the partners in each coupling reaction (step B, example 1), respectively.

Title compound: ES-MS: 706.3 [M+H]⁺; HPLC: single peak at $t_R$=10.81 min (System 1); $R_f$=0.32 (CH$_2$Cl$_2$/MeOH, 95/5).

Example 48

(R)-3-Methyl-1-{(S)-2-[(S)-2-(3-phenyl-propionylamino)-3-(2,3,4-trimethoxy-phenyl)-propionylamino]-propionylamino}-butylboronic acid The title compound is prepared as described in example 2; ES-MS: 570.3 [M−H]⁻; $R_f$=0.22 (CH$_2$Cl$_2$/MeOH, 95/5).

Example 49

(S)-2-[(S)-2-(Biphenyl-3-ylamino)-3-(3,4,5-trimethoxy-phenyl)-propionylamino]-3-methyl-N-[(R)-2-phenyl-1-((1S,2S,6R,8S)-2,9,9-trimethyl-3,5-dioxa-4-bora-tricyclo[6.1.1.0²,⁶]dec-4-yl)-ethyl]-butyramide The title compound is prepared as described in example 1 but using {(S)-2-Methyl-1[(R)-2-phenyl-1-((1S,2S,6R,8S)-2,9,9-trimethyl-3,5-dioxa-4-bora-tricyclo[6.1.1.0²,⁶]dec-4-yl)-ethylcarbamoyl]-propyl}-carbamic acid tert-butyl ester.

Title compound: ES-MS: 788.0 [M+H]⁺; HPLC: single peak at $t_R$=11.66 min (System 1); $R_f$=0.79 (CH$_2$Cl$_2$/MeOH, 95/5).

Step 49.1: {(S)-2-Methyl-1-[(R)-2-phenyl-1-((1S,2S,6R,8S)-2,9,9-trimethyl-3,5-dioxa-4-bora-tricyclo[6.1.1.0²,⁶]dec-4-yl)-ethylcarbamoyl]-propyl}-carbamic acid tert-butyl ester The title compound is prepared in analogy to the synthesis of {(S)-2-Methyl-1-[(R)-3-methyl-1-((1S,2S,6R,8S)-2,9,9-trimethyl-3,5-dioxa-4-bora-tricyclo[6.1.1.0²,⁶]dec-4-yl)-butylcarbamoyl]-propyl}-carbamic acid tert-butyl ester (example 1 (c)).

Title compound: ES-MS: 499.1 [M+H]⁺; HPLC: single peak at $t_R$=10.78 min (System 1).

Example 50

(R)-1-{(S)-2-[(S)-2-(Biphenyl-3-ylamino)-3-(3,4,5-trimethoxy-phenyl)-propionylamino]-3-methyl-butyrylamino}-2-phenyl-ethylboronic acid The title compound is prepared as described in example 2; ES-MS: 652.2 [M−H]⁻; $R_f$=0.22 (CH$_2$Cl$_2$/MeOH, 95/5).

Example 51

(S)-2-[(S)-2-(Biphenyl-3-ylamino)-3-(4-methoxy-phenyl)-propionylamino]-3-methyl-N-[(R)-2-phenyl-1-((1S,2S,6R,8S)-2,9,9-trimethyl-3,5-dioxa-4-bora-tricyclo[6.1.1.0²,⁶]dec4-yl)-ethyl]-butyramide The title compound is prepared as described in example 1 but using {(S)-2-Methyl-1-[(R)-2-phenyl-1-((1S,2S,6R,8S)-2,9,9-trimethyl-3,5dioxa-4-bora-tricyclo[6.1.1.0²,⁶]dec-4-yl)-ethylcarbamoyl]-propyl}-carbamic acid tert-butyl ester and (S)-2-(Biphenyl-3-ylamino)-3-(4-methoxy-phenyl)-propionic acid.

Title compound: ES-MS: 727.9 [M+H]⁺; HPLC: single peak at $t_R$=11.87 min (System 1); $R_f$=0.73 (CH$_2$Cl$_2$/MeOH, 95/5).

Example 52

(R)-1-{(S)-2-[(S)-2-(Biphenyl-3-ylamino)-3-(4-methoxy-phenyl)-propionylamino]-3-methyl-butyrylamino}-2-phenyl-ethylboronic acid The title compound is prepared as described in example 2; ES-MS: 591.8 [M−H]⁻; $R_f$=0.13 (CH$_2$Cl$_2$/MeOH, 95/5).

Example 53

Inhibition of the Chymotrypsin-Like activity of the 20S Proteasome

Exemplary $IC_{50}$ values determined according to the test described above for compounds of formula I are given below (Table 1).

TABLE 1

| Example | $IC_{50}$ [µM] (results of one or two experiments) |
|---|---|
| 1 | 0.0046/0.0024 |
| 2 | 0.0028/0.0021 |
| 3 | 0.0017/0.0014 |
| 4 | 0.0019/0.0015 |
| 5 | 0.0013/0.0006 |
| 6 | 0.0018/0.0019 |
| 7 | 0.0029/0.0032 |
| 8 | 0.0028/0.0045 |
| 9 | 0.0017/0.0022 |
| 10 | 0.0029/0.004 |
| 11 | 0.0039 |
| 12 | 0.0038 |
| 13 | 0.0013 |
| 14 | 0.0017 |
| 15 | 0.0071 |
| 16 | 0.0059 |
| 17 | 0.0093 |
| 18 | 0.0015 |
| 21 | 0.0015 |
| 22 | 0.0017 |
| 23 | 0.0021 |
| 24 | 0.0021 |
| 25 | 0.0008 |
| 26 | 0.001 |
| 27 | 0.0003 |
| 28 | 0.0008 |
| 29 | 0.004 |
| 30 | 0.0059 |
| 31 | 0.0022 |
| 32 | 0.0037 |
| 33 | 0.0026 |
| 34 | 0.0013 |
| 35 | 0.0023 |
| 36 | 0.0023 |
| 37 | 0.0013 |
| 38 | 0.0017 |
| 39 | 0.0019 |
| 40 | 0.0022 |
| 41 | 0.0012 |
| 42 | 0.0019 |
| 43 | 0.0018 |
| 44 | 0.001 |
| 45 | 0.0013 |
| 46 | 0.0019 |
| 47 | 0.0008 |
| 48 | 0.0007 |
| 50 | 0.0023 |
| 51 | 0.0043 |
| 52 | 0.005 |

Example 54

As part of our assay development for the anti-DR5 screen, we cloned, expressed and purified Trail ligand and tested it on Jurkat cells to determine if we could kill cells with the ligand. The assay comprised Alamar Blue, a redox dye that fluoresces when living cells reduce the dye. When cells are killed by apoptosis, the resulting environment is oxidizing and the dye is not reduced and no fluorescence can be detected. As illustrated in FIG. 1, TRAIL induced apoptosis in Jurkat cells.

A screen for antibody agonists was performed. Mice were immunized with the DR5 receptor and B cells were fused to myelomas. The resulting hybridomas were arrayed into 384 well plates and following several days of growth, 20 µl of supernatant and cross-linking antibody was added to wells containing Jurkat cells. Twenty-four hours later alamar blue dye was added and 24 hours later the plate was read using an Acquest. Several positive wells containing positively reacting antibodies were identified.

Figure 2:
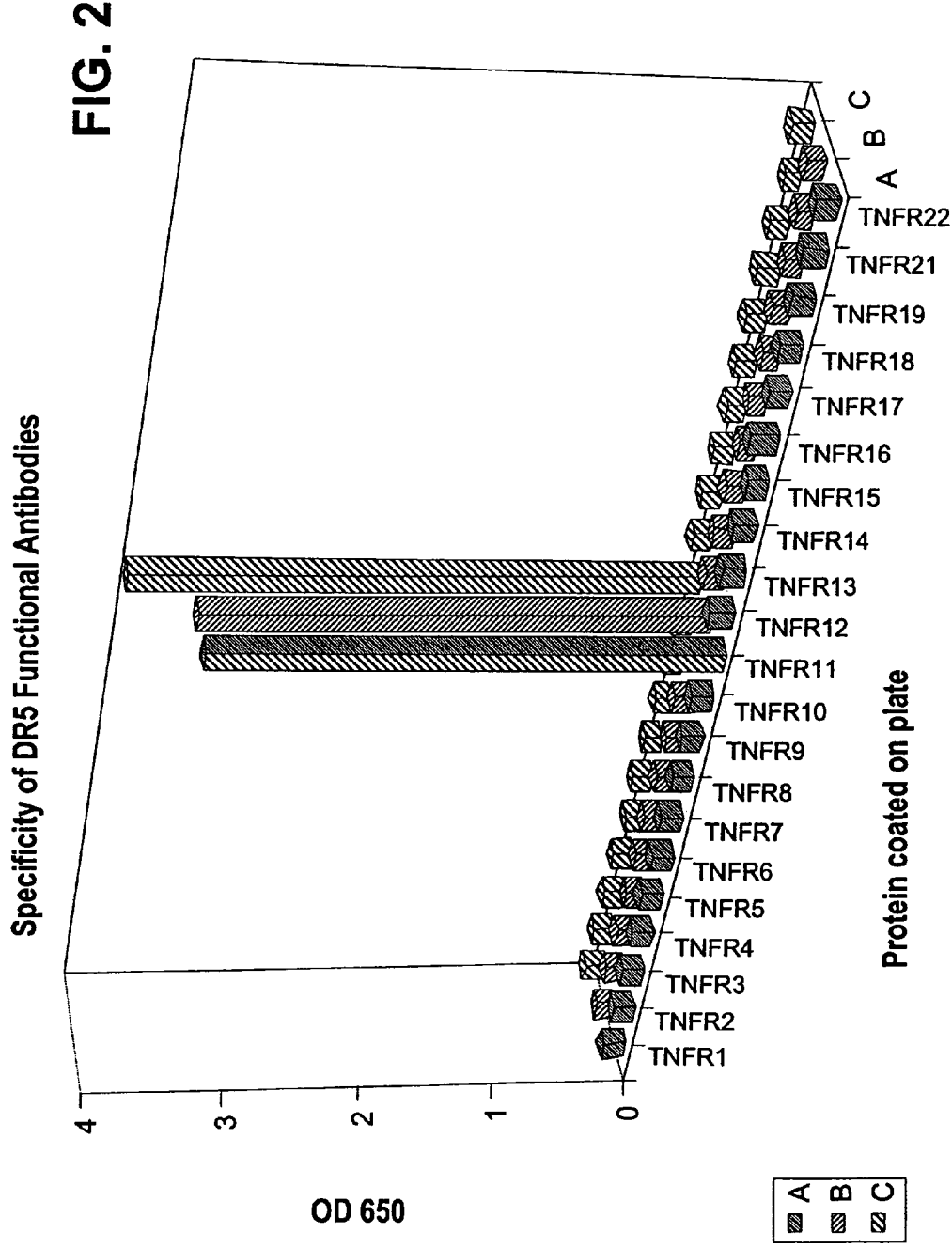
FIG. 2 displays specificity of DR5 functional antibodies.

The specificity of the positive antibodies was tested. Three hybridomas that gave a positive signal in the assay were sub-cloned, expanded and purified. Twenty-one TNF receptors were cloned, expressed and purified. Receptors were coated on wells and the three antibodies were subjected to ELISA analysis. The results show that the antibodies were only reactive with DR5, and thus, were very specific. See, FIG. 2.

Figure 3:
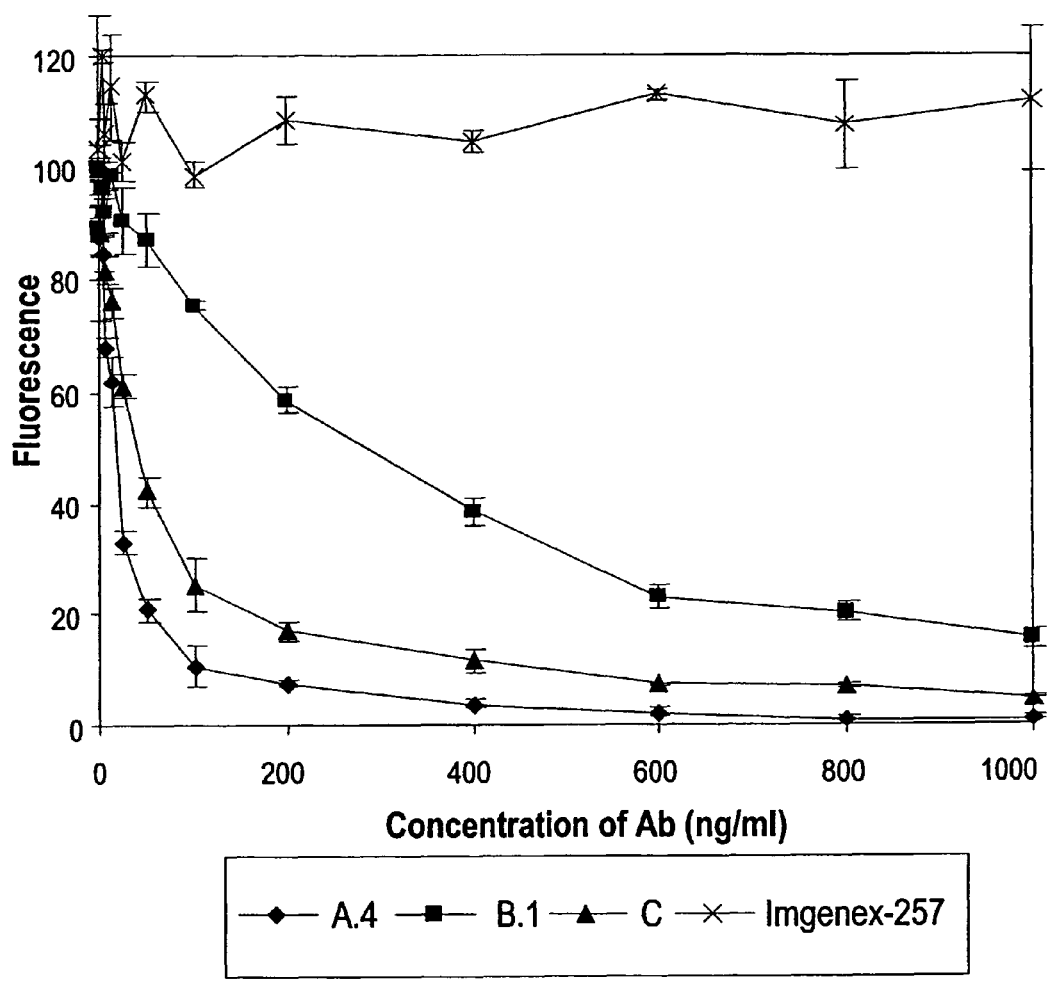
FIG. 3 displays the effect of three different DR5 antibody agonists on Jurkat cells.

FIG. 3 displays a dose response analysis. The 3 antibody agonists show different dose responses relative to Jurkat cell killing. Antibody A had the best potency and thus was chosen for further studies. Imgenex-257 is a DR5 specific antibody that has no functional activity.

Figure 4:
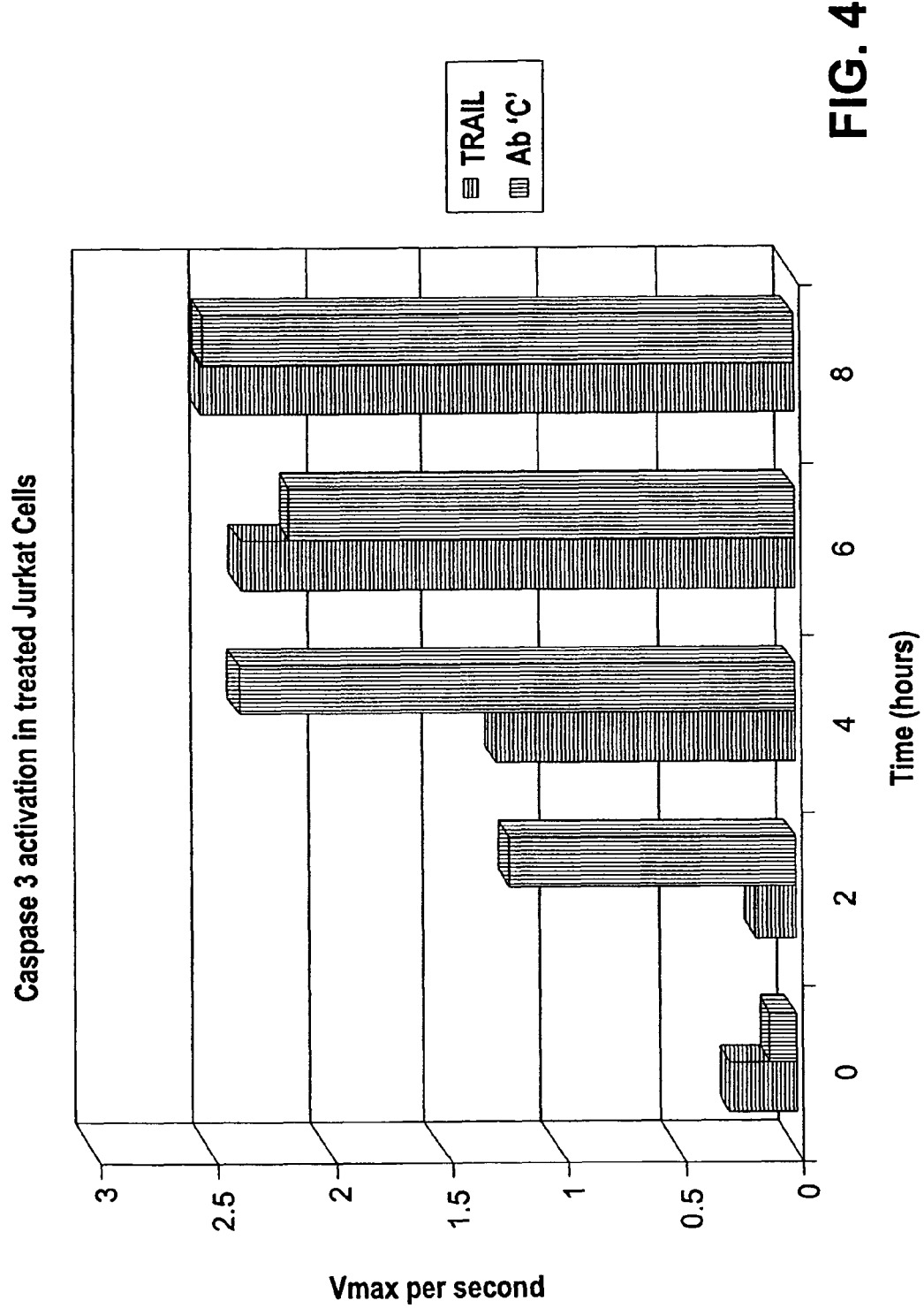
FIG. 4 illustrates Caspase-3 activity in treated Jurkat cells.

Caspase 3 activation was determined. To determine if the antibody was killing the cells by apoptosis and not by some indirect or non-specific mechanism, we ran Caspase-3 activity assays. Antibody or ligand was mixed with cells at various concentrations and cell extracts were generated from the treated cells. A fluorescent substrate was added to the lysate, which could be used to test for active caspase 3, an indicator of apoptosis. The antibody stimulated apoptosis in a similar fashion to the ligand. FIG. 4 displays the results.

The effects of DR5 antibody on colon and melanoma cell lines was determined. FIG. 5 shows dose response curves against various attached tumor cell lines. All of the cell lines are sensitive to the DR5 apoptosis inducing antibodies except the HCT 116 bax/bax-cell line, which is incapable of carrying out apoptosis.

FIG. 6 displays the same experiment carried out on various breast cancer cell lines. T47D and ZR-75-1 are both resistant to the tumoricidal activity of DR5, whereas, MCF-7 and MDA-MB-231 are sensitive.

Figure 7:
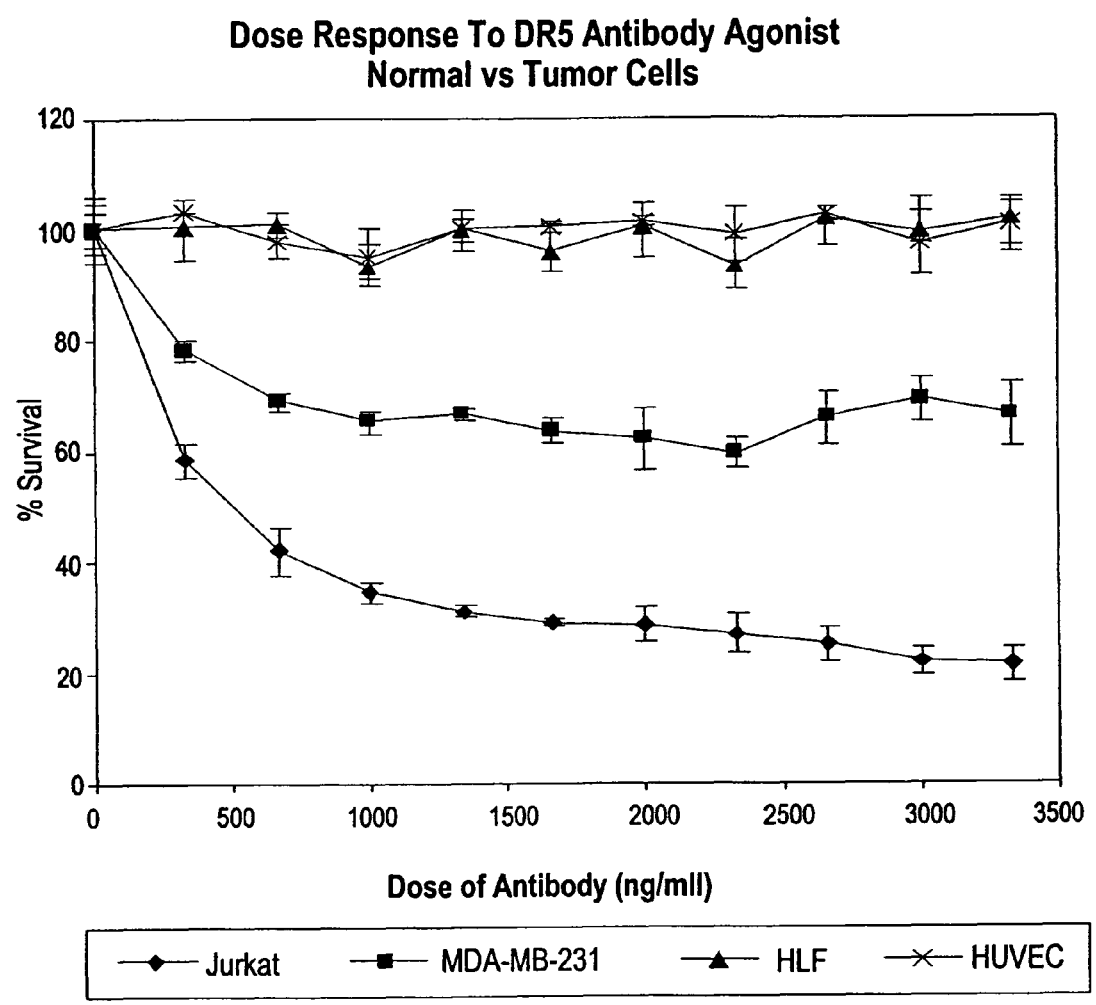
FIG. 7 illustrates the dose response to DR5 antibody agonists in normal and tumor cells.

FIG. 7 shows that tumor cells are sensitive to the action of the antibody but normal cells, human lung fibroblasts (HLF) and human umbilical vein epithelial cells (HUVEC) were resistant as indicated by their lack of a dose response.

Figure 8:
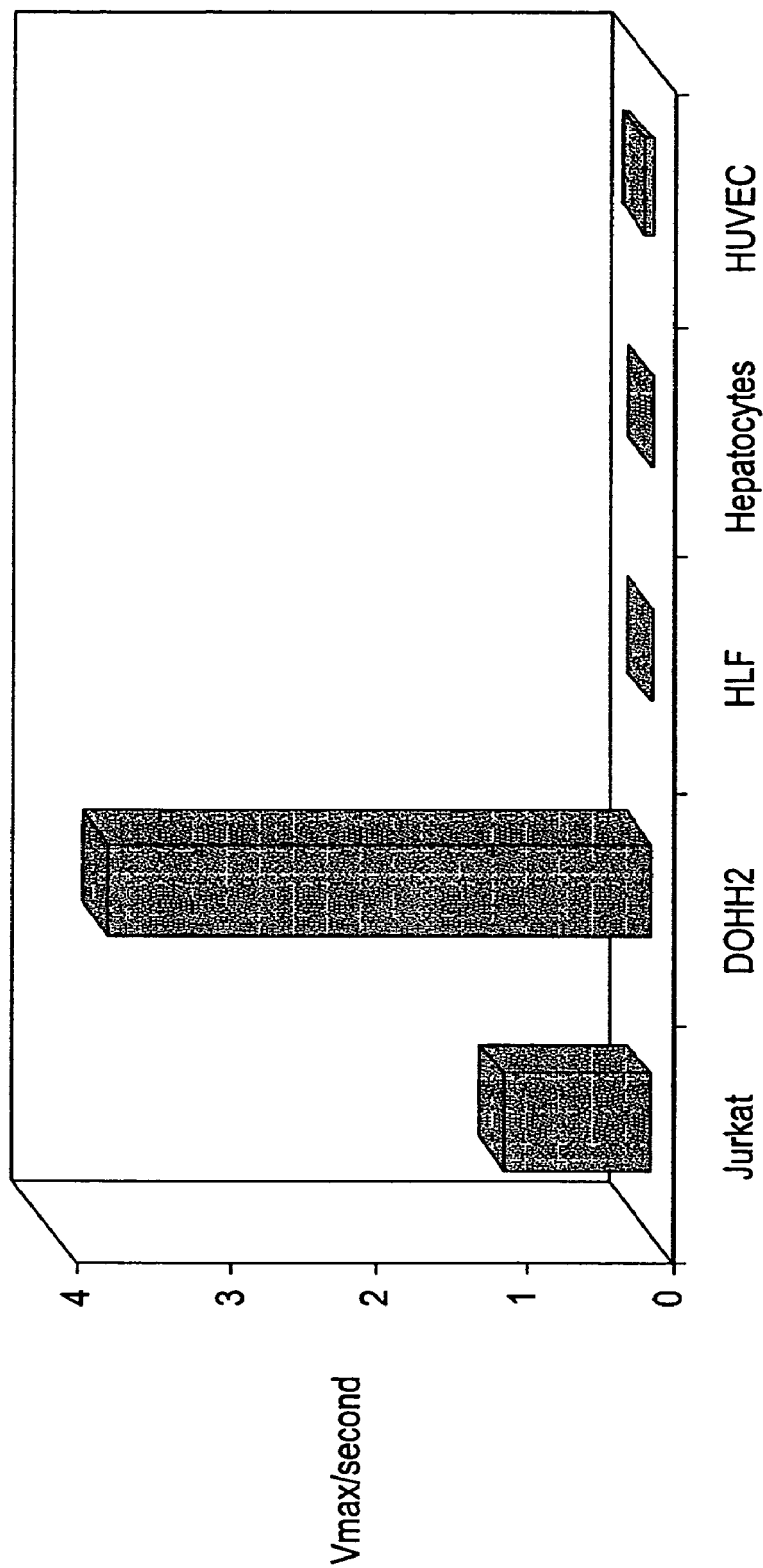
FIG. 8 illustrates DR5 antibody agonist "A" with respect to Caspase-3 activation.

To further demonstrate the point that normal cells are not killed by the antibody, human lung fibroblasts, human mammary epithelial cells and normal primary human hepatocytes were assayed for caspase 3 activity following treatment with the DR5 antibody. None of the normal cells showed activity whereas, DOHH2 follicular lymphoma and Jurkat cells showed Caspase activation associated with apoptosis. See, FIG. 8.

In addition, CaOV3, an ovarian cancer cell line, is wiped out by the antibody, whereas, the normal HLF's and HMEC's are completely unaffected by the DR5 antibody.

In vivo efficacy of the antibodies was tested. Ten mice were injected with $5 \times 10^6$ colo 205 (colon tumor cells) subcutaneously at day 0. Treatment with the DR5 antibody (400 µg) was started on day 11. After 2 injections with 400 µg of DR5 the 5 treated animals showed no evidence of tumor whereas the 5 mice given PBS all had large tumors. Thus the antibody appears to be effective in vivo.

Figure 9:
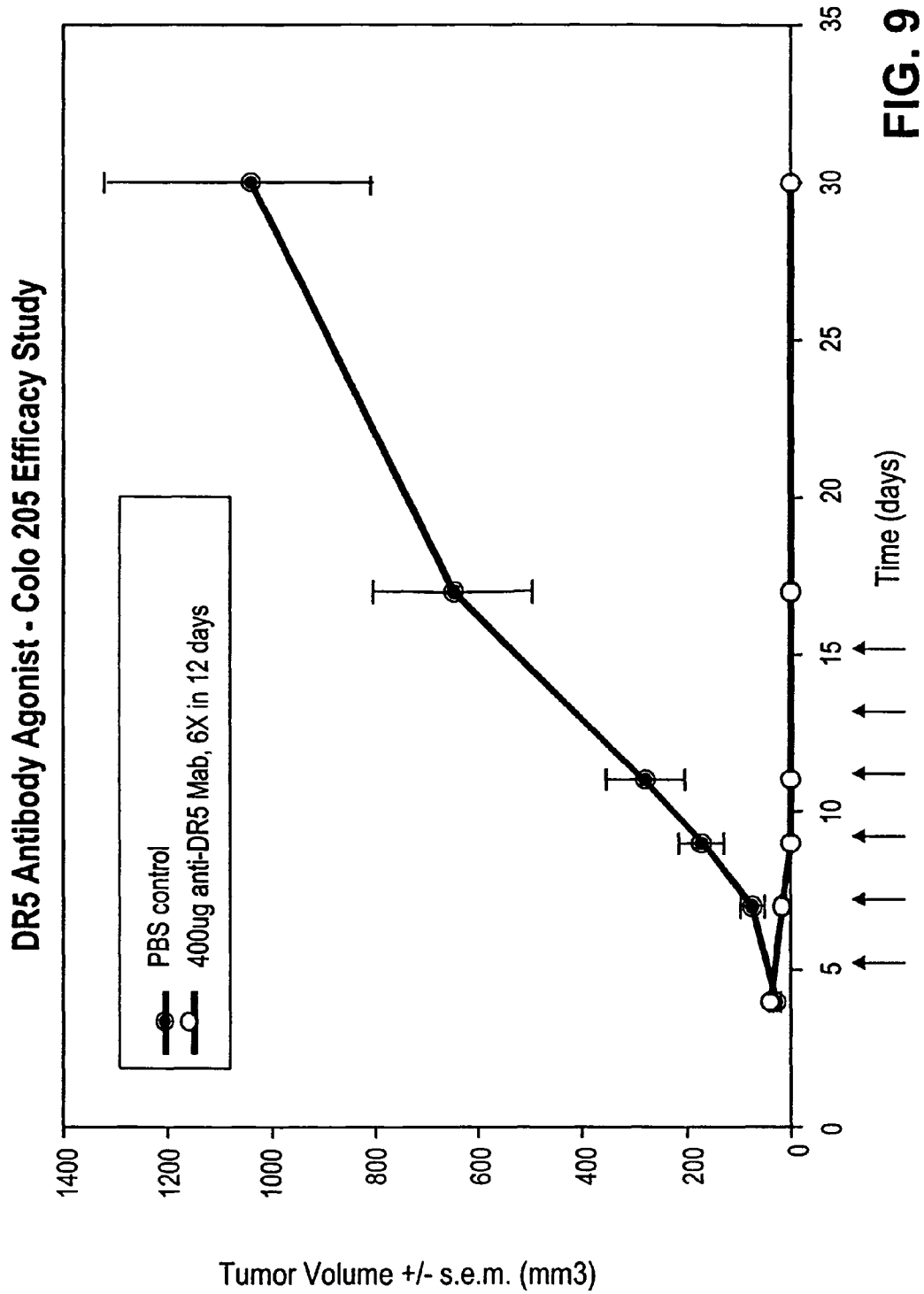
FIG. 9 illustrates DR5 antibody agonist effects on Colo 205 tumor volume.

The study was continued through Day 32. The untreated mice had large tumors or died. The treated mice showed no disease. The experiment was terminated at day 50. All of the untreated were dead. None of the treated showed any relapse at day 50. FIG. 9 displays the Colo 205 efficacy study shown graphically. The arrows refer to the treatment days.

Figure 10:
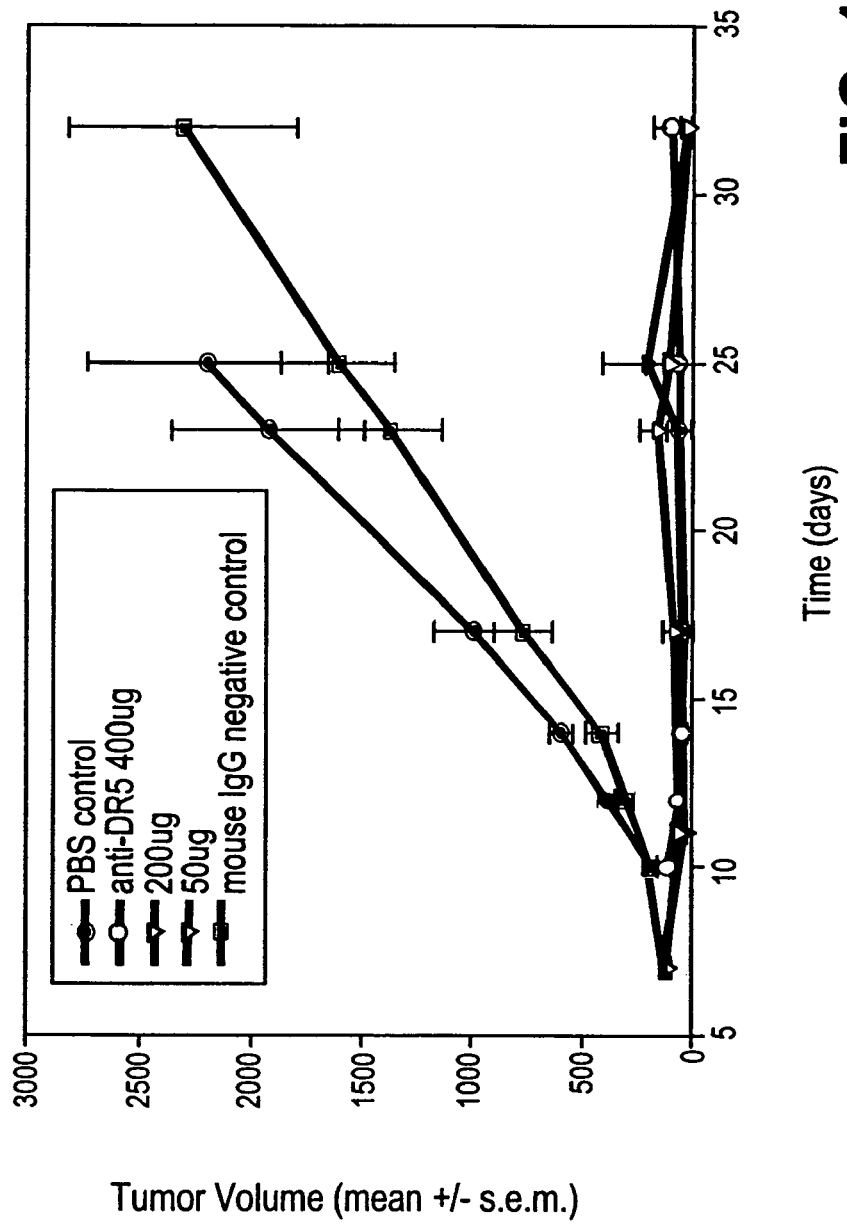
FIG. 10 illustrates anti-DR5 dose response in a COLO205 subcutaneous model.

The previous experiment represents a single dose study. To determine the potency of the antibody, we carried out a large dose response study. The group size was expanded to 8 mice per group and 50, 200, and 400 µg doses were given as described in the previous single dose study. The results indicate that the antibody is effective at low (e.g., 50 µg) doses. See, FIG. 10.

Figure 11:
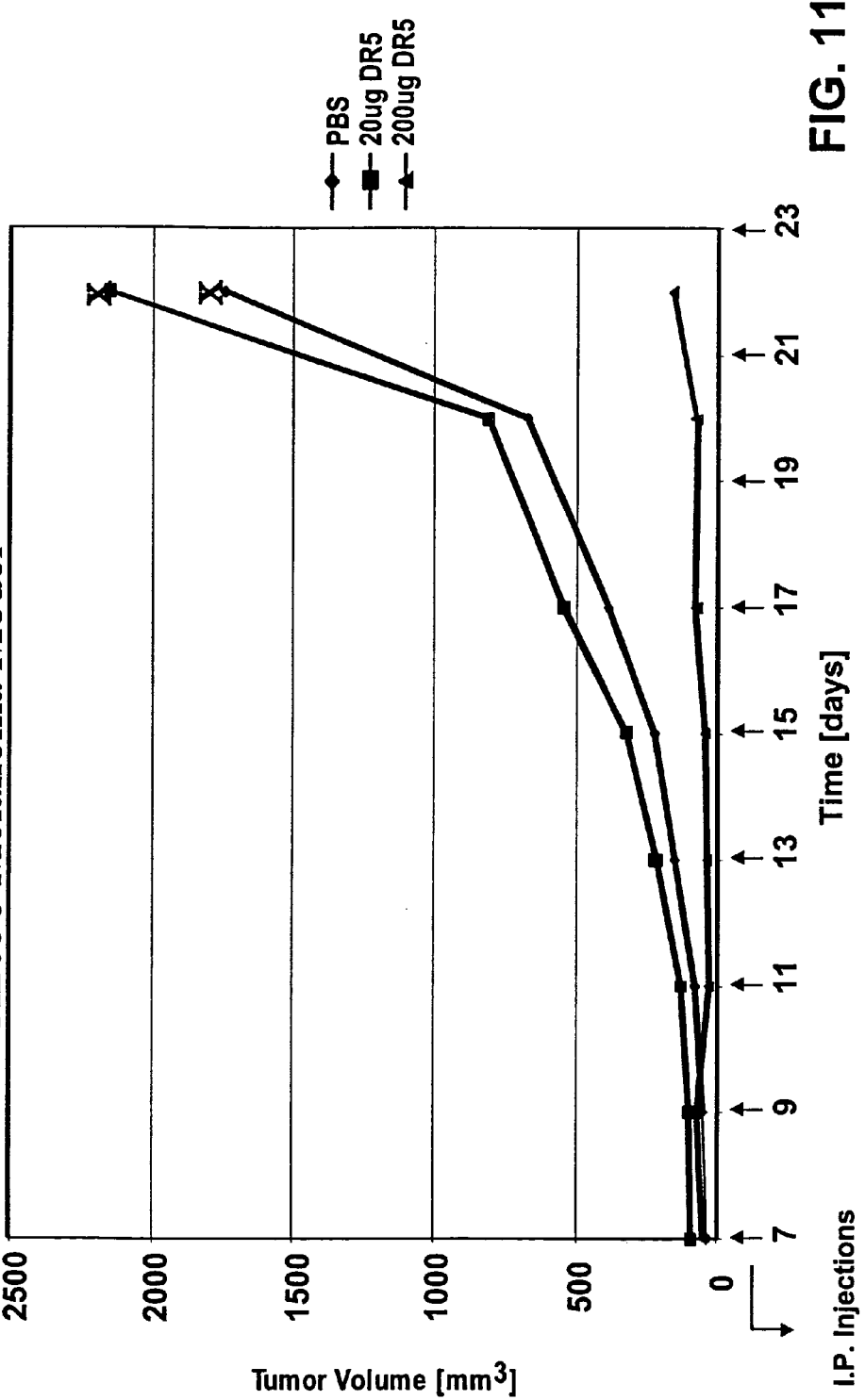
FIG. 11 illustrates the tumorcidal activity of DR5 monoclonal antibodies in vivo.

A smaller dose response study on a new tumor model, the melanoma cell line A2058, was also performed. This cell line was more resistant to the antibody in vitro. The group size was 2 mice. The treated mice (400 µg) shows in vivo tumoricidal activity, whereas the mice treated with 20 µg or PBS established large tumors. See, FIG. 11.

Since different cell lines show various degrees of sensitivity to the DR5 antibody, we explored the development of small molecule synergists that sensitize resistant or pertly resistant cell lines to the action of the antibody. We approached this problem by analyzing apoptotic pathways, determining where apoptosis could potentially be blocked, and what types of small molecule synergists could be pro-apoptotic in nature.

Figure 12:
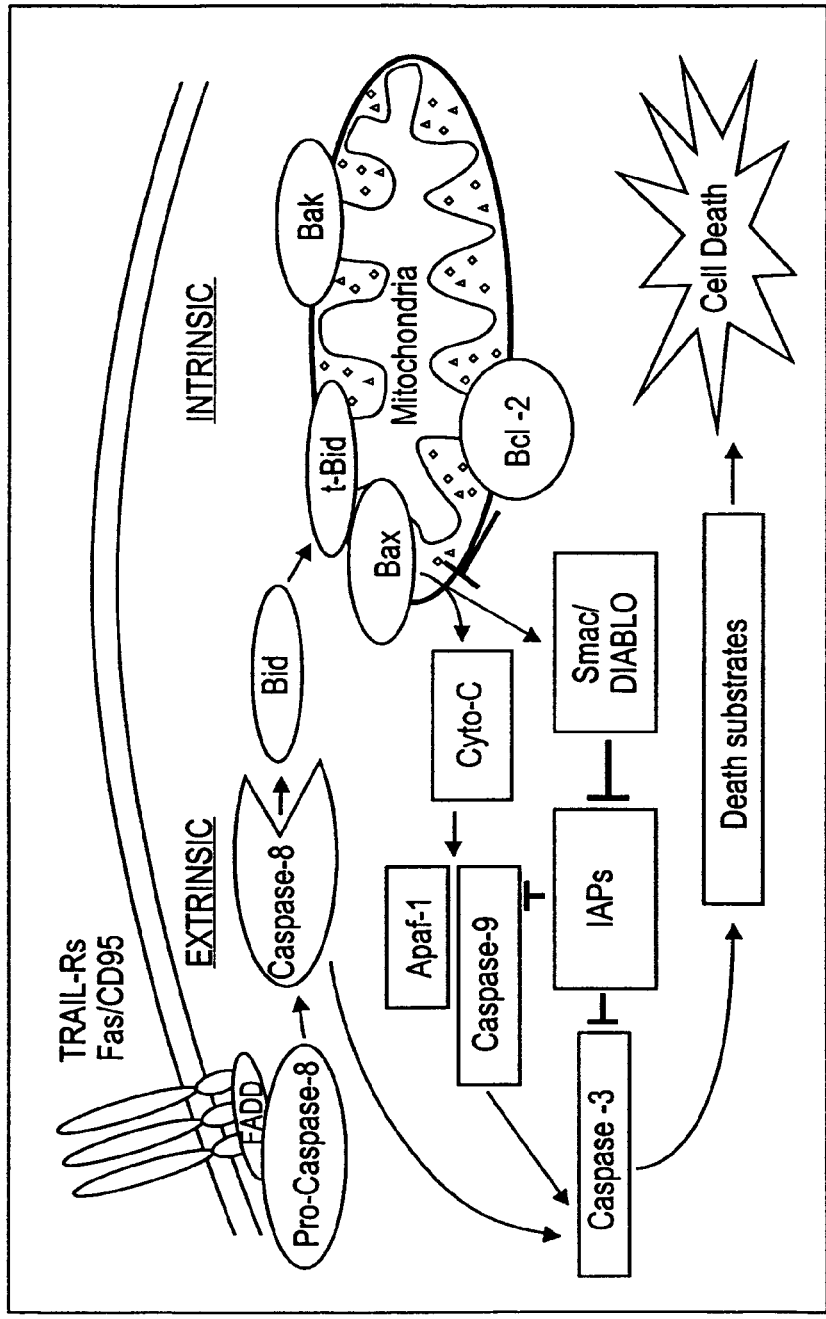
FIG. 12 illustrates pathways for Caspase activation and apoptosis.

FIG. 12 depicts the extrinsic and intrinsic pathways for apoptosis. The key points are that tumor cells over-express inhibitors of apoptosis (IAPs) and Bcl2 that blocks the release of key pro-apoptotic proteins (cyto C and SMAC) from the mitochondria. The blocks established by these proteins can be overcome by the addition of SMAC. SMAC inhibits the IAPs. A SMAC mimetic called LB 672 was tested for its possible synergstic effect to sensitize tumor cells to the action of the DR5 agonist.

Figure 13:
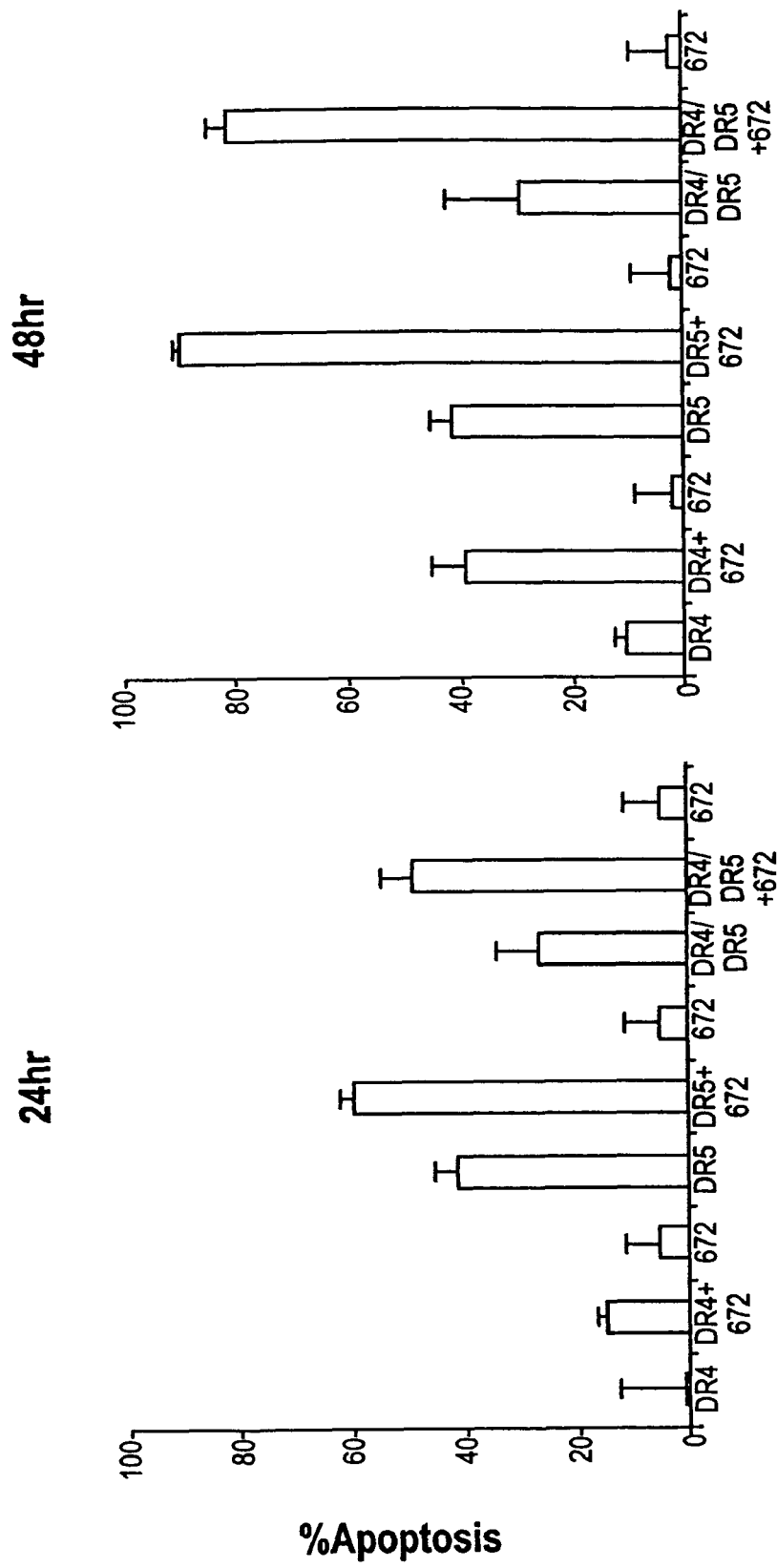
FIG. 13 illustrates anti-DR4 or anti-DR5-induced apoptosis in A2058 cells in the presence of a SMAC mimetic.

FIG. 13 shows the effect of the SMAC mimetic on A2058 melanoma cells. Previously, we showed that these cells are partially sensitive to the antibody. This graph shows that cell treated with SMAC and DR5 antibody are completely ablated while the 672 compound has virtually no activity on its own.

Figure 14:
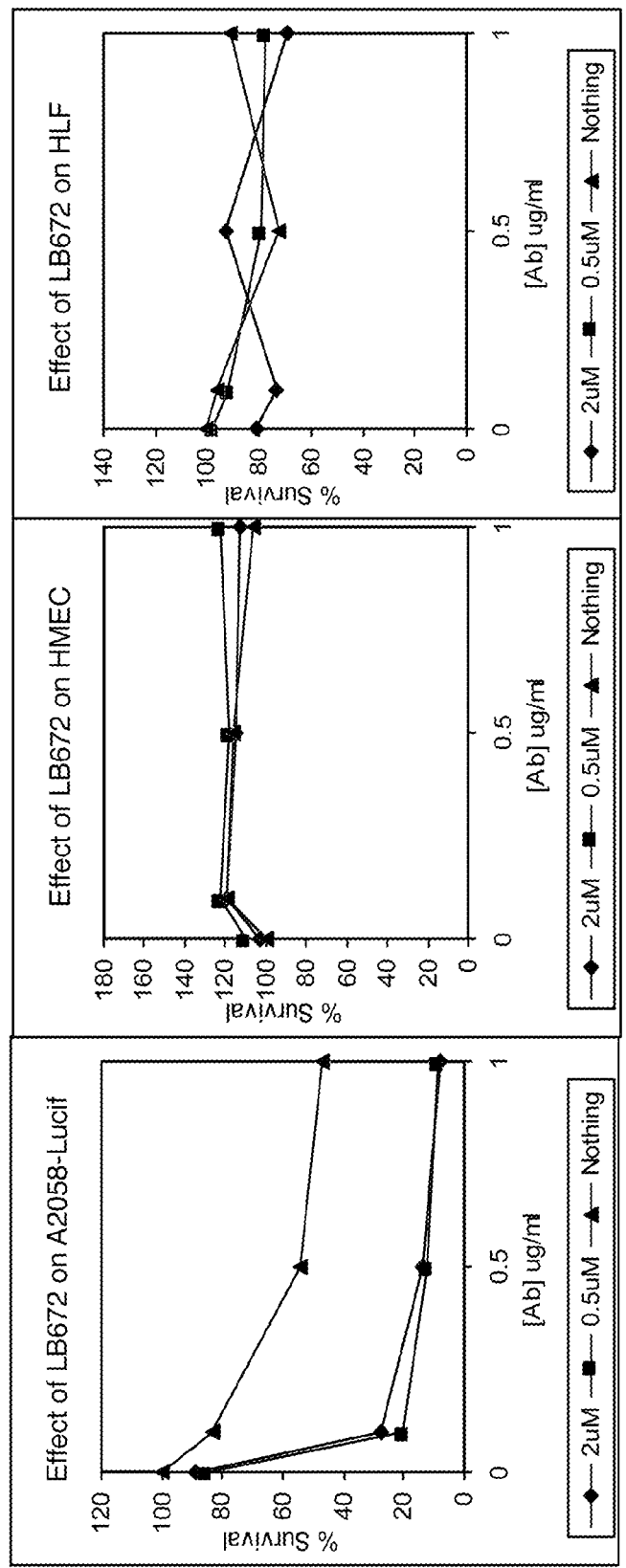
FIG. 14 illustrates the effect of the SMAC mimetic on normal and tumor cells.

FIG. 14 displays dose response graphs showing the effects of different concentrations of SMAC on A2058 melanoma cells. Again, these tumor cells are partially resistant, but are sensitized to low levels of SMAC (50-100 nM). However, more importantly, neither HMEC or HLF cells are sensitized by the SMAC mimetic LB672.

Figure 15:
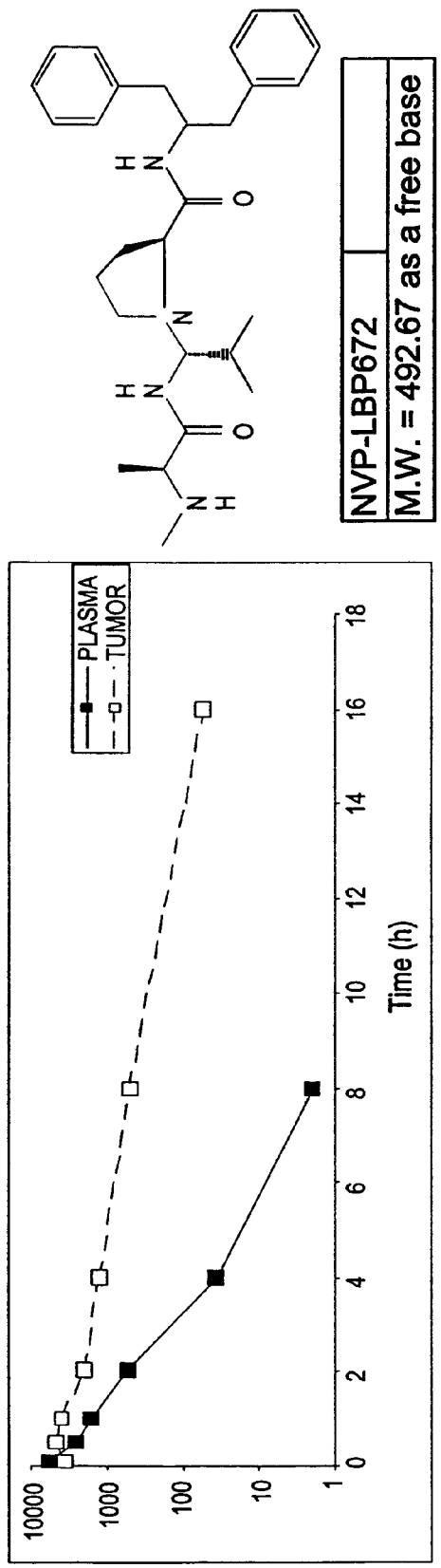
FIG. 15 illustrates a Pk and PD study of the SMAC mimetic.

FIG. 15 shows the pharmakokinetic properties of SMAC.

Figure 16:
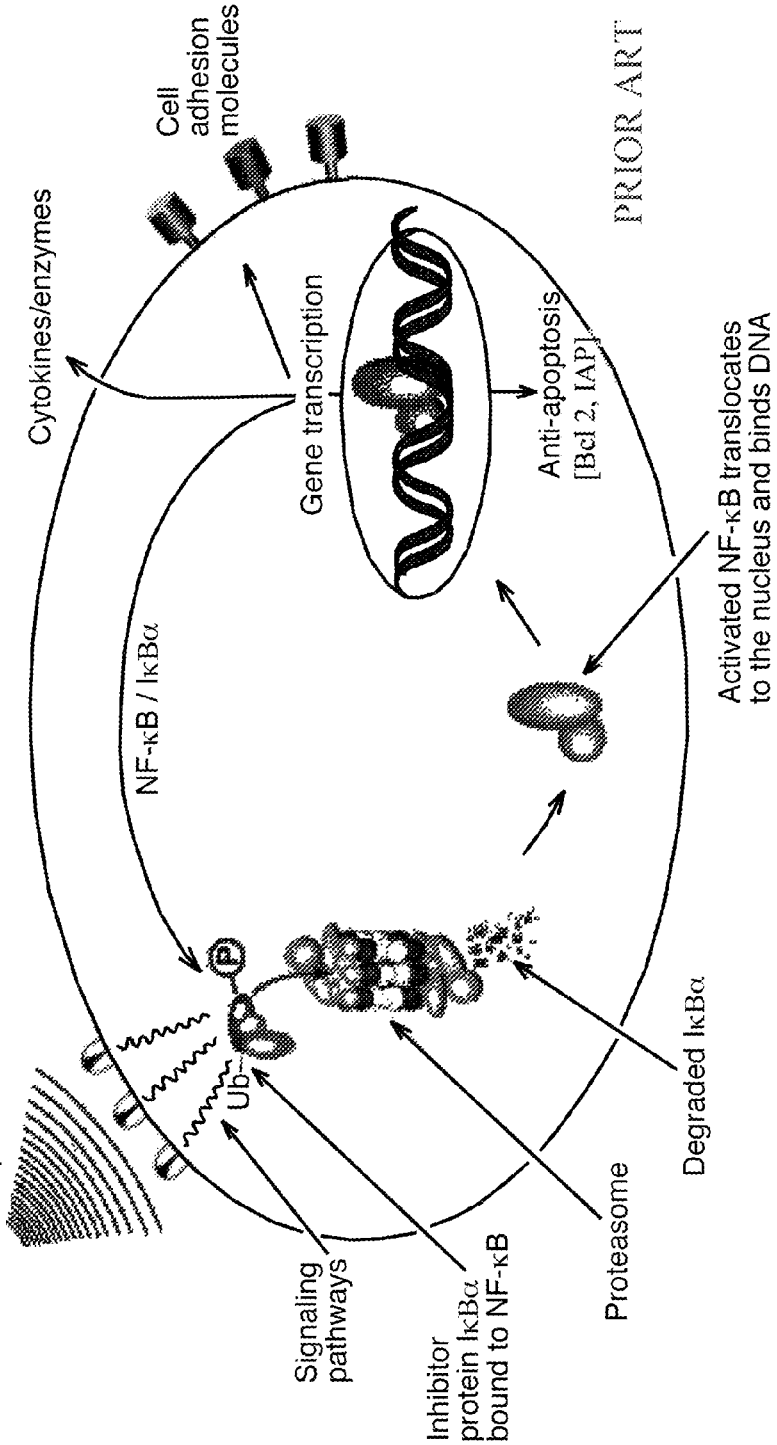
FIG. 16 illustrates the NFκB pathway and its relation to the proteasome.

A second synergist strategy was employed to test the use of proteasome inhibitors as DR4/DR5 synergists. As shown in FIG. 16, proteasome inhibitors prevent the proteasome from degrading IκB. This in turn prevents the release of NFκB. NFκB is known to translocate to the nucleus and initiate transcription of BCL2, IAPS, and other anti-apoptotic factors.

Figure 17:
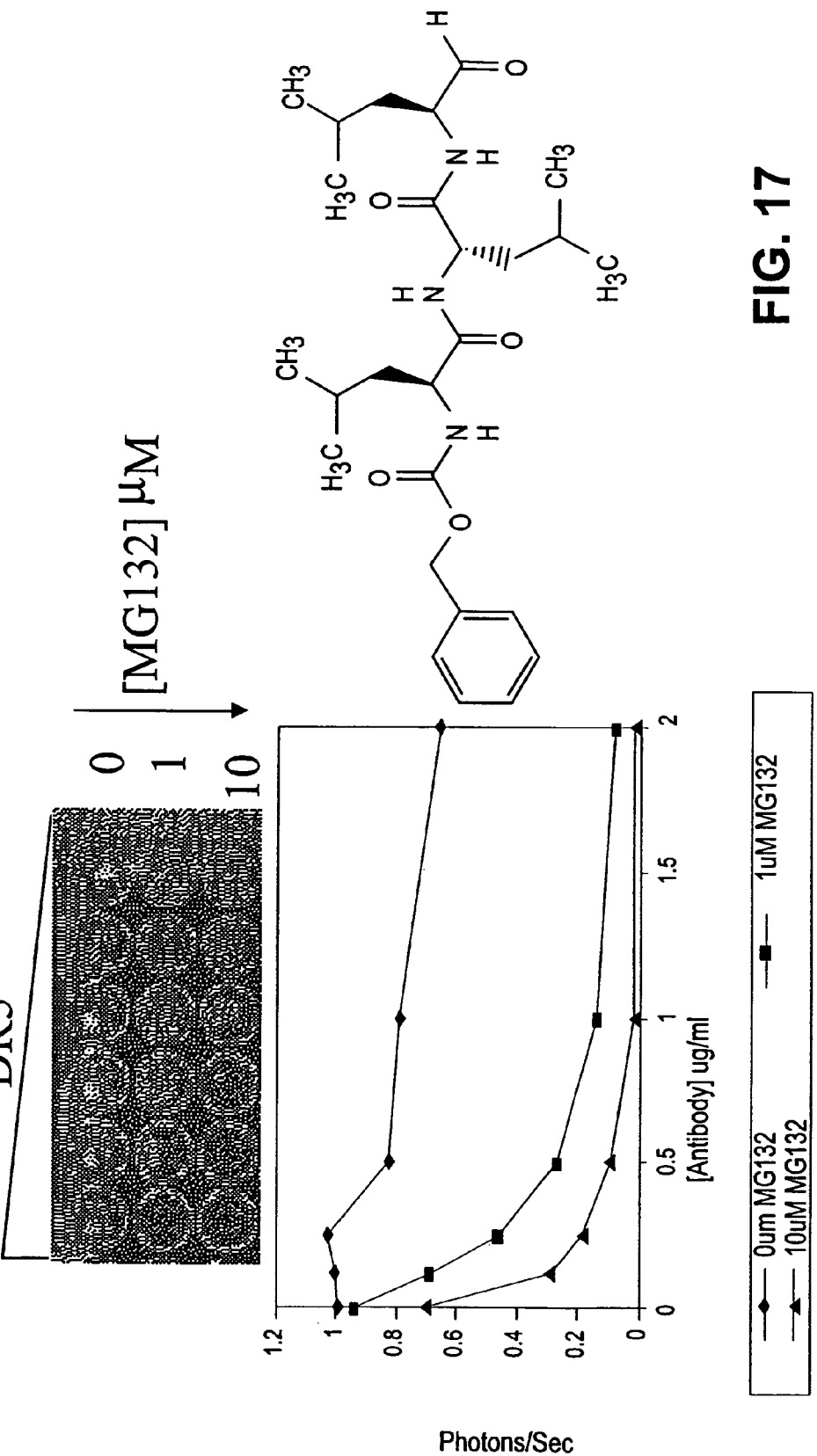
FIG. 17 illustrates that the proteasome inhibitor MG132 enhances DR5 antibody-induced apoptosis.

We first tested whether proteasome inhibitors would sensitize tumor cells to DR5 by the addition of MG 132, a commercially available weak proteasome inhibitor. FIG. 17 shows that at reasonably high concentrations, MG 132 sensitized resistant SW 480 colon cells to the action of the antibody.

Figure 18:
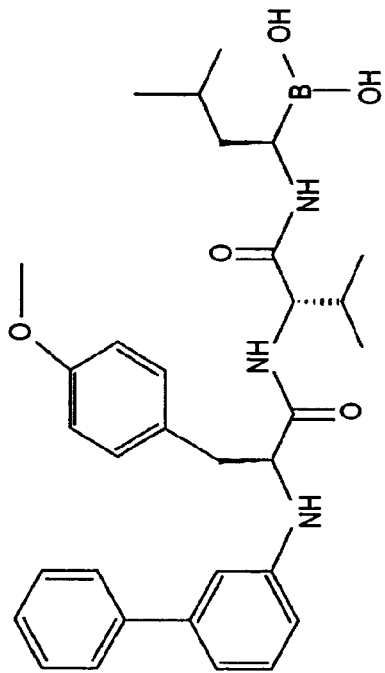
FIG. 18 illustrates various proteasome inhibitors.

We also obtained several potent proteasome inhibitors. The compounds that showed the best effects were the boronates. The maximal tolerated doses demonstrate that these compounds are relatively toxic, and thus there is a narrow window between toxicity and tumoricidal efficacy in vivo. See, FIG. 18.

The proteasome inhibitors sensitized A2058-LUC to the DR5 antibodies. See, FIG. 19. The proteasome inhibitors sensitized the resistant hepatoma cell line HUH-7 to the antibodies as well. See, FIG. 20. However, neither compound had an effect on normal HMEC cells. Furthermore, these cells were not sensitized to the action of the antibody. See, FIG. 21.

Variable regions from the DR5 mouse antibody A were cloned out and inserted into an SP20 Expression system. These vectors encode Human IgG 1 Fc. The resulting human chimera is 80% human and 20% mouse. The nucleic acid sequences of the heavy and light chain variable regions are displayed in FIG. 22. The amino acid sequence of the heavy chain variable region is displayed in FIG. 24 or FIG. 35 and the amino acid sequence of the light chain variable region is displayed in FIG. 25 or FIG. 35. The chimera was expressed in SP2/0 cells at 20 pg/cell/day. The resulting human chimeric antibody was cross-linked with a goat anti-human Fc and tested for functional activity. The chimeric had functional tumoricidal activity equivalent to the mouse antibody. See, FIG. 21.

Example 55

Figure 26:
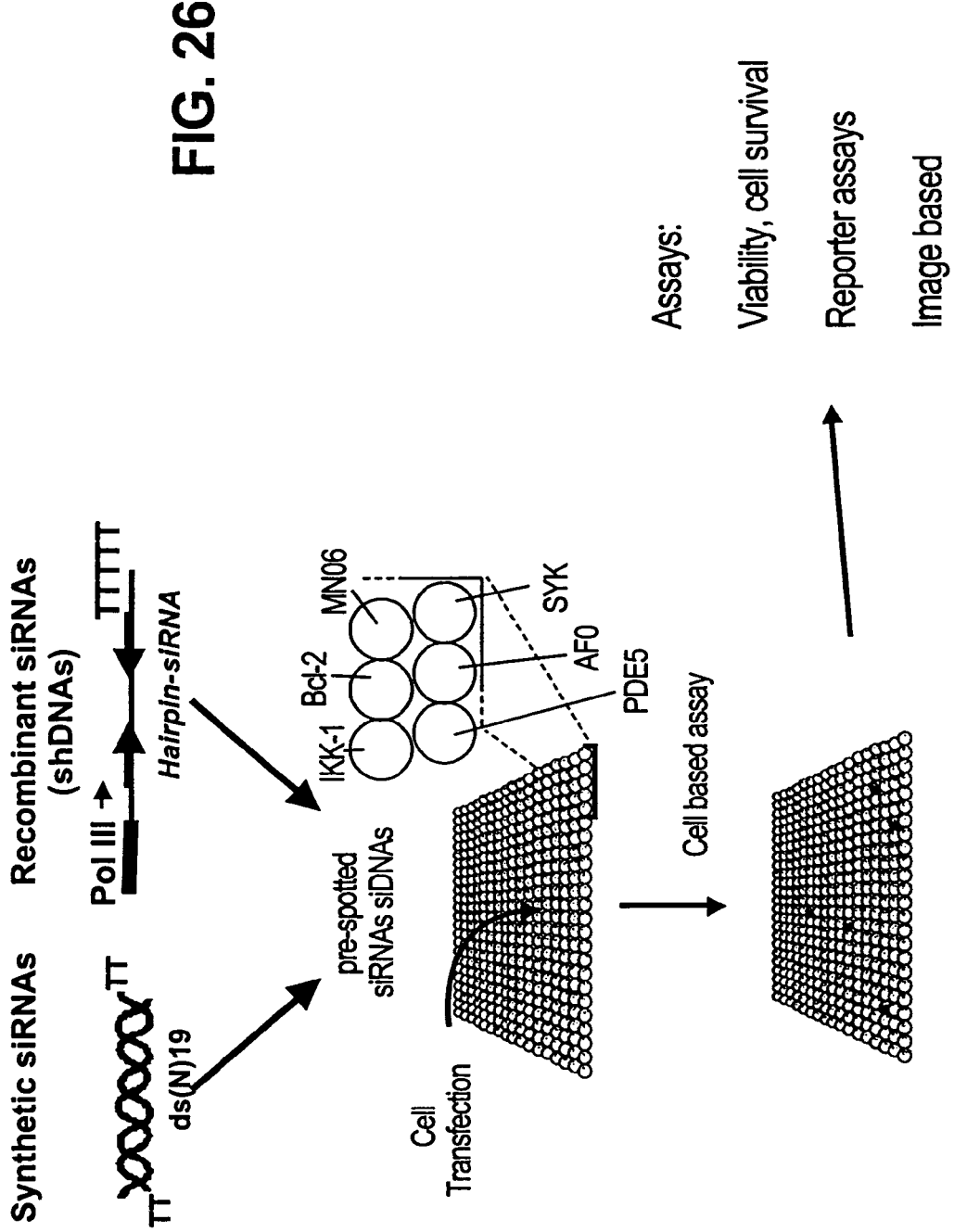
FIG. 26 illustrates a screening methodology for identifying gene products that mediate TRAIL-induced apoptosis by introducing siRNAs to knockout specific gene expression in a cell-based assay. TTds(N)19TT=SEQ ID NO:6.

A library of siRNA molecules was transfected into cells, the cells were contacted with TRAIL and the cells were screened for altered viability compared to the absence of TRAIL. Cells with altered viability were then used to identify the particular siRNA transfected into the cell, thereby determining the gene inhibited by the siRNA. See, FIGS. 26 and 27.

Figure 28:
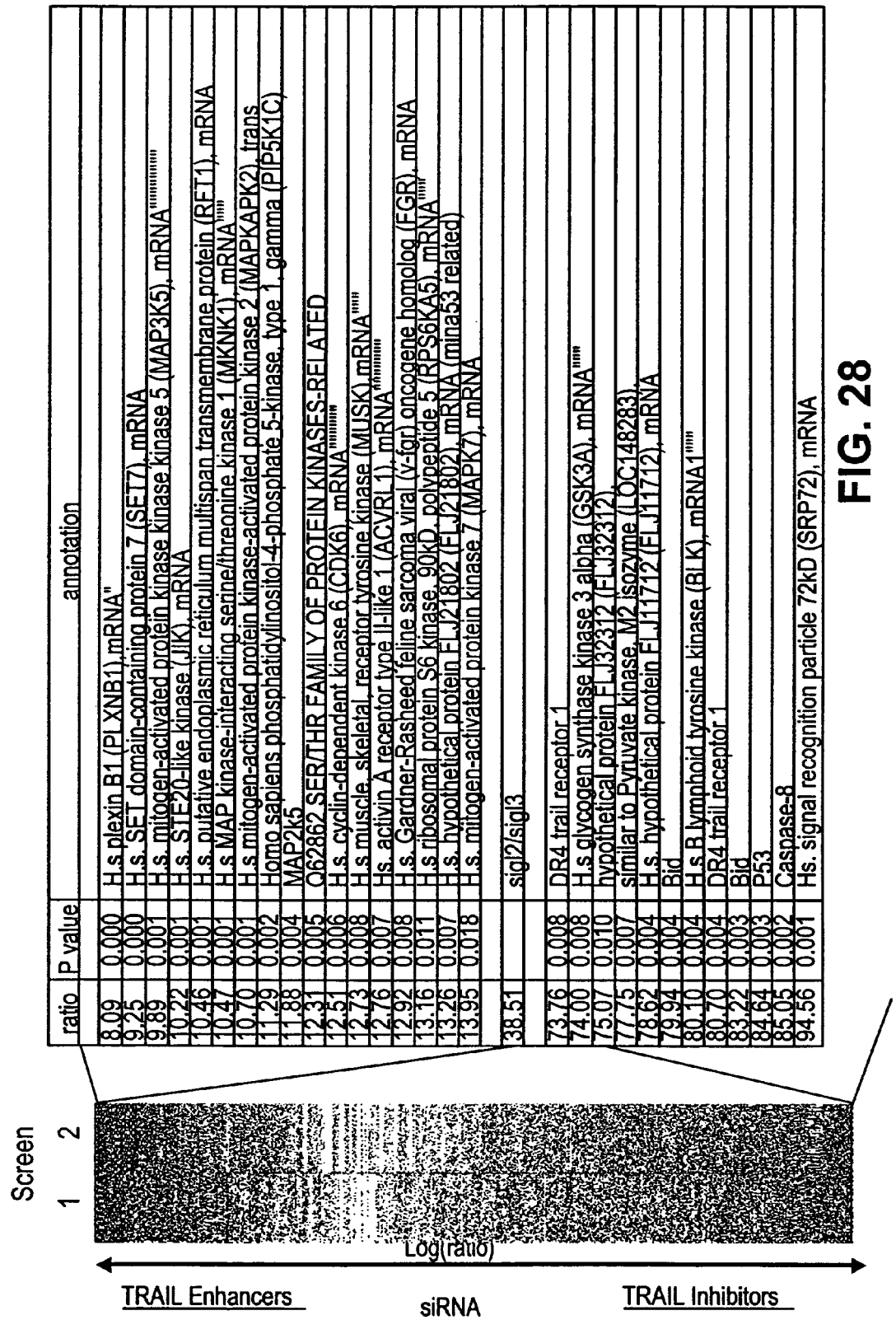
FIG. 28 provides a list of hits identified in the above-described siRNA screen. "Ratio" refers to the ratio of viable cells (i.e., non-apoptotic) following addition of TRAIL compared to the absence of TRAIL. Low ratios (lower than 50) indicate that the gene products interfere with apoptosis. Higher ratios (greater than 50) indicate gene products that contribute to apoptosis.

FIG. 28 illustrates gene products corresponding to siRNAs that were selected based on the screen. Gene products whose inhibition with siRNAs leads to a low TRAIL (+/−) ratio are inhibitors of TRAIL-induced apoptosis.

Table 1 provides additional information, including Genbank accession products identified in FIG. 28.

TABLE 1

| annotation | acc# | symbol | untreated | trail | ratio | P score |
|---|---|---|---|---|---|---|
| Activators of TRAIL-induced apoptosis | | | | | | |
| H.s plexin B1 (PLXNB1), mRNA" | NM_002673 | PLXNB1 | 73.85 | 5.96 | 0.081 | 6.27E−05 |
| H.s. SET domain-containing protein 7 (SET7), mRNA | NM_030648 | SET7 | 79.06 | 7.30 | 0.092 | 0.000266 |
| H.s. mitogen-activated protein kinase kinase kinase 5 (MAP3K5) | NM_005923 | MAP3K5 | 86.84 | 8.58 | 0.099 | 0.000585 |
| H.s. STE20-like kinase (JIK), mRNA | NM_016281 | JIK | 86.41 | 8.67 | 0.102 | 0.000727 |
| H.s MAP kinase-interacting serine/threonine kinase 1 (MKNK1) | NM_003684 | MKNK1 | 76.61 | 8.13 | 0.105 | 0.000755 |
| H.s. putative endoplasmic reticulum multispan transmembrane protein (RFT1) | NM_052859 | RFT1 | 77.39 | 7.99 | 0.105 | 0.000892 |
| *Homo sapiens* phosphatidylinositol-4-phosphate 5-kinase, type I, gamma (PIP5K1C) | XM_047620 | PIP5K1C | 83.06 | 8.88 | 0.107 | 0.001498 |
| H.s mitogen-activated protein kinase-activated protein kinase 2 (MAPKAPK2), transcript variant 1 | NM_004759 | MAPKAPK2 | 77.71 | 8.44 | 0.113 | 0.002227 |
| H.s. mitogen-activated protein kinase kinase 5 (MAP2K5) | NM_002757 | MAP2K5 | 94.66 | 11.24 | 0.119 | 0.00381 |
| H.s. cyclin-dependent kinase 6 (CDK6), mRNA | NM_001259 | CDK6 | 84.10 | 10.52 | 0.125 | 0.006206 |
| H.s. activin A receptor type II-like 1 (ACVRL1), mRNA | NM_000020 | ACVRL1 | 84.64 | 10.40 | 0.128 | 0.006776 |

TABLE 1-continued

| annotation | acc# | symbol | untreated | trail | ratio | P score |
|---|---|---|---|---|---|---|
| H.s. Gardner-Rasheed feline sarcoma viral (v-fgr) oncogene homolog (FGR), mRNA | NM_005248 | FGR | 106.43 | 13.45 | 0.129 | 0.007914 |
| H.s. hypothetical protein FLJ21802 (FLJ21802), mRNA | NM_024644 | FLJ21802 | 96.15 | 12.46 | 0.133 | 0.006866 |
| H.s muscle, skeletal, receptor tyrosine kinase (MUSK), mRNA"""" | NM_005592 | MUSK | 96.32 | 12.17 | 0.127 | 0.008166 |
| H.s. chromosome 20 open reading frame 88 (C20orf88), mRNA | NM_080820 | C20orf88 | 76.58 | 10.09 | 0.132 | 0.009842 |
| H.s budding uninhibited by benzimidazoles 1 (yeast homolog) (BUB1), mRNA"""" | NM_004336 | BUB1 | 75.76 | 9.65 | 0.133 | 0.009722 |
| H.s ribosomal protein S6 kinase, 90 kD, polypeptide 5 (RPS6KA5), mRNA"""" | NM_004755 | RPS6KA5 | 77.84 | 10.22 | 0.132 | 0.010693 |
| H.s v-yes-1 Yamaguchi sarcoma viral related oncogene homolog (LYN), mRNA"""" | NM_002350 | LYN | | | | |
| H.s. mitogen-activated protein kinase 7 (MAPK7), mRNA | NM_002749.1 | MAPK7 | | | | |
| H.s. v-akt murine thymoma viral oncogene homolog 1 (AKT1), mRNA"""" | NM_005163 | AKT | | | | |
| Hs. signal recognition particle 72 kD (SRP72), mRNA | NM_006947 | SRP72 | 77.23 | 71.11 | 0.946 | 0.00073 |
| Inhibitors of TRAIL-induced apoptosis | | | | | | |
| Caspase-8 | NM_001228 | CASP8 | 99.30 | 84.45 | 0.850 | 0.002444 |
| Bid | NM_001196 | Bid | 110.50 | 91.95 | 0.832 | 0.003027 |
| DR4 trail receptor 1 | NM_003844 | DR4 | 87.26 | 70.90 | 0.807 | 0.003725 |
| H.s B lymphoid tyrosine kinase (BLK), mRNA | NM_001715 | BLK | 98.04 | 77.87 | 0.801 | 0.004003 |
| similar to Pyruvate kinase, M2 isozyme (LOC148283), | XM_086132 | PKM2like | 83.15 | 60.32 | 0.778 | 0.006752 |
| H.s glycogen synthase kinase 3 alpha (GSK3A), mRNA | NM_019884 | GSK3A | 104.20 | 76.91 | 0.740 | 0.008469 |
| hypothetical protein FLJ32312 (FLJ32312), | NM_144709 | FLJ32312 | 88.32 | 65.01 | 0.751 | 0.010144 |
| H.s. mitogen-activated protein kinase 10 (MAPK10), mRNA | NM_002753 | MAPK10/JNK3 | | | | |
| TCF4: transcription factor 4, LocusID: 6926 | NM_003199 | TCF4 | | | | |
| H.s v-abl Abelson murine leukemia viral oncogene homolog 2 (arg, Abelson-related gene) (ABL2), transcript | NM_005158 | ABL2 | | | | |
| H.s v-ros avian UR2 sarcoma virus oncogene homolog 1 (ROS1), mRNA" | NM_002944 | ROS1 | | | | |
| v-myc avian myelocytomatosis viral oncogene homolog | NM_002467 | MYC | | | | |

Figure 29:
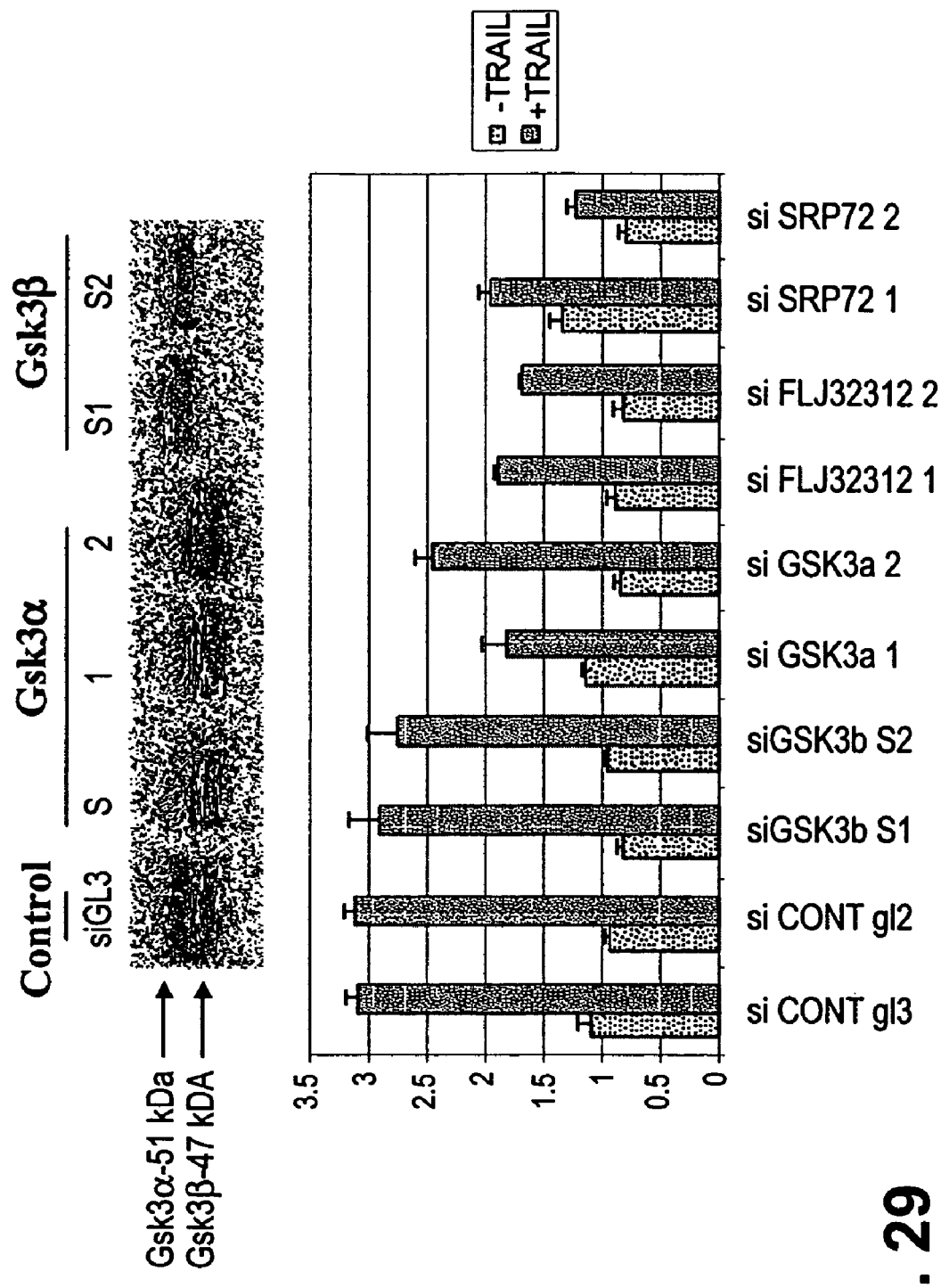
FIG. 29 illustrates siRNA data for Gsk3α and Gsk3β. The top of the figure illustrates that the siRNAs are specific for Gsk3α or Gsk3β. The bar chart the bottom of the figure illustrates Caspase activity following introduction of an siRNA in the presence or absence of TRAIL.

Example 56 siRNAs were identified that specifically inhibit expression of Gsk3α or GSK3β, thereby allowing us to determine the effect of either gene product on TRAIL-induced apoptosis. As illustrated in FIG. 29, inhibition of Gsk3α, but not Gsk3β, reduces Caspase activity in cells compared to controls. Thus, Gsk3α is an activator of TRAIL-induced apoptosis. Similarly, two other gene products SRP72 and FLJ32312, were also identified as activators of apoptosis.

Figure 30:
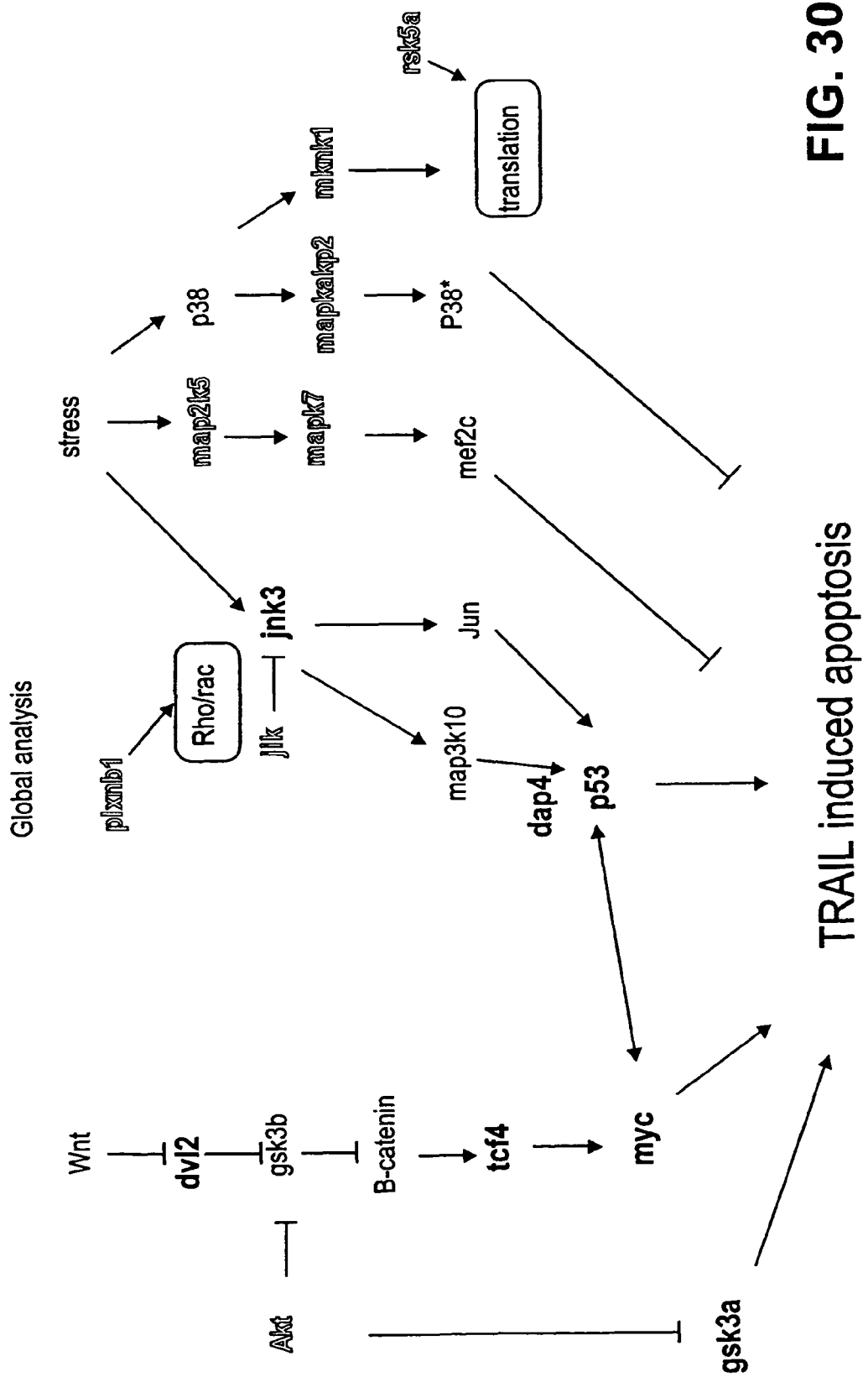
FIG. 30 illustrates a regulatory network for TRAIL-induced apoptosis. Of particular note, myc is pro-apoptotic. Therefore, inhibition of myc inhibits TRAIL-induced apoptosis and activation of myc synergistically activated TRAIL or anti-DR4 or anti-DR5-induced apoptosis.

The relationship of various components identified herein is provided in FIG. 30. The figure illustrates the relation and effect (e.g., apoptosis activator or inhibitor) of various components of the TRAIL-induced apoptosis pathway.

Example 57

A siRNA library targeting 510 genes arrayed in 384 well format was transfected into Hela cells. Cells were incubated for 48 hours to allow target decay, and treated with or without TRAIL. Viability was measured 20 hours after TRAIL treatment using alamar blue. A sensitivity ratio was determined for each siRNA for comparison with a total of 60 values obtained with control siRNAs. Hela cells treated with TRAIL ligand resulted in ~40% reduction in viability as measured by MTT assays in control wells. siRNAs that significantly inhibited or enhanced cells death were identified. See, Tables 2 and 3, respectively.

TABLE 2

Inhibitor siRNAs

| Acc. Number | Symbol | SR | p value |
|---|---|---|---|
| NM_006947 | SRP72 | 0.94 | 8.5E−22 |
| NM_001715 | BLK | 0.79 | 5.9E−16 |
| XM_086132 | PKM2-like | 0.75 | 3.6E−14 |
| NM_019884 | GSK3A | 0.73 | 3.6E−14 |
| NM_144709 | FLJ32312 | 0.72 | 1.8E−12 |
| NM_002467 | C-MYC | 0.69 | 5.3E−11 |
| NM_025133 | FLJ12673 | 0.65 | 2.9E−09 |
| NM_002944 | ROS1 | 0.61 | 2.5E−08 |
| NM_005158 | ABL2 | 0.61 | 2.9E−08 |
| NM_004705 | DAP4 | 0.61 | 3.2E−08 |
| NM_002753 | JNK3 | 0.60 | 7.8E−08 |
| NM_003199 | TCF4 | 0.59 | 2.0E−07 |
| NM_022575 | VPS16 | 0.59 | 2.1E−07 |
| NM_000858 | GUK1 | 0.59 | 3.3E−07 |
| NM_006257 | PRKCQ | 0.55 | 8.9E−06 |
| NM_006252 | PRKAA2 | 0.54 | 5.3E−05 |
| AK074085 | FLJ00156 | 0.53 | 8.6E−05 |
| NM_006254 | PRKCD | 0.53 | 1.0E−04 |
| NM_001569 | IRAK1 | 0.52 | 1.3E−04 |
| NM_004422 | DVL2 | 0.52 | 1.3E−04 |

TABLE 3

Enhancer siRNAs

| Acc. Number | Symbol | SR | p value |
|---|---|---|---|
| NM_012290 | TLK1 | 0.15 | 3.7E-21 |
| NM_016231 | NLK | 0.15 | 5.7E-22 |
| NM_015071 | GRAF | 0.14 | 1.4E-21 |
| NM_000162 | GCK | 0.14 | 2.5E-22 |
| NM_005163 | AKT1 | 0.14 | 1.1E-22 |
| NM_002749 | ERK5 | 0.14 | 6.8E-23 |
| NM_002350 | LYN | 0.14 | 3.0E-24 |
| NM_004755 | RPS6KA5 | 0.13 | 5.6E-24 |
| NM_004336 | BUB1 | 0.13 | 8.2E-27 |
| NM_005592 | MUSK | 0.12 | 3.2E-27 |
| NM_024644 | FLJ21802 | 0.12 | 9.5E-28 |
| NM_005248 | FGR | 0.12 | 2.2E-28 |
| NM_000020 | ACVRL1 | 0.12 | 3.4E-28 |
| NM_002757 | MEKK5 | 0.11 | 1.4E-28 |
| XM_047620 | PIP5K1C | 0.11 | 2.8E-33 |
| NM_004759 | MAPKAPK2 | 0.10 | 1.9E-18 |
| NM_052859 | RFT1 | 0.10 | 7.8E-35 |
| NM_003684 | MKNK1 | 0.10 | 9.3E-37 |
| NM_016281 | JIK | 0.09 | 4.4E-37 |
| NM_002673 | PLXNB1 | 0.08 | 2.7E-38 |

Several siRNAs identified in the screen that enhanced cell death as measured by viability assays were tested for their ability to enhance caspase activation by DR5 agonistic antibodies. DR5 antibody was titrated to produce a minimal amount of caspase activation as measured by fluorogenic peptides (DEVD-afc). The siRNAs directed against nsrna, nsurf, PAK1, stk12, Ask1 and JIK were transfected into Hela cells and then treated with DR5 antibodies. Control siRNA (nsrna) had little effect whereas the identified siRNAs significantly enhanced caspase activity.

Several additional (distinct from those in the screen) siRNAs directed towards PAK1 were designed and tested for their effect on viability in the presence or absence of DR5 antibody. The siRNA included:

```
siPAK1-0
AGAGCTGCTACAGCATCAA        (SEQ ID NO: 11)

siPAK1-1
GACAUCCAACAGCCAGAAA        (SEQ ID NO: 12)

siPAK1-2
GAGAAAGAGCGGCCAGAGA        (SEQ ID NO: 13)

hPAK1-6
UACCAGCACUAUGAUUGGA        (SEQ ID NO: 14)

siPAK1-7
UCUGUAUACACACGGUCUG.       (SEQ ID NO: 15)
```

PAK1-1 and PAK1-2 strongly reduced viability (MTT assay) in the colon carcinoma cell line HCT116 bax +/− at both 24 and 48 hours.

HCT116 bax −/− cells have both copies of bax deleted, rendering these cells very resistant to chemotherapeutic treatment, including to TRAIL1 and DR5 antibodies. However PAK1 siRNAs remained effective at reducing viability. These same results were also observed in colon carcinoma DLD1 cells.

To determine whether silencing or inhibition of PAK1 was toxic to normal cells, we tested PAK1 siRNAs on a primary ovarian epithelial cell line IOSE80. The results demonstrated that siRNAs directed against PAK1 do not reduce viability of normal cells. Thus, PAK1 and the other gene products.

In addition, siPAK1 does not significantly reduce viability in the primary ("normal") epithelial cell line HMEC, whereas it strongly enhances DR5 and DR4 induced reduction of viability in the colon carcinoma cell line HCT15.

Example 58

Synergistic Effect of UbcH10 Antagonist and anti-DR5 Antibody

This example describes synergistic effect of human ubiquitin conjugase UbcH10 (UBE2C) antagonist and anti-DR5 antibody in inducing apoptosis in tumor cells. UbcH10 plays an essential role in cell cycle regulation. Employing global analysis of gene expression and immunohistochemistry, the present inventors found that UbcH10 is significantly over-expressed in carcinomas of multiple anatomic sites, notably breast, stomach/esophagus, colorectum, lung and ovary. The data indicate that UbcH10 plays an important role in tumor development. Therapeutic potential of inhibiting UbcH10 in the treatment of cancers was then examined.

Reduction of cell growth by RNAi-mediated silencing of UbcH10 expression. We first investigated the consequences of gene silencing in tumor cells with high UbcH10 levels, we designed sequences for three different and non-overlapping small interfering RNAs (siRNA) (UbcH10-495, UbcH10-378, UbcH10-412). Each siRNAs was initially tested in 2 cell lines, T3M4 (derived from a pancreatic carcinoma) and DLD-1 (derived from colorectal carcinoma). All three of the siRNAs targeted to UbcH10, but not control siRNA, resulted in efficient diminution of the UbcH10 protein, which correlated with their ability to suppress cell growth. These data underscore the specificity of the UbcH10 siRNAs and indicate that the results are not due to "off-target" effects. Because the UbcH10-APC complex controls cyclin B1 degradation, we also examined the levels of cyclin B1 by Western blot analysis following UbcH10 silencing. Our results revealed an inverse correlation between the levels of UbcH10 protein in cells treated with siUbcH10 and the levels of cyclin B1. Further, cell cycle analysis following siUbcH10 treatment showed arrest in the M-phase (data not shown), consistent with disclosure in the art. Microscopically, down-regulation of UbcH10 did not induce any changes in cell morphology indicative of apoptosis, such as cell rounding, detachment, nuclear condensation or production of apoptotic bodies. Moreover, siUbcH10 treatment did not result in proteolytic processing of the two executioner caspases, caspase-3 and -7 (14), as measured by Western blot analysis and fluorescent caspase activity assays.

Figure 31:
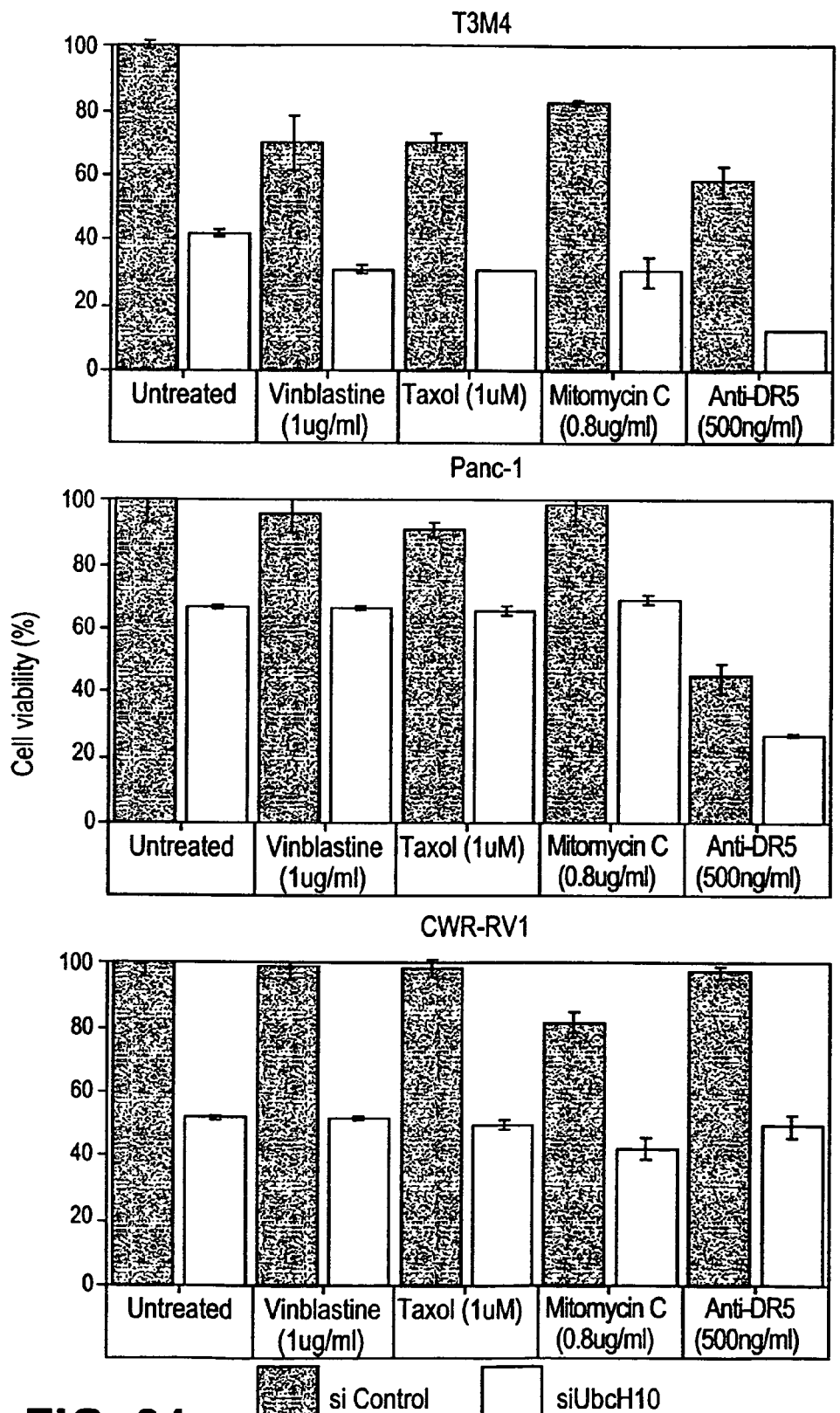
FIG. 31 shows additive effects of siUbcH10 to classic cytotoxic anticancer agents in killing tumor cells. The figure also shows that pre-treatment of tumor cells with siUbcH10 significantly increased the apoptosis induced by anti-DR5 antibodies.

Down-regulating UbcH10 is additive to effects of standard chemotherapeutic drugs: UbcH10 is highly over-expressed in human cancers compared to most normal tissues. To determine therapeutic potential of targeting UbcH10, we surveyed several known chemotherapeutic and a molecularly targeted agent for potential tumor-specific effects subsequent to UbcH10 silencing. For these studies, we employed the microtubule-stabilizing agent paclitaxel, the spindle inhibitor, vinblastine, the DNA alkylation agent, mitomycin c, and a functionally agonistic antibody capable of triggering DR5/TRAIL-mediated apoptosis, to cover a spectrum of agents with different mechanisms of action. Two pancreatic cancer cell lines, T3M4 and Panc-1, and an androgen-independent prostate carcinoma cell line, CWR-RV1, were treated with siUbcH10 for 48 hours followed by incubation with vinblastine, paclitaxel, mitomycin c, and anti-DR5 for an additional 24 hours. The results indicate that co-treatment with mitotic poisons and DNA-damaging drugs following UbcH10 silencing produced an additive reduction in cell viability in a number of tumor cell lines that we tested (FIG. 31). Initial treatment of cancer cells for 48 hours with siUbcH10 reduced the amount of viable cells by >50%, which were be further decreased by the addition of cytotoxic agents for an additional 24 hours. Following normalization for the numbers of UbcH10-silenced cells, the $I_{C90}$ or $I_{C50}$ concentrations were identical, indicating an additive effect. All three independent siRNAs targeted to UbcH10 exhibited similar effects with TRAIL in T3M4 and Panc-1 cells. The data are the mean of triplicates and similar results were obtained in four independent experiments.

Figure 32:
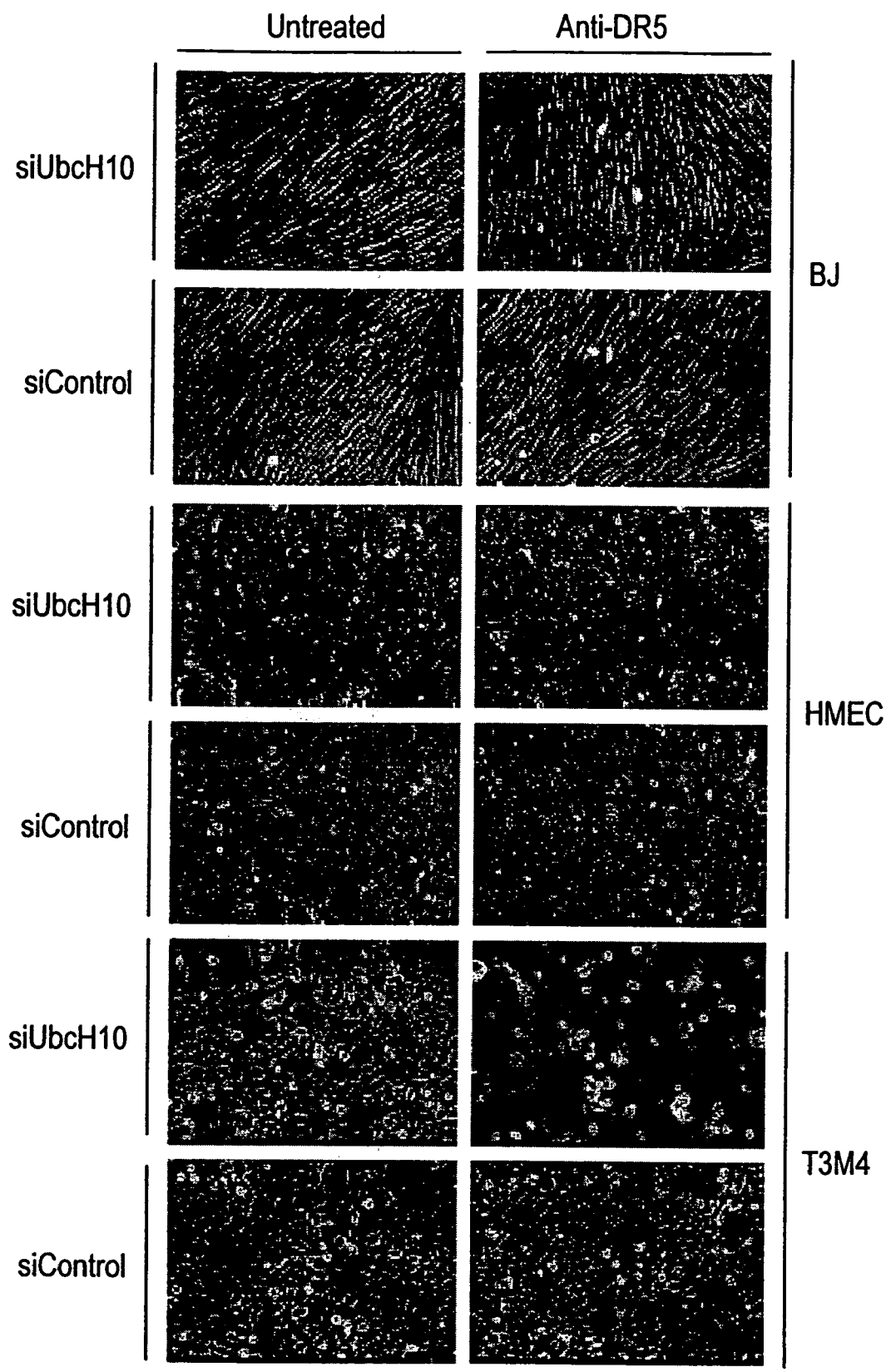
FIG. 32 shows down-regulating UbcH10 with siUbcH10 sensitizes tumor cells to TRAIL/DR5-mediated cell killing.
Figure 33:
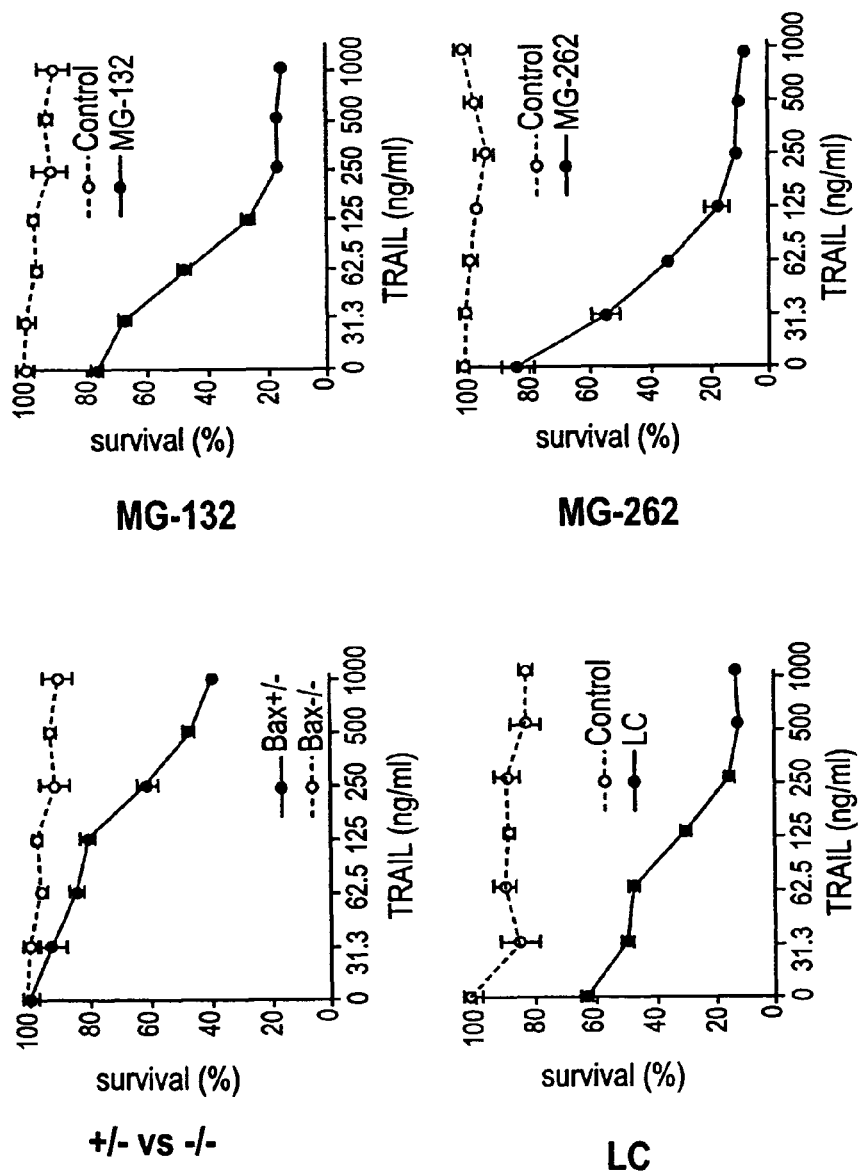
FIG. 33 illustrates sensitization of HCT116 cells or Bax-thereof to TRAIL ligand combined with the 26S proteasome inhibitors MG-132, MG-262, or Lactacystin (LC).

Down-regulating UbcH10 sensitizes cells to TRAIL/DR5-mediated cell killing: Primary human fibroblasts (BJ), human mammary epithelial cells (HMEC), and T3M4 cells were sequentially treated with siUbcH10 (siUbcH10-495) for 48 hours followed by agonistic anti-DR5 antibodies (500 ng/ml) for an additional 6 hours. Fluorescent (FITC)-labeled control siRNAs were used to ensure equal transfection efficacy of all cell lines including BJ and HMEC cells. Cells were analyzed by microscopy. The results were shown in FIGS. 31 and 32. As illustrated in the figures, pre-treatment of T3M4 and Panc-1 cells with siUbcH10significantly increased the apoptosis induced by anti-DR5 antibodies compared to siRNA or anti-DR5 treatment alone, whereas it had a negligible effect in CWR-RV1 cells, which are TRAIL insensitive (FIG. 31). The data indicated that incubation of cancer cell lines, most notably, T3M4, with anti-DR5 antibody subsequent to siUbcH10 treatment exhibited dramatically enhanced apoptosis. This was not seen in primary human skin fibroblasts (BJ) or mammary epithelial cells (HMEC) (FIGS. 31 and 32). This observation seems to reflect a general phenomenon, since other TRAIL resistant tumor cell lines as well as normal cells were not made sensitive to TRAIL by down-regulation of UbcH10.

Example 59

Synergy of anti-DR4 or anti-DR5 agonists and proteasome inhibitors against Bax-defective tumor cells.

Defects in the DNA repair system (mismatch repair (MMR)) lead to genetic instability because replication errors are not corrected. This type of genetic instability is a key event in the malignant progression of hereditary non-polyposis colorectal cancer (HNPCC) and a subset of sporadic colon cancers and mutation rates are particularly high at short repetitive sequences, such as those contained in the TGFbetaRII and BAX genes. Thus, Bax loss in these tumors provides a severe survival advantage to natural and chemotherapeutic induction of apoptosis.

FIG. 34 illustrates that loss of Bax confers resistance to TRAIL ligand. However, proteasome inhibition restores sensitivity to TRAIL. Proteasome inhibition by peptidyl-based inhibitors MG-132 or MG262 or Lactacystin, a natural compound, completely restores sensitivity to TRAIL in cells deficient in Bax. See, FIG. 34.

Proteasome inhibitors circumvent defects in the mitochondrial apoptosis pathway. Depending on the cell type, active caspase-8 can lead directly to the activation of downstream effector caspases like caspase-3 (so called type-I-cells). In type-II-cells (most cells including HCT116), the two prototypical pathways, extrinsic (death-receptor) and intrinsic (mitochondrial), are interconnected by caspase-8-mediated cleavage of the pro-apoptotic bcl-2 family member Bid, which promotes the mitochondrial release of cytochrome c and SMAC. Once released into the cytoplasm, cytochrome c associates with Apaf-1 and pro-caspase-9 forming the "apoptosome", which leads to the activation of pro-caspase-9 and subsequent activation of effector caspases such as caspase-3. Cytosolic SMAC, on the other hand, binds to members of the IAP (inhibitor of apoptosis) protein family and thereby prevents IAP inhibition of caspase-3 and -9.

These events were readily observed by western blot analysis in TRAIL-treated Bax +/− cells (SMAC and cytochrome-c release not shown). See, FIG. 34. Likewise, in Bax −/− cells treated with TRAIL (T), caspase-8 processing and Bid processing occur as normal, however, caspase-9 and complete caspase-3 processing and maturation do not (lanes 2, 3 and 4). This is as expected since Bax loss prevents events downstream of Bid cleavage because the resulting pro-apoptotic fragment of Bid requires Bax for these events. TRAIL (T)+ MG-262 (M) completely restores the mitochondrial pathway resulting in caspase-9 and caspase-3 processing and activation leading to cell death. MG-262 (M) on its own has no effect on this proteolytic cascade. These and other data indicate that proteasome inhibition is useful in resensitizing tumor cells containing defects in the mitochondrial apoptosis pathway to apoptosis induced by TRAIL receptor agonists.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, Genbank sequences, patents, and patent applications cited in this specification are herein incorporated by reference as if each was specifically and individually indicated to be incorporated by reference.

What is claimed is:

1. A method of inducing apoptosis in a cancer cell, the method comprising contacting the cell with:
   i. an anti-DR5 affinity agent agonist; and
   ii. an apoptosis-inducing agent,
   wherein the apoptosis-inducing agent comprises TRAIL,
   wherein the anti-DR5 affinity agent agonist is an anti-DR5 antibody comprising the complementarity determining regions of SEQ ID NO: 8 and SEQ ID NO: 10, and wherein the anti-DR5 affinity agent agonist and the apoptosis-inducing agent act synergistically to induce apoptosis in cancer cells.

2. The method of claim 1, wherein the agonist is a humanized antibody.

3. The method of claim 1, wherein the agonist is a single chain antibody.

4. The method of claim 1, wherein TRAIL is endogenous.

5. The method of claim 1, wherein the apoptosis-inducing agent further comprises one or more additional apoptosis-inducing agents.

6. The method of claim 1, wherein the cancer cell is a colon cancer cell or a pancreatic cancer cell.

7. A method of inducing apoptosis in a cancer cell in an individual in need thereof, the method comprising administering to the individual a therapeutically effective amount of:
   i. an anti-DR5 affinity agent agonist; and
   ii. an apoptosis-inducing agent,
   wherein the apoptosis-inducing agent comprises TRAIL,
   wherein the anti-DR5 affinity agent agonist is an anti-DR5 antibody comprising the complementarity determining regions of SEQ ID NO: 8 and SEQ ID NO: 10, and wherein the anti-DR5 affinity agent agonist and the apoptosis-inducing agent act synergistically to induce apoptosis in cancer cells.

8. The method of claim 7, wherein (i) the anti-DR5 affinity agent agonist and (ii) the apoptosis-inducing agent are administered separately.

9. The method of claim 7, wherein (i) the anti-DR5 affinity agent agonist and (ii) the apoptosis-inducing agent are administered as a mixture.

10. The method of claim 7, wherein the agonist is a humanized antibody.

11. The method of claim 7, wherein the agonist is a single chain antibody.

12. The method of claim 7, wherein the apoptosis-inducing agent further comprises one or more additional apoptosis-inducing agents.

13. The method of claim 7, wherein the cancer cell is a colon cancer cell or a pancreatic cancer cell.

14. A physiological composition comprising:
    i. an anti-DR5 affinity agent agonist; and
    ii. an apoptosis-inducing agent,
    wherein the apoptosis-inducing agent comprises TRAIL,
    wherein the anti-DR5 affinity agent agonist is an anti-DR5 antibody comprising the complementarity determining regions of SEQ ID NO: 8 and SEQ ID NO: 10, and wherein the anti-DR5 affinity agent agonist and the apoptosis-inducing agent act synergistically to induce apoptosis in cancer cells.

15. The physiological composition of claim 14, wherein the agonist is a humanized antibody.

16. The physiological composition of claim 14, wherein the agonist is a single chain antibody.

17. The composition of claim 14, wherein the apoptosis-inducing agent further comprises one or more additional apoptosis-inducing agents.

* * * * *